United States Patent
Maeda et al.

(10) Patent No.: US 12,139,537 B2
(45) Date of Patent: Nov. 12, 2024

(54) ANTIBODY INDUCING IMMUNE TOLERANCE, INDUCED LYMPHOCYTE, AND CELL THERAPY AGENT THERAPEUTIC METHOD USING INDUCED LYMPHOCYTE

(71) Applicant: JUNTEN BIO Co., Ltd., Tokyo (JP)

(72) Inventors: Ryu Maeda, Sapporo (JP); Masayuki Kawakami, Sapporo (JP); Koichiro Uchida, Tokyo (JP); Kazuyoshi Takeda, Tokyo (JP); Ko Okumura, Tokyo (JP)

(73) Assignee: Junten Bio Co., Ltd., Tokyo (JP)

( * ) Notice: Subject to any disclaimer, the term of this patent is extended or adjusted under 35 U.S.C. 154(b) by 894 days.

(21) Appl. No.: 17/254,006

(22) PCT Filed: Jun. 21, 2019

(86) PCT No.: PCT/JP2019/024752
§ 371 (c)(1),
(2) Date: Dec. 18, 2020

(87) PCT Pub. No.: WO2019/245037
PCT Pub. Date: Dec. 26, 2019

(65) Prior Publication Data
US 2021/0269529 A1    Sep. 2, 2021

(30) Foreign Application Priority Data

Jun. 22, 2018  (JP) ................. 2018-118996

(51) Int. Cl.
| | | |
|---|---|---|
| *C07K 16/28* | (2006.01) | |
| *A61K 35/17* | (2015.01) | |
| *A61K 39/00* | (2006.01) | |
| *A61P 37/06* | (2006.01) | |
| *C12N 5/0783* | (2010.01) | |

(52) U.S. Cl.
CPC .......... *C07K 16/2827* (2013.01); *A61K 35/17* (2013.01); *A61P 37/06* (2018.01); *C12N 5/0636* (2013.01); *A61K 2039/505* (2013.01); *C07K 2317/24* (2013.01); *C07K 2317/52* (2013.01); *C07K 2317/565* (2013.01); *C07K 2317/76* (2013.01); *C12N 2501/998* (2013.01)

(58) Field of Classification Search
None
See application file for complete search history.

(56) References Cited

FOREIGN PATENT DOCUMENTS

| CN | 101367877 A | 2/2009 | |
|---|---|---|---|
| JP | 2002-504120 A | 2/2002 | |
| JP | 2007-131598 A | 5/2007 | |
| JP | 2016-520081 A | 7/2016 | |
| TW | 201336510 A | 9/2013 | |
| WO | WO 199640878 A1 | 12/1996 | |
| WO | 98/56417 A1 | 12/1998 | |
| WO | 01/89567 A1 | 11/2001 | |
| WO | 2004/076488 A1 | 9/2004 | |
| WO | WO 2010009391 A1 | 1/2010 | |
| WO | WO-2011003557 A1 * | 1/2011 | ........... A61K 31/704 |
| WO | 2014/186193 A1 | 11/2014 | |

OTHER PUBLICATIONS

Bashuda et al., "Renal allograft rejection is prevented by adoptive transfer of anergic T cells in nonhuman primates," *J. Clin. Invest.* 115:1896-1902, 2005.
Blazevic et al., "Analysis of the Costimulatory Requirements for Generating Human Virus-Specific in Vitro T Helper and Effector Responses," *Journal of Clinical Immunology* 21(4):293-302, 2001.
Inoue et al., "Effect of Anti-B7-1 and Anti-B7-2 mAb on Theiler's murine Encephalomyelitis Virus-Induced Demyelinating Disease," *The Journal of Immunology* 163:6180-6186, 1999.
Teraoka et al., "A Clinical Trial Aiming at Tolerance Induction by Adoptive Transfer of Ex Vivo-Induced, Donor-Specific Treg-Like Cells in Clinical Kidney Transplantation," *J Transplant Res* 2(1):doi http://dx.doi.org/10.16966/2473-1730.115, 2017, 8 pages.
Todo et al., "A Pilot Study of Operational Tolerance With a Regulatory T-Cell-Based Cell Therapy in Living Donor Liver Transplantation," *Hepatology* 64(2):632-643, 2016.
Haegel-Kronenberger et al., "Inhibition of costimulation allows for repeated systemic administration of adenoviral vector in rhesus monkeys," *Gene Therapy* 11:241-252, 2004.
Roitt et al., *Immunology* pp. 110-111, 2000 (5 pages).
Watanabe, "Treatment strategies for nodal and gastrointestinal follicular lymphoma: Current status and future development," *World J Gastroenterol* 16(44):5543-5554, Nov. 2010.

(Continued)

*Primary Examiner* — Daniel E Kolker
*Assistant Examiner* — Maureen Varina Driscoll
(74) *Attorney, Agent, or Firm* — Seed IP Law Group LLP

(57) ABSTRACT

The present disclosure provides an antibody for inducing immune tolerance, an induced lymphocyte, and a cell therapy agent therapeutic method using the induced lymphocyte. Specifically, the present disclosure provides an antibody that inhibits the interaction between CD80 and/or CD86 expressed on the surface of a certain cell and CD28 expressed on the surface of another cell, and substantially does not induce immune activation-induced cytokines. In a specific embodiment, the Fc portion of the antibody substantially does not produce the immune activation-induced cytokines.

14 Claims, 8 Drawing Sheets

Specification includes a Sequence Listing.

(56) References Cited

OTHER PUBLICATIONS

Vierboom et al., "Induction of allograft tolerance through costimulatory blockade: first selection of drugs in vitro," *Transplant Immunology* 11:215-222, Apr.-Jun. 2003. (8 pages).

Khubutiya et al., "Immunological tolerance in organ transplantation," *Transplantologiva* 9(3):211-225, 2017.

Fisher Scientific, "CD80 (B7-1) Mouse anti-Human, Functional Grade, Clone: 2D10.4, eBioscience™," URL= https://www.fishersci.se/shop/products/cd80-b7-1-mouse-anti-human-clone-2d10-4-functional-grade-ebioscience/15218517, retrieved Aug. 21, 2019, 2 pages.

Fisher Scientific, "CD86 (B7-2) Mouse anti-Human, Functional Grade, Clone: IT2.2, eBioscience™," URL= https://www.fishersci.se/shop/products/cd86-b7-2-mouse-anti-human-clone-it2-2-functional-grade-ebioscience/15218527, retrieved Aug. 21, 2019, 2 pages.

\* cited by examiner

ANTIBODY INDUCING IMMUNE TOLERANCE, INDUCED LYMPHOCYTE, AND CELL THERAPY AGENT THERAPEUTIC METHOD USING INDUCED LYMPHOCYTE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 500059_401USPC_SEQUENCE_LISTING.txt. The text file is 103 KB, was created on Dec. 17, 2020, and is being submitted electronically via EFS-Web.

TECHNICAL FIELD

The present disclosure relates to a novel technology related to immune tolerance. More specifically, the present disclosure relates to an antibody that induces immune tolerance, induced lymphocyte, or cell therapy agent/therapeutic method using an induced lymphocyte.

BACKGROUND ART

Liver transplantation has been widely used as the final treatment on terminal liver failure patients. 20,000 or more liver transplantations are performed abroad, and more than 500 are performed in Japan annually.

Transplantation is one of the primary treatments chosen for terminal organ failure of the kidney, heart, liver, pancreas, or the like. Despite the dramatic advancement in the treatment of graft rejection in recent years, the majority of transplantations are ultimately rejected without any immunosuppressive regimen. Today's drug immunosuppressive regimen which is dependent on continuous drug therapy suppresses not only responses that are clearly directed to transplantation, but also all immune responses, such that organ transplant patients become more vulnerable to increased sensitivity to infections and cancer.

While regenerative medicine has also drawn attention, immune rejection can ultimately occur without any autologous cells even if induced pluripotent stem cells (iPS cells) or the like are used. Thus, immune tolerance technologies have garnered attention.

Such technologies for inducing immune tolerance include induction of an antigen specific non-immune response (anergy) of T cells. Specific technologies reported include a technology for directly administering an antibody which inhibits interactions between CD80/CD86 on antigen presenting cells and CD28 on unactivated (naïve) T cells to an organ transplant patient to induce donor antigen specific anergy in the body (Patent Literature 1) and a technology of co-culturing recipient cells and radiation irradiated donor cells in the presence of the same antibody to induce donor antigen specific anergic cells ex vivo and returning said cells to the recipient (Patent Literature 2, Patent Literature 3, and Non Patent Literatures 1 to 3)

CITATION LIST

Patent Literature

[PTL 1] Japanese National Phase PCT Laid-open Publication No. 2002-504120

[PTL 2] Japanese National Phase PCT Laid-open Publication No. 2007-131598

[PTL 3] Japanese National Phase PCT Laid-open Publication No. 2016-520081

Non Patent Literature

[NPL 1] Satoru Todo et al. Hepatorogy, 64 (vol. 2), 632-643 (2016)

[NPL 2] Teraoka S, Koyama I, Bashuda H, Uchida K, Tonsho M, et al. (2017) J Transplant Res 2(1) p1-8

[NPL 3] Bashuda H et al., J. Clin. Invest. 115: 1896-1902 (2005).

SUMMARY OF INVENTION

Solution to Problem

The inventors attempted to induce a non-immune response (anergy) using an antibody with a specific human Fc region that inhibits the interaction between CD80/CD86 and CD28, resulting in discovering that binding to a cell involved in the immune system such as a macrophage, neutrophil, or natural killer (NK) cell activates these cells and induces the release of a humoral factor such as interleukin or interferon (IFN) that is responsible for immune responses. The inventors newly discovered that release of these humoral factors induces disadvantageous activation of the immune system that is the opposite of immune tolerance, so that the effect of immune tolerance can be improved, or the attenuation of the effect of immune tolerance can be suppressed by adjusting the induction of non-immune responses (anergy) using an antibody with a human Fc region that does not bind to these cells. The inventors thereby provide an antibody with a structure having a feature of improving, or not attenuating, the effect of immune tolerance.

Therefore, the present disclosure provides the following.

(1) An antibody or variant thereof that inhibits an interaction between CD80 and/or CD86 expressed on a surface of a cell, and CD28 expressed on a surface of another cell, wherein the antibody or variant thereof does not substantially induce the production of a cytokine by immunostimulation.

(2) The antibody or variant thereof of the preceding item, wherein the cytokine comprises interferon γ.

(3) The antibody or variant thereof of any of the preceding items, which is a chimeric antibody.

(4) The antibody or variant thereof of any one of the preceding items, wherein a subclass of the antibody is IgG1.

(5) The antibody or variant thereof of any of the preceding items, having a heavy chain with the amino acid sequence set forth in SEQ ID NO: 38 or 42, and a light chain with the amino acid sequence set forth in SEQ ID NO: 40 or 44.

(6) The antibody or variant thereof of any of the preceding items, comprising:

(a) a VH comprising CDRH1 of the amino acid sequence set forth in SEQ ID NO: 53, CDRH2 of the amino acid sequence set forth in SEQ ID NO: 54, and CDRH3 of the amino acid sequence set forth in SEQ ID NO: 55, and a VL comprising CDRL1 of the amino acid sequence set forth in SEQ ID NO: 56, CDRL2 of the amino acid sequence set forth in SEQ ID NO: 57, and CDRL3 set forth in SEQ ID NO: 58; or (b) a VH comprising CDRH1 of the amino acid sequence set forth in SEQ ID NO: 59, CDRH2 of the amino acid sequence set forth in SEQ ID NO: 60, and CDRH3 of the amino acid sequence set forth in SEQ ID NO: 61, and a VL comprising CDRL1 of the amino acid sequence set forth in SEQ ID NO: 62, CDRL2 of the amino acid sequence set forth in SEQ ID NO: 63, and CDRL3 set forth in SEQ ID NO: 64.

(7) The antibody or variant thereof of any of the preceding items, comprising:
(a) a VH having the amino acid sequence set forth in SEQ ID NO: 46 or a variant sequence thereof, and a VL having the amino acid sequence set forth in SEQ ID NO: 48 or a variant sequence thereof; or
(b) a VH having the amino acid sequence set forth in SEQ ID NO: 50 or a variant sequence thereof, and a VL having the amino acid sequence set forth in SEQ ID NO: 52 or a variant sequence thereof.

(8) The antibody or variant thereof of any of the preceding items, wherein an Fc moiety of the antibody is a moiety that does not substantially induce the production of a cytokine by immunostimulation.

(9) The antibody or variant thereof of any of the preceding items, wherein a subclass of the antibody is IgG2 or IgG4.

(10) The antibody or variant thereof of any of the preceding items, wherein a subclass of the antibody is IgG4.

(11) The antibody or variant thereof of any of the preceding items, wherein the variant of the antibody is a variant lacking an Fc moiety of the antibody.

(12) The antibody or variant thereof of any of the preceding items, wherein the variant of the antibody is an Fab antibody, an F(ab')$_2$ antibody, an Fab' antibody, an Fv antibody, or an scFv antibody.

(13) The antibody or variant thereof of any of the preceding items, having an ability to induce immune tolerance.

(14) The antibody or variant thereof of any of the preceding items, wherein the cell expressing CD80 and/or CD86 is an antigen presenting cell, and the another cell expressing CD28 is a T cell.

(15) The antibody of any of the preceding items, wherein the antibody or variant thereof is an antagonistic anti-CD80 antibody, an antagonistic anti-CD86 antibody, an antagonistic anti-CD28 antibody, or an antagonistic bispecific antibody to CD80 and CD86, or a variant thereof.

(16) The antibody or variant thereof of any of the preceding items, which is a humanized antibody or a human antibody, or a variant thereof.

(17) The antibody or variant thereof of any of the preceding items, comprising an Fc moiety of IgG2 or IgG4 of a human antibody.

(18) The antibody or variant thereof of any of the preceding items, comprising an Fc moiety of IgG4 of a human antibody.

(19) The antibody or variant thereof of any of the preceding items, comprising:
(a) a VH comprising CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, and a VL comprising CDRL1 of the amino acid sequence set forth in SEQ ID NO: 28, CDRL2 of the amino acid sequence set forth in SEQ ID NO: 29, and CDRL3 set forth in SEQ ID NO: 30; or
(b) a VH comprising CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33, and a VL comprising CDRL1 of the amino acid sequence set forth in SEQ ID NO: 34, CDRL2 of the amino acid sequence set forth in SEQ ID NO: 35, and CDRL3 set forth in SEQ ID NO 36.

(20) The antibody or variant thereof of any of the preceding items, comprising:
(a) a VH having the amino acid sequence set forth in SEQ ID NO: 18 or a variant sequence thereof, and a VL having the amino acid sequence set forth in SEQ ID NO: 20 or a variant sequence thereof; or
(b) a VH having the amino acid sequence set forth in SEQ ID NO: 22 or a variant sequence thereof, and a VL having the amino acid sequence set forth in SEQ ID NO: 24 or a variant sequence thereof.

(21) A nucleic acid molecule encoding the amino acid sequence or a portion thereof of the antibody or variant thereof of any of the preceding items.

(22) The nucleic acid molecule of any of the preceding items, comprising:
(a) a polynucleotide encoding a VH, having the nucleotide sequence set forth in SEQ ID NO: 17 or SEQ ID NO: 45, and a polynucleotide encoding a VL, having the nucleotide sequence set forth in SEQ ID NO: 19 or SEQ ID NO: 47; or
(b) a polynucleotide encoding a VH, having the nucleotide sequence set forth in SEQ ID NO: 21 or SEQ ID NO: 49, and a polynucleotide encoding a VL, having the nucleotide sequence set forth in SEQ ID NO: 23 or SEQ ID NO: 51.

(23) A vector having the nucleic acid molecule of any of the preceding items.

(24) A cell comprising the nucleic acid molecule of any of the preceding items or the vector of item 23.

(25) A manufacturing method of the antibody or variant thereof of any of the preceding items, comprising culturing the cell of any of the preceding items.

(26) A cell having immune tolerance induced with the antibody or variant thereof of any of the preceding items.

(27) The cell of any of the preceding items, wherein the immune tolerance is induced by mixing the antibody or variant thereof, a cell derived from a subject, and an antigen that is not derived from the subject or a material containing the antigen.

(28) A composition for preparing a cell having immune tolerance induced, comprising at least one of the antibodies or variants thereof of any of the preceding items.

(29) The composition of any of the preceding items, comprising an antagonistic anti-CD80 antibody, an antagonistic anti-CD86 antibody, an antagonistic anti-CD28 antibody, or an antagonistic bispecific antibody to CD80 and CD86, or a variant thereof, or any combination thereof.

(30) A method for manufacturing a cell for treating or preventing a disease, disorder, or condition caused by an antigen that is not derived from a subject, comprising mixing the antibody or variant thereof of any of the preceding items, a cell derived from the subject, and an antigen that is not derived from the subject or a material containing the antigen.

(31) The method of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(32) The method of any of the preceding items, wherein a material containing the antigen is a cell.
(33) A cell manufactured by the method of any of the preceding items.
(34) The cell of any of the preceding items, comprising a T cell.
(35) A cell therapy agent comprising a cell having immune tolerance induced with the antibody or variant thereof of any of the preceding items, a cell manufactured by the method of any of the preceding items, or the cell of any of the preceding items.
(36) A composition for treating or preventing a disease, disorder, or condition caused by an antigen that is not derived from a subject, comprising a cell having immune tolerance induced with the antibody or variant thereof of any of the preceding items, a cell manufactured by the method of any of the preceding items, or the cell of any of the preceding items.
(37) The composition of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(38) The composition of any of the preceding items, wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(39) A method for treating or preventing a disease, disorder, or condition caused by an antigen that is not derived from a subject in the subject, comprising administering to the subject an effective amount of a cell having immune tolerance induced with the antibody or variant thereof of any of the preceding items, a cell manufactured by the method of any of the preceding items, or the cell of any of the preceding items.
(40) The method of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(41) The method of any of the preceding items, wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(39A) Use of a cell having immune tolerance induced with the antibody or variant thereof of any of the preceding items, a cell manufactured by the method of any of the preceding items, or the cell of any of the preceding items, for the manufacture of a medicament for treating or preventing a disease, disorder, or condition caused by an antigen that is not derived from a subject in the subject.
(40A) The use of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(41A) The use of any of the preceding items, wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(39B) A cell having immune tolerance induced with the antibody or variant thereof of any of the preceding items, a cell manufactured by the method of any of the preceding items, or the cell of any of the preceding items, for the manufacture of a medicament for treating or preventing a disease, disorder, or condition caused by an antigen that is not derived from a subject in the subject.
(40B) The cell of any of the preceding items, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(41B) The cell of any of the preceding items, wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

The present disclosure also provides the following.
(A1) An antibody that inhibits an interaction between CD80 and/or CD86 expressed on a surface of a cell, and CD28 expressed on a surface of another cell, wherein the antibody does not substantially induce the production of a cytokine by immunostimulation.
(A2) The antibody of (A1), wherein the cytokine comprises interferon γ.
(A3) The antibody of (A1) or (A2), wherein an Fc moiety of the antibody is a moiety that does not substantially induce the production of a cytokine by immunostimulation.
(A4) The antibody of any one of (A1) to (A3), wherein a subclass of the antibody is IgG2 or IgG4.
(A5) The antibody of (A4), wherein the subclass of the antibody is IgG4.
(A6) The antibody of (A1) or (A2), wherein the antibody lacks an Fc moiety.
(A7) The antibody of (A6), wherein the antibody is an Fab antibody, an F(ab')$_2$ antibody, an Fab' antibody, an Fv antibody, or an scFv antibody.
(A8) The antibody of any one of (A1) to (A7), having an ability to induce immune tolerance.
(A9) The antibody of any one of (A1) to (A8), wherein the cell expressing CD80 and/or CD86 is an antigen presenting cell, and the another cell expressing CD28 is a T cell.
(A10) The antibody of any one of (A1) to (A9), wherein the antibody is an antagonistic anti-CD80 antibody, an antagonistic anti-CD86 antibody, an antagonistic anti-CD28 antibody, or an antagonistic bispecific antibody to CD80 and CD86.
(A11) The antibody of any one of (A1) to (A10), which is a chimeric antibody, a humanized antibody, or a human antibody.

(A12) The antibody of any one of (A1) to (A11), comprising an Fc moiety of IgG2 or IgG4 of a human antibody.
(A13) The antibody of any one of (A1) to (A12), comprising an Fc moiety of IgG4 of a human antibody.
(A14) The antibody of any one of (A1) to (A13), comprising:
(a) a VH comprising CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, and a VL comprising CDRL1 of the amino acid sequence set forth in SEQ ID NO: 28, CDRL2 of the amino acid sequence set forth in SEQ ID NO: 29, and CDRL3 set forth in SEQ ID NO: 30; or
(b) a VH comprising CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33, and a VL comprising CDRL1 of the amino acid sequence set forth in SEQ ID NO: 34, CDRL2 of the amino acid sequence set forth in SEQ ID NO: 35, and CDRL3 set forth in SEQ ID NO: 36.
(A15) The antibody of (A14), comprising:
(a) a VH having the amino acid sequence set forth in SEQ ID NO: 18 or a variant sequence thereof, and a VL having the amino acid sequence set forth in SEQ ID NO: 20 or a variant sequence thereof; or
(b) a VH having the amino acid sequence set forth in SEQ ID NO: 22 or a variant sequence thereof, and a VL having the amino acid sequence set forth in SEQ ID NO: 24 or a variant sequence thereof.
(A16) A nucleic acid molecule encoding the amino acid sequence or a portion thereof of the antibody of any one of (A1) to (A15).
(A17) The nucleic acid molecule of (A16) comprising:
(a) a polynucleotide encoding a VH, having the nucleotide sequence set forth in SEQ ID NO: 17, and a polynucleotide encoding a VL, having the nucleotide sequence set forth in SEQ ID NO: 19; or
(b) a polynucleotide encoding a VH, having the nucleotide sequence set forth in SEQ ID NO: 21, and a polynucleotide encoding a VL, having the nucleotide sequence set forth in SEQ ID NO: 23.
(A18) A vector having the nucleic acid molecule of (A16) or (A17).
(A19) A cell comprising the nucleic acid molecule of (A16) or (A17) or the vector of (A18).
(A20) A manufacturing method of the antibody of any one of (A1) to (A15), comprising culturing the cell of (A19).
(A21) A cell having immune tolerance induced with the antibody of any one of (A1) to (A15).
(A22) The cell of (A21), wherein the immune tolerance is induced by mixing the antibody, a cell derived from a subject, and an antigen that is not derived from the subject or a material containing the antigen.
(A23) A composition for preparing a cell having immune tolerance induced, comprising at least one of the antibodies of any one of (A1) to (A15).
(A24) The composition of (A23), comprising an antagonistic anti-CD80 antibody, an antagonistic anti-CD86 antibody, an antagonistic anti-CD28 antibody, or an antagonistic bispecific antibody to CD80 and CD86, or any combination thereof.
(A25) A method for manufacturing a cell for treating or preventing a disease, disorder, or condition caused by an antigen that is not derived from a subject, comprising mixing the antibody of any one of (A1) to (A15), a cell derived from the subject, and an antigen that is not derived from the subject or a material containing the antigen.
(A26) The method of (A25), wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(A27) The method of (A25) or (A26), wherein the material containing the antigen is a cell.
(A28) A cell manufactured by the method of any one of (A25) to (A27).
(A29) The cell of (A28), comprising a T cell.
(A30) A cell therapy agent comprising a cell having immune tolerance induced with the antibody of any one of (A1) to (A15), a cell manufactured by the method of (A25) or (A26), or the cell of (A21), (A22), (A28), or (A29).
(A31) A composition for treating or preventing a disease, disorder, or condition caused by an antigen that is not derived from a subject, comprising a cell having immune tolerance induced with the antibody of any one of (A1) to (A15), a cell manufactured by the method of (A25) or (A26), or the cell of (A21), (A22), (A28), or (A29).
(A32) The composition of (A31), wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(A33) The composition of (A32), wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a corneal, an eye ball, or a bone marrow.
(A34) A method for treating or preventing a disease, disorder, or condition caused by an antigen that is not derived from a subject in the subject, comprising administering to the subject an effective amount of a cell having immune tolerance induced with the antibody of any one of (A1) to (A15), a cell manufactured by the method of (A23) or (A24), or the cell of (A21), (A22), (A28), or (A29).
(A35) The method of (A34), wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.
(A36) The method of (A35), wherein the rejection is characterized in that a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.

The present disclosure further relates to the following inventions.
(B1) An antibody having a human Fc region, wherein the antibody can inhibit an interaction between CD80 or CD86 expressed on a cell surface and CD28 expressed on another cell surface, and does not promote cytokine production by a human PBMC.

(B2) The antibody of (B1), which can inhibit an interaction between CD80 or CD86 expressed on an antigen presenting cell surface and CD28 expressed on a T cell surface.

(B3) The antibody of (B1) or (B2), which can induce immune tolerance to an antigen by contacting the antibody with a PBMC together with the antigen or a cell having the antigen on a surface.

(B4) The antibody of any one of (B1) to (B3), wherein a cytokine is IFNγ.

(B5) The antibody of any one of (B1) to (B4), which is an anti-CD80 antibody or an anti-CD86 antibody.

(B6) The antibody of any one of (B1) to (B5), which is a chimeric antibody, a humanized antibody, or a human antibody.

(B7) The antibody of any one of (B1) to (B6), which is a monoclonal antibody.

(B8) The antibody of any one of (B1) to (B7), whose subclass is IgG2 or IgG4.

(B8A) The antibody of any one of (B1) to (B7), whose subclass is IgG1.

(B8B) The antibody of (B8A), having a heavy chain with the amino acid sequence set forth in a SEQ ID NO. selected from SEQ ID NOs: 38 and 42.

(B8C) The antibody of (B8B), having:
a heavy chain with the amino acid sequence set forth in SEQ ID NO: 38 and a light chain with the amino acid sequence set forth in SEQ ID No: 40, or
a heavy chain with the amino acid sequence set forth in SEQ ID NO: 42 and a light chain with the amino acid sequence set forth in SEQ ID No: 44.

(B8D) The antibody of any one of (B1) to (B7) and (B8A) to (B8C), having CDRH3 of the amino acid sequence set forth in SEQ ID NO: 55 or 61.

(B8E) The antibody of (B8D), which is
(Bi) an antibody having CDRH1 of the amino acid sequence set forth in SEQ ID NO: 53, CDRH2 of the amino acid sequence set forth in SEQ ID NO: 54, and CDRH3 of the amino acid sequence set forth in SEQ ID NO: 55, or
(Bii) an antibody having CDRH1 of the amino acid sequence set forth in SEQ ID NO: 59, CDRH2 of the amino acid sequence set forth in SEQ ID NO: 60, and CDRH3 of the amino acid sequence set forth in SEQ ID NO: 61.

(B8F) The antibody of (Bi) of (B8E), having CDRL1 of the amino acid sequence set forth in SEQ ID NO: 56, CDRL2 of the amino acid sequence set forth in SEQ ID NO: 57, and CDRL3 of the amino acid sequence set forth in SEQ ID NO: 58, or
the antibody of (Bii) of (B8E), having CDRL1 of the amino acid sequence set forth in SEQ ID NO: 62, CDRL2 of the amino acid sequence set forth in SEQ ID NO: 63, and CDRL3 of the amino acid sequence set forth in SEQ ID NO: 64.

(B8G) The antibody of (B8D), having a heavy chain variable region (VH) with the amino acid sequence set forth in SEQ ID NO: 46 or 50.

(B8H) The antibody of (B8G), having a VH with the amino acid sequence set forth in SEQ ID NO: 46 and a light chain variable region (VL) with the amino acid sequence set forth in SEQ ID NO: 48, or having a VH with the amino acid sequence set forth in SEQ ID NO: 50 and a VL with the amino acid sequence set forth in SEQ ID NO: 52.

(B8I) The antibody of (B8G), having a heavy chain with the amino acid sequence set forth in a SEQ ID NO. selected from SEQ ID NOs: 38 and 42.

(B8J) The antibody of (B8I) having:
a heavy chain with the amino acid sequence set forth in SEQ ID NO: 38 and a light chain with the amino acid sequence set forth in SEQ ID NO: 40, or
a heavy chain with the amino acid sequence set forth in SEQ ID NO: 42 and a light chain with the amino acid sequence set forth in SEQ ID NO: 44.

(B9) The antibody of any one of (B1) to (B8), having CDRH3 of the amino acid sequence set forth in SEQ ID NO 27 or 33.

(B10) The antibody of (B9), which is
(Bi) an antibody having CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, or
(Bii) an antibody having CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33.

(B11) The antibody of (Bi) of (B10), having CDRL1 of the amino acid sequence set forth in SEQ ID NO: 28, CDRL2 of the amino acid sequence set forth in SEQ ID NO: 29, and CDRL3 of the amino acid sequence set forth in SEQ ID NO: 30, or
the antibody of (Bii) of (B10), having CDRL1 of the amino acid sequence set forth in SEQ ID NO: 34, CDRL2 of the amino acid sequence set forth in SEQ ID NO: 35, and CDRL3 of the amino acid sequence set forth in SEQ ID NO: 36.

(B12) The antibody of (B9), having a heavy chain variable region (VH) with the amino acid sequence set forth in SEQ ID NO: 18 or 22.

(B13) The antibody of (B12) having a VH with the amino acid sequence set forth in SEQ ID NO: 18 and a light chain variable region (VL) with the amino acid sequence set forth in SEQ ID NO: 20, or having a VH with the amino acid sequence set forth in SEQ ID NO: 22 and a VL with the amino acid sequence set forth in SEQ ID NO: 24.

(B14) The antibody of (B12), having a heavy chain with the amino acid sequence set forth in a SEQ ID NO. selected from SEQ ID NOs: 2, 6, 10, and 14.

(B15) The antibody of (B14) having:
a heavy chain with the amino acid sequence set forth in SEQ ID NO: 2 and a light chain with the amino acid sequence set forth in SEQ ID NO: 4;
a heavy chain with the amino acid sequence set forth in SEQ ID NO: 6 and a light chain with the amino acid sequence set forth in SEQ ID NO: 8;
a heavy chain with the amino acid sequence set forth in SEQ ID NO: 10 and a light chain with the amino acid sequence set forth in SEQ ID NO: 12; or
a heavy chain with the amino acid sequence set forth in SEQ ID NO: 14 and a light chain with the amino acid sequence set forth in SEQ ID NO: 16.

(B16) A medical composition comprising the antibody of any one of (B1) to (B15).

(B17) The medical composition of (B16), comprising an anti-CD80 antibody anti-CD86 antibody.

(B18) The medical composition of (B16) or (B17) used for inducing immune tolerance.

(B19) The medical composition of (B18) used for inducing immune tolerance in a cell collected from a patient receiving organ transplantation.
(B20) The medical composition of (B19) or (B20), wherein an organ to be transplanted is a heart, a kidney, or a liver.
(B21) The medical composition of (B18) used for inducing immune tolerance in a patient with an autoimmune disease or an allergic disease.
(B22) A nucleic acid molecule encoding the amino acid sequence of the antibody of any one of (B12) to (B15).
(B23) The nucleic acid molecule of (B22) comprising a polynucleotide encoding a VH with the nucleotide sequence set forth in any one selected from SEQ ID NOs: 1, 5, 9, and 13 and a polynucleotide encoding a VL with the nucleotide sequence set forth in any one selected from SEQ ID NOs: 3, 7, 11, and 15.
(B24) A vector having the nucleic acid molecule of (B22) or (B23).
(B25) A host cell having the vector of (B24).
(B26) A method of manufacturing the antibody of any one of (B1) to (B15), comprising culturing the host cell of (B25).
(B27) A method of inducing immune tolerance to an antigen of a PBMC, comprising contacting the antibody of any one of (B1) to (B15), an antigen for which immune tolerance is to be induced or a cell with the antigen on a surface, and the PBMC.
(B28) The inducing method of (B27), which is performed ex vivo.
(B29) The method of (B27) or (B28), wherein the PBMC is a cell collected from a patient receiving organ transplantation.
(B30) The method of (B27) or (B28), wherein the PBMC is a cell collected from a patient with an autoimmune disease or an allergic disease.
(B31) A PBMC having immune tolerance induced by the method of any one of (B27) to (B30).
(B32) A cell therapy agent comprising the PBMC of (B30) as an active ingredient.
(B33) The cell therapy agent of (B32) for suppressing rejection in organ transplantation.
(B34) The cell therapy agent of (B33), wherein a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(B35) The cell therapy agent of (B32) for treating an autoimmune disease or an allergic disease.
(B36) A method of suppressing a rejection in organ transplantation, comprising administering the antibody of any one of (B1) to (B15) to a patient receiving organ transplantation.
(B37) The method of (B36), wherein a transplanted organ is a kidney, a liver, a heart, skin, a lung, a pancreas, an esophagus, a stomach, a small intestine, a large intestine, a nerve, blood, a blood cell including an immune system cell, a bone, a cartilage, a blood vessel, a cornea, an eye ball, or a bone marrow.
(B37) A method of treating an autoimmune disease or an allergic disease, comprising administering the antibody of any one of (B1) to (B15) to a patient with an autoimmune disease or an allergic disease.
(B38) A method of suppressing rejection in organ transplantation, comprising administering the cell therapy agent of any one of (B32) to (B34) to a patient receiving organ transplantation.
(B39) A method of treating an autoimmune disease or an allergic disease, comprising administering the cell therapy agent of (B32) or (B35) to a patient with an autoimmune disease or an allergic disease.
(B40) The method of any one of (B27) to (B30), further comprising administering a PBMC with immune tolerance induced to a patient.
(B41) The method of (B40), comprising administering to a patient receiving organ transplantation a PBMC derived from a patient with immune tolerance to an organ to be transplanted induced.
(B42) The method of (B40), comprising administering to a patient with an autoimmune disease or an allergic disease a PBMC derived from a patient with immune tolerance to an antigen, which is a cause of an autoimmune disease or an allergic disease induced.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The antibody of the present disclosure suppresses IFNγ production while maintaining the ability to induce immune tolerance. In particular, the antibodies of subclass IgG2 or IgG4 of the present disclosure can manufacture a cell with induced immune tolerance without producing IFNγ.

DESCRIPTION OF EMBODIMENTS

Figure 1:
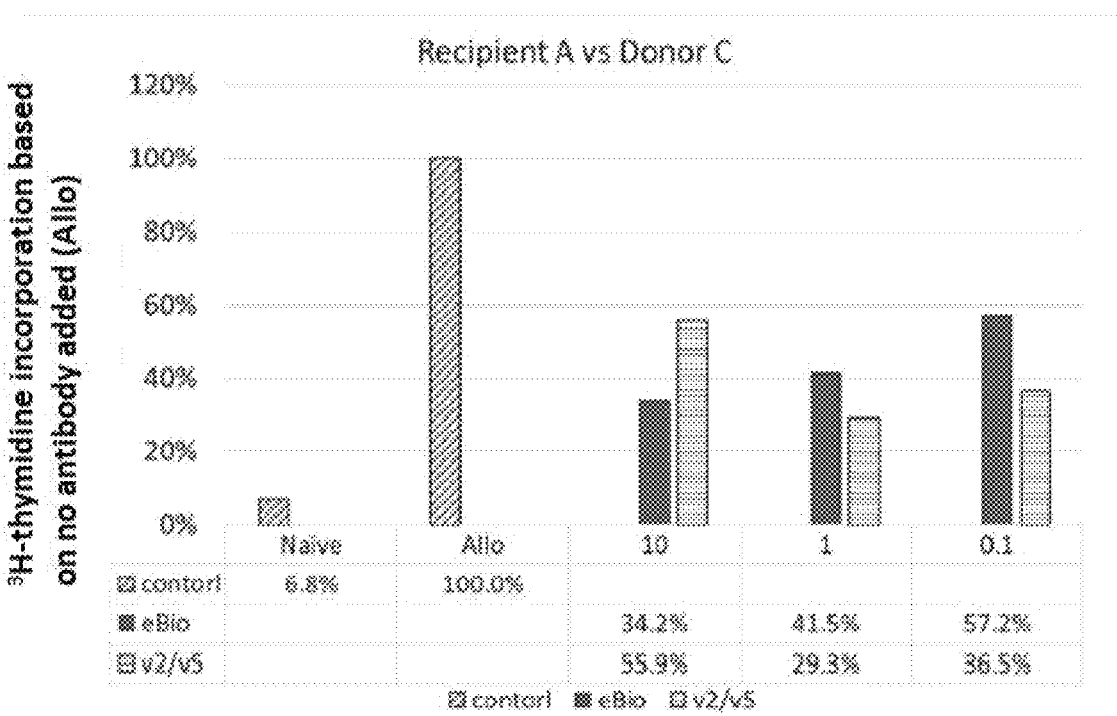
FIG. 1 shows results of a mixed lymphocyte reaction ($^3$H-thymidine incorporation) in the presence of anti-human CD80 and anti-CD86 antibodies (IgG1). Naïve; no donor added, no antibody added, Allo; donor added, no antibody added. 10, 1, and 0.1 are concentrations (μg/ml) of each added antibody. The vertical axis indicates $^3$H-thymidine incorporation, based on no antibody added (Allo).
Figure 1:
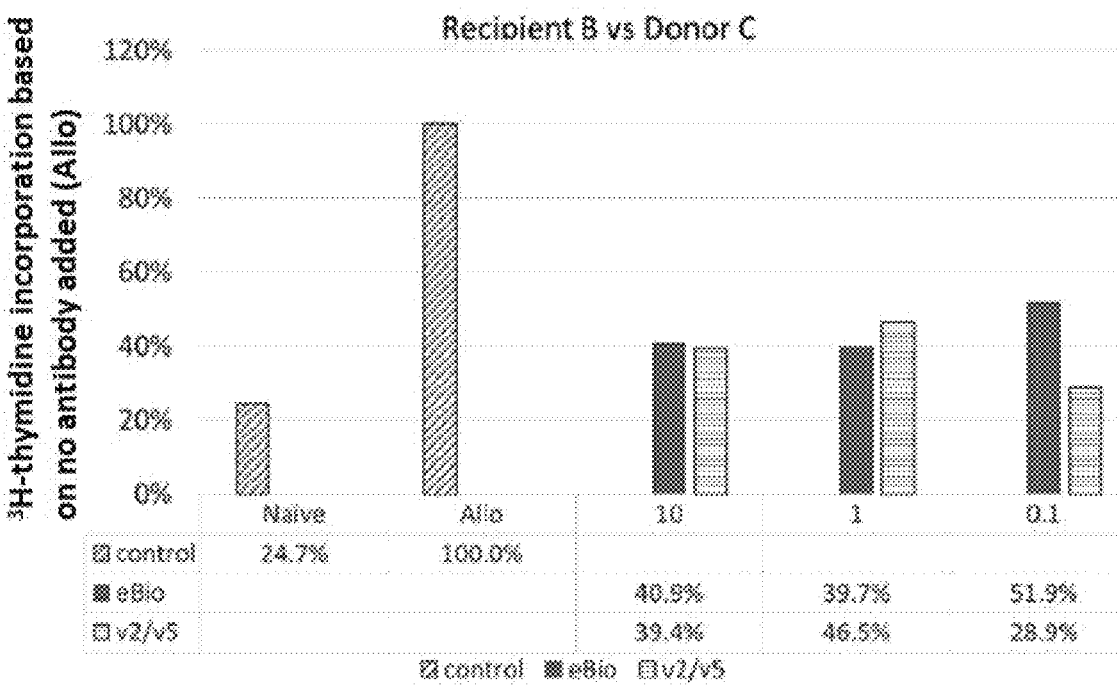

The terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.
(Definitions of Terms)

As used herein, "about" refers to a range of ±10% of the subsequent numerical value.

As used herein, "immune tolerance" refers to a state where a specific immune response to a specific antigen is not exhibited or a specific immune response is suppressed. Immune tolerance can also refer to either or both of a state where an immune cell (especially T cell) does not exhibit a specific immune response to a specific antigen or a specific immune response is suppressed, and a state where a human does not exhibit a specific immune response to a specific antigen or a specific immune response is suppressed. Immune tolerance has drawn attention because elicitation of immune tolerance makes it possible to treat immune rejection or treat allergies. As used herein, "anergy" refers to a state where costimulation is not inputted when an antigen is presented from an antigen presenting cell so that a cell cannot respond upon stimulated under the condition with costimulation the next time. As used herein, "PBMC (or T cell) with immune tolerance induced" is synonymous with "anergic PBMC (or T cell)".

As used herein, "subject" includes domesticated animals (e.g., cows, sheep, cats, dogs, and horses), primates (e.g., humans and non-human primates such as monkeys), rabbits, and rodents (e.g., mice and rats). In a specific embodiment, the subject is a human.

As used herein, "immunostimulation" refers to stimulation applied to cells in the immune system (e.g., macrophage, neutrophil, natural killer (NK) cell, T cell, B cell, etc.) or proliferation of cells in the immune system. Cytokine (e.g., INF) production or cytotoxic activity is induced by stimulation of cells in the immune system.

As used herein, "do not substantially induce the production of a cytokine by immunostimulation" refers to inducing cytokine production of about 20% or less of the amount of cytokines produced by cells (e.g., macrophage, neutrophil, natural killer (NK) cell, T cell, B cell, etc.) derived from a subject in the presence of an antigen and in the absence of the antibody of the present disclosure.

As used herein, "antibody" broadly refers to a molecule or a group thereof that can specifically bind to a specific epitope on an antigen. As used herein, "antibody" can be broadly a full-length antibody (i.e., antibody with an Fc moiety) or an antibody lacking an Fc moiety. An antibody lacking an Fc moiety only needs to be able to bind to an antigen of interest. Examples of such an antibody include, but are not limited to, Fab antibodies, F(ab')$_2$ antibodies, Fab' antibodies, Fv antibodies, and scFv antibodies, and the like. Antibodies also include modified and unmodified antibodies. For modified antibodies, an antibody can be bound to various molecules such as polyethylene glycol. A modified antibody can be obtained by applying a chemical modification to an antibody using a known method.

As used herein, "antibody" narrowly refers to immunoglobulin or a group thereof that can specifically bind to a specific epitope on an antigen. A variant form thereof is referred to as a "variant of an antibody". As used herein, "antibody" can be narrowly a full-length antibody (i.e., antibody with an Fc moiety). A "variant of an antibody" herein can be a variant lacking an Fc moiety of an antibody described above. Therefore, as used herein, an antibody can also be narrowly referred to as a full-length antibody, and a variant of an antibody can also be referred to as a variant of a full-length antibody. A variant lacking an Fc moiety only needs to be able to bind to an antigen of interest. Examples of such a variant include, but are not limited to, Fab antibodies, F(ab')$_2$ antibodies, Fab' antibodies, Fv antibodies, and scFv antibodies, and the like. Variants of an antibody also include modified antibodies and unmodified antibodies. For modified antibodies, an antibody can be bound to various molecules such as polyethylene glycol. A modified antibody can be obtained by applying a chemical modification to an antibody using a known method.

In one embodiment of the present disclosure, "polyclonal antibody" can be generated, for example, by administering an immunogen comprising an antigen of interest to a mammal (e.g., rat, mouse, rabbit, cow, monkey, or the like), avian, or the like to induce the production of a polyclonal antibody specific to an antigen. An immunogen can be administered through one or more immunologic agents, and infusion of an adjuvant when desired. An adjuvant can be used to increase immune responses and can include Freund's adjuvant (complete or incomplete), mineral gel (aluminum hydroxide or the like), surfactant (lysolecithin or the like), or the like. The immunization protocol is known in the art and can be performed by any method that induces an immune response in accordance with the selected host organism ("Tanpakushitsu Jikken Handobukku [*Protein experiment handbook*], Yodosha (2003): 86-91").

In one embodiment of the present disclosure, "monoclonal antibody" encompasses individual antibodies constituting a population that are identical antibodies corresponding to substantially a single epitope, except for antibodies having a mutation that can occur naturally in small amounts. Further, individual antibodies constituting a population may be antibodies that are substantially the same except for antibodies having a mutation that can occur naturally in small amounts. Monoclonal antibodies are highly specific, which are different from common polyclonal antibodies that typically include different antibodies corresponding to different epitopes and/or different antibodies corresponding to the same epitope. In addition to their specificity, monoclonal antibodies are useful in that they can be synthesized from a hybridoma culture which is not contaminated with other immunoglobulins. The description "monoclonal" may indicate a characteristic of being obtained from a substantially homogeneous antibody population. However, such a description does not mean that antibodies must be produced by a specific method. For example, monoclonal antibodies may be prepared by a method similar to the hybridoma method described in "Kohler G, Milstein C., Nature. 1975 Aug. 7; 256 (5517): 495-497". Alternatively, monoclonal antibodies may be prepared by a method similar to the recombinant method described in U.S. Pat. No. 4,816,567. Monoclonal antibodies may also be isolated from a phage antibody library using a method similar to the technology that is described in "Clackson et al., Nature. 1991 Aug. 15; 352 (6336): 624-628." or "Marks et al., J Mol Biol. 1991 Dec. 5; 222(3): 581-597". Monoclonal antibodies may also be prepared by the method described in "Tanpakushitsu Jikken Handobukku [*Protein experiment handbook*], Yodosha (2003): 92-96".

In one embodiment of the present disclosure, "chimeric antibody" is, for example, a variable region of an antibody linked to a constant region of an antibody between xenogenic organisms and can be constructed by a genetic engineering technology. A mouse-human chimeric antibody can be prepared by, for example, the method described in "Roguska et al., Proc Natl Acad Sci USA. 1994 Feb. 1; 91(3): 969-973." For example, the basic method of preparing a mouse-human chimeric antibody links a mouse leader sequence and a variable region sequence in a cloned cDNA with a sequence encoding a human antibody constant region already present in an expression vector of a mammalian cell. After linking the mouse leader sequence and variable region sequence in a cloned cDNA with the sequence encoding a human antibody constant region, the resultant sequence may be linked to a mammalian cell expression vector. A fragment of a human antibody constant region can be from any human antibody H chain constant region and human antibody L chain constant region. Examples of human H chain fragment include Cγ1, Cγ2, Cγ3, or Cγ4, and examples of L chain fragment include Cλ or Cκ.

In one embodiment of the invention, "humanized antibody" is, for example, an antibody, which has one or more CDRs derived from a nonhuman species, a framework region (FR) derived from a human immunoglobulin, and a constant region derived from human immunoglobulin and binds to a desired antigen. Antibodies can be humanized using various approaches known in the art (Almagro et al., Front Biosci. 2008 Jan. 1; 13: 1619-1633). Examples thereof include CDR grafting (Ozaki et al., Blood. 1999 Jun. 1; 93(11): 3922-3930.), Re-surfacing (Roguska et al., Proc Natl Acad Sci USA. 1994 Feb. 1; 91(3): 969-973.), FR shuffle (Damschroder et al., Mol Immunol. 2007 April; 44(11): 3049-3060. Epub 2007 Jan. 22.) and the like. An amino acid residue of a human FR region may be substituted with a corresponding residue from a CDR donor antibody in order to alter (preferably in order to improve) the antigen bond. The FR substitution can be performed by a method that is well known in the art (Riechmann et al., Nature. 1988 Mar. 24; 332 (6162): 323-327.) For example, an FR residue that is important for antigen binding may be identified by modeling an interaction between a CDR and an FR residue. Further, an abnormal FR residue at a specific position may be identified by sequence comparison.

In one embodiment of the invention, "human antibody" is, for example, an antibody in which a region comprising a variable region and constant region of a heavy chain and variable region and constant region of a light chain constituting the antibody is derived from a gene encoding a human immunoglobulin. Examples of main preparation methods include a method using a transgenic mouse for preparing human antibodies, phage display method, and the like. A method using a transgenic mouse for preparing human antibodies produces human antibodies with diverse antigen binding capabilities instead of mouse antibodies if a functional human Ig gene is introduced into an endogenous Ig knockout mouse. Furthermore, this mouse can be immunized to obtain human monoclonal antibodies by a conventional hybridoma method. This can be prepared, for example, by the method described in "Lonberg et al., Int Rev Immunol. 1995; 13(1): 65-93." The phage display method is a system that typically expresses an exogenous gene as a fusion protein such that phage infectivity is not lost on the N-terminus side of a coat protein (g3p, g10p, or the like) of fibrous phage such as an *E. coli* virus M13 or T7. Antibodies can be prepared, for example, by the method described in "Vaughan et al., Nat Biotechnol. 1996 March; 14(3): 309-314".

As used herein, "variant sequence" refers to a sequence with at least one amino acid residue alteration (substitution, addition, or deletion) to the original sequence for an amino acid sequence, and refers to an alteration (substitution, addition, or deletion) of at least one base that would not result in a frame shift for a nucleic acid sequence. A variant sequence has a function similar to the original sequence, which is for example at least 80%, at least 85%, at least 90%, at least 95%, at least 96%, at least 97%, at least 98%, or at least 99% identical to the original sequence. If the original sequence is an antibody, a variant sequence preferably does not have an alternation within a CDR, but can have one or more alternations, preferably 3 or less alternations, more preferably 2 or less alternations, and most preferably one alternation, as long as the binding ability or function of the original antibody is maintained. When an alternation is introduced within a CDR, those skilled in the art can select an appropriate alternation so that the binding ability or function of the original antibody is maintained.

As used herein, "cell derived from a subject" refers to a cell obtained from a subject administered with the composition of the present disclosure or a cell derived from a cell obtained from the subject. As used herein, "antigen derived from a subject" refers to an antigen produced by a subject themselves which induces an immune response, such as an antigen produced by a subject themselves which causes an autoimmune disease in a subject with the autoimmune disease. As used herein, "antigen that is not derived from a subject" refers to an exogenous antigen that can induce an immune response. As used herein, "antigen-containing material that is not derived from a subject" refers to any substance or collection of substances comprising an antigen that is not derived from a subject. Examples thereof include a cell, cell population, tissue, and the like expressing an antigen that is not derived from a subject.

As used herein, "graft rejection" refers to the immune system of a subject attacking, damaging, or destroying a transplanted organ, tissue, or cell in a subject receiving transplantation of the organ, tissue, or cell.

As used herein, "allergy" refers to a hyperactive immune response to an antigen that is not derived from a subject. An antigen that is not derived from a subject, which induces an allergy, is also referred to as an allergen. Examples thereof include, but are not limited to, tick antigen, egg white antigen, milk antigen, wheat antigen, peanut antigen, soybean antigen, buckwheat antigen, sesame antigen, rice antigen, crustacean antigen, kiwi antigen, apple antigen, banana antigen, peach antigen, tomato antigen, tuna antigen, salmon antigen, mackerel antigen, beef antigen, chicken meat antigen, pork antigen, feline dander antigen, insect antigen, pollen antigen, dog dander antigen, fungal antigen, bacterial antigen, latex, hapten, metal, and the like.

As used herein, "autoimmune disease" refers to any disease in which the immune system exerts an undesirable immune response on its own cell, tissue, or organ. Examples of an autoimmune disease include, but are not limited to, rheumatoid arthritis, multiple sclerosis, type 1 diabetes, inflammatory bowel disease (e.g. Crohn's disease or ulcerative colitis), systemic lupus erythematosus, psoriasis, scleroderma, autoimmune thyroid disease, alopecia areata, Graves' disease, Guillain Barre syndrome, celiac disease, Sjogren's syndrome, rheumatic fever, gastritis, autoimmune atrophic gastritis, autoimmune hepatitis, pancreatitis, ovitis, orchitis, uveitis, lens-induced uveitis, myasthenia gravis, primary myxedema, pernicious anemia, autoimmune hemolytic anemia, Addison's disease, scleroderma, Goodpasture syndrome, nephritis (e.g., glomerulonephritis), psoriasis, pemphigus vulgaris, pemphigoid, sympathetic ophthalmia, idiopathic thrombocytopenic purpura, idiopathic leukopenia, Wegener's granulomas, and polymyositis/dermatomyositis.

As used herein, "graft-versus-host" refers to a transplanted organ, tissue, or cell attacking, damaging, or destroying a cell, tissue, or organ of a subject who received transplantation due to an immune response.

As used herein, "immune rejection caused by transplantation of an iPS cell or ES cell, or a cell, tissue, or organ derived from said cells" refers to an immune rejection resulting from an antigen of an iPS cell or ES cell, or an antigen of a cell, tissue, or organ derived from an iPS cell or ES cell.

Preferred Embodiments

The preferred embodiments are described hereinafter. It is understood that the embodiments are exemplification of the present disclosure, so that the scope of the present disclosure is not limited to such preferred embodiments. It is understood that those skilled in the art can refer to the following preferred embodiments to readily make modifications or changes within the scope of the present disclosure. Any of these embodiments can be appropriately combined by those skilled in the art.

As a result of attempting to induce non-immune response (anergy) using an antibody having a human Fc region that inhibits the interaction between CD80 and/or CD86 and CD28, the inventors found that this activates a cell involved in the immune system such as the macrophage, neutrophil, or natural killer (NK) cell and induces the release of a humoral factor such as interleukin or interferon (IFN) responsible for immune responses. The inventors newly discovered that induction of non-immune response (anergy) using an antibody having a human Fc region has a problem of attenuating the effect of immune tolerance because release of these humoral factors induces unpreferable activation of the immune system, which is the opposite of immune tolerance, and found that the effect of immune tolerance can be improved by adjusting the human Fc region.

Specifically, a chimeric antibody that inhibits the interaction between CD80 and/or CD86 and CD28 and induces immune tolerance was prepared by immunizing Balb/c mice with a recombinant/human CD80/CD86-Fc fusion protein, then extracting mRNA from the spleen of the mice, synthesizing a cDNA, selecting a Fab antibody with high affinity to CD80/CD86 identified with a phase display library that was constructed using a gene amplified by RT-PCR, and then imparting a human Fc region by genetic engineering.

To minimize rejection to an antibody used for induction of immune tolerance, the inventors humanized a chimeric antibody with the CDR grafting method developed by Xoma to prepare a humanized antibody (subclass; IgG1). The resulting humanized anti-CD80 antibody and anti-CD86 antibody (subclass; IgG1) were added to a mixed lymphocyte reaction with PBMCs (peripheral blood mononuclear cells) harvested from two volunteers assuming a donor or recipient to evaluate the suppression function upon the same antigen stimulation of the induced cells. Specifically, PBMCs were harvested from one volunteer, irradiated with 30 Gy radiation, and co-cultured for 7 days with PBMCs harvested from another volunteer in the presence of a humanized anti-CD80/CD86 antibody to induce a donor antigen specific anergic cell. The induced cells were added at a certain ratio to mixed lymphocytes from the same recipient and donor, and the ability to suppress division and proliferations of cells with antigen stimulation was measured as the amount of tritium labeled thymidine incorporation. It was confirmed, as a result, that humanized anti-CD80 antibodies and anti-CD86 antibodies significantly suppress the amount of thymidine incorporation, and cells induced by such antibodies have newly acquired a suppression function.

However, when the amount of IFNγ in the supernatant after 7 days of culture was measured, IFNγ was produced upon addition of an antibody, even without a non-antigen stimulation. It was also revealed that IFNγ generally produced upon allo antigen simulation due to addition of PBMCs irradiated with radiation is in the supernatant at almost the same amount after addition of an antibody.

In this regard, the inventors found that a cell inducing immune tolerance, without producing IFNγ, can be obtained by using humanized anti-CD80/CD86 antibodies of subclass IgG2 or IgG4 as a result of diligent study to obtain an antibody that does not induce IFNγ production while maintaining the ability to induce immune tolerance.

(Antibodies)

In one embodiment of the present disclosure, the present disclosure provides an antibody that inhibits an interaction between CD80 and/or CD86 expressed on a surface of a cell, and CD28 expressed on a surface of another cell, wherein the antibody does not substantially induce the production of a cytokine by immunostimulation. The antibody of the present disclosure can be an anti-CD80 antibody and/or anti-CD86 antibody, a bispecific antibody to CD80 and CD86, an anti-CD28 antibody, or a mixture thereof. In some embodiments, an Fc moiety of the antibody can be a moiety that does not substantially induce the production of a cytokine by immunostimulation. In a specific embodiment, a subclass of the antibody of the present disclosure is IgG2 or IgG4. The antibody of the present disclosure whose subclass is IgG2 or IgG4 surprisingly did not induce any production of cytokine due to an immune system cell. Since the antibody used in the present disclosure can result in an undesirable effect by activating a receptor, an antagonistic antibody is preferable.

In some embodiments, an antibody that does not substantially induce the production of a cytokine by immunostimulation can induce cytokine production of about 20% or less, preferably about 10% or less, more preferably about 5% or less, and most preferably about 0% of the amount of cytokines produced by a cell derived from a subject (e.g., macrophage, neutrophil, natural killer (NK) cell, T cell, B cell, or the like) in the absence of the antibody of the present disclosure.

As used herein, "antagonistic (antibody)" is synonymous with an antagonist (antibody), inhibition (antibody), blocking (antibody), or the like, which (is an antibody for antibodies) has the function to inhibit the targeted function or signaling function to attenuate or inactivate the action of a living organism.

As induction of the production of cytokines was unexpectedly suppressed by changing the subclass of an antibody from IgG1 to IgG2 or IgG4 as described above. Although not wishing to be bound by any theory, it is understood that induction of cytokine production is due to an Fc moiety of an IgG1 antibody because the function mediated through the Fc moiety varies among IgG subclasses. Thus, in another embodiment, the antibody of the present disclosure can be an antibody lacking an Fc moiety. Examples of such an antibody include, but are not limited to, an Fab antibody, an F(ab')$_2$ antibody, an Fab' antibody, an Fv antibody, an scFv antibody, and the like.

In some embodiments, the cell expressing CD80 and/or CD86 can be an antigen presenting cell, and the another cell expressing CD28 can be a T cell.

In another aspect of the present disclosure, the antibody of the present disclosure can inhibit an interaction between CD80 and/or CD86 expressed on a cell surface, and CD28 expressed on another cell surface. Whether an interaction between CD80 and/or CD86 expressed on a cell surface and CD28 expressed on another cell surface can be inhibited can be determined by, for example, coimmunoprecipitation. Specifically, these proteins are bound and then immunoprecipitated using an antibody that binds to one of the proteins (bait), and the other immunoprecipitated protein (prey) is measured. If the prey contained in immunoprecipitation is decreased when a candidate antibody is added compared to a control without a candidate antibody, the candidate antibody is determined as inhibiting the binding between the proteins. A prey contained in an immunoprecipitation can be measured by labeling the prey or the like as needed. The amount of prey bound to a carrier can be compared by binding one of the protein (bait) to the carrier using pull-down assay method and contacting the other protein (prey) in the presence/absence of a candidate antibody.

Preferably, the antibody of the present disclosure can inhibit an interaction between CD80 and/or CD86 expressed on an antigen presenting cell surface and CD28 expressed on a T cell surface. Whether a candidate antibody inhibits an interaction between CD80 and/or CD86 expressed on an antigen presenting cell surface and CD28 expressed on a T cell surface can be determined by contacting the antigen presenting cell expressing CD80 and/or CD86 with a T cell expressing CD28 in the presence of a candidate antibody and determining that an interaction between CD80 and/or CD86 expressed on the antigen presenting cell surface and CD28 expressed on the T cell surface is inhibited if the T cell is not activated.

Further, the antibody of the present disclosure is characterized by not promoting cytokine production by human PBMCs. Whether a candidate antibody does not promote cytokine production by a human PBMC can be determined by contacting the candidate antibody with the human PBMC in a medium and measuring the amount of cytokines released in the medium. A candidate antibody with lower/greater amount of cytokines released in the presence of the candidate antibody compared to the amount of cytokines released by a human PBMC in the absence of an antibody is determined as not promoting/promoting cytokine production by a human PBMC. Examples of cytokines include interleukins such as IL-1R, IL-2, IL-4, IL-5, IL-6, IL-8, IL-9, IL-14, IL-15, IL-17, and IL-18; chemokines such as CC, CXC, CX3C, and C; interferons such as IFNα, IFNβ, and IFNγ; and cytotoxic agents such as TNFα. Cytokines are preferably inflammatory cytokines and more preferably IFNγ. Cytokines can be measured using a commercially available kit. For example, IFNγ can be measured using Biolegend's Human IFNγ ELISA MAXTM Deluxe.

Preferably, the antibody of the present disclosure can be contacted with a PBMC together with an antigen or a cell having an antigen on a surface to induce immune tolerance to the antigen. Whether a candidate antibody can induce immune tolerance to an antigen by contacting the antibody with a PBMC together with the antigen or a cell having the antigen on a surface can be determined by contacting the antigen or cell having the antigen on a surface with a PBMC for several days to 7 days in the presence of the candidate antibody, then adding $^3$H-thymidine, and removing the $^3$H-thymidine in culture 16 to 20 hours after adding the $^3$H-thymidine, and then measuring the amount of $^3$H-thymidine incorporation by the PBMC. If the amount of $^3$H-thymidine incorporation by a PBMC is low when the candidate antibody is added compared to a control without deployment of the candidate antibody, the antibody can be determined as capable of inducing immune tolerance to the antibody by contacting the antibody with the PBMC together with an antigen or a cell having an antigen on a surface.

As used herein, "immune tolerance" is a condition where a specific immune response to a specific antigen is not exhibited or a specific immune response is suppressed. Immune tolerance can mean either or both a state where an immune cell (especially a T cell) does not exhibit a specific immune response to a specific antigen or a specific immune response is suppressed, and a state where a human does not exhibit a specific immune response to a specific antigen or a specific immune response is suppressed. As used herein, "anergy" refers to a T cell that can no longer respond even when stimulated under the condition with costimulation the next time due to no input of costimulation when an antigen is presented from an antigen presenting cell. As used herein, "PBMC (or T cell) with immune tolerance induced" and "anergic PBMC (or T cell)" are synonymous.

Preferably, the present disclosure relates to an anti-CD80 antibody and anti-CD86 antibody. The anti-CD80 antibody and anti-CD86 antibody herein specifically binds to CD80 and Cd86, respectively. As used herein, an antibody's "specific" binding refers to the antibody binding at a substantially higher affinity to a protein of interest (CD80 or CD86) than the affinity to other proteins or peptides. In this regard, "binding at a substantially higher affinity" refers to higher affinity to the extent that a specific protein or peptide of interest can be distinctly detected from other proteins or peptides by a desirable measuring apparatus or method. For example, substantially higher affinity can mean about 3-fold or greater, about 4-fold or greater, about 5-fold or greater, about 6-fold or greater, about 7-fold or greater, about 8-fold or greater, about 9-fold or greater, about 10-fold or greater, about 20-fold or greater, about 30-fold or greater, about 40-fold or greater, about 50-fold or greater, or about 100-fold or greater as the intensity (e.g., fluorescence intensity) detected by ELISA or EIA.

Examples of association rate constant (Ka1) in the binding of the antibody of the present disclosure with CD80, CD86, or CD28 include about $1 \times 10^4$ $Ms^{-1}$ or greater, about $1 \times 10^5$ $Ms^{-1}$ or greater, and about $5 \times 10^5$ $Ms^{-1}$ or greater. Examples of dissociation rate constant (Kd1) in the binding of the antibody of the present disclosure with CD80, CD86, or CD28 include about $1 \times 10^{-3}$ $Ms^{-1}$ or less and about $1 \times 10^{-4}$ $Ms^{-1}$ or less. Examples of association constant (KD) in the binding of the antibody of the present disclosure with CD80, CD86, or CD28 include about $1 \times 10^{-8}$ (M) or less, about $5 \times 10^{-8}$ (M) or less, about $1 \times 10^{-9}$ (M) or less, and about $5 \times 10^{-9}$ (M) or less. For the association rate constant (Ka1), dissociation rate constant (Kd1), and association constant (KD) of an antibody herein, BIACORE (GE Healthcare Bio-Sciences KK, BIACORE-X100) can be used according to the manual provided by the manufacturer to immobilize biotinylated CD80, CD86, or CD28 or a cell expressing the same on an SA chip then allowing an antibody to be tested to flow to measure the association rate constant Ka1 and dissociation rate constant Kd1, and using bivalent fitting to measure the association constant KD.

The antibody of the present disclosure can be a polyclonal antibody or a monoclonal antibody, but is preferably a monoclonal antibody. In the present disclosure, "monoclonal antibodies" are antibodies with a uniform structure, reacting to a single antigenic determinant. Furthermore, the antibody of the present disclosure encompasses an antibody having an amino acid sequence of an antibody of a non-human animal and an amino acid sequence of an antibody derived from a human and a human antibody. Examples of antibodies of a non-human animal include antibodies of a mouse, rat, hamster, guinea pig, rabbit, dog, monkey, sheep, goat, camel, chicken, duck, or the like, preferably antibodies of an animal with which a hybridoma can be prepared, and more preferably antibodies of a mouse, rat, or rabbit. Examples of antibodies with an amino acid sequence of an antibody of a non-human animal and an amino acid sequence of an antibody derived from a human include human type chimeric antibodies and humanized antibodies. The "chimeric antibody" described above is a non-human animal derived antibody altered by genetic engineering so that a constant region of an antibody specifically binding to an antigen of interest (CD80, CD86, or CD28) is the same constant region as a human antibody. A chimeric antibody is preferably a human mouse chimeric antibody (see EP Patent Application Publication No. 0125023). A "humanized antibody" is a non-human animal derived antibody altered by genetic engineering so that the primary structure other than the H-chain and L-chain complementarity-determining regions (CDR) of an antibody specifically biding to CD80, CD86, or CD28 is a primary structure corresponding to a human antibody. In this regard, CDR can be defined by one of Kabat et al. ("Sequences of Proteins of Immunological Interest", Kabat, E. et al., U.S. Department of Health and Human Services, 1983), or Chothia et al. (Chothia & Lesk (1987) J. Mol. Biol., 196: 901-917). A "human antibody" is a human antibody, which is a fully-human derived antibody gene expression production. Examples thereof include monoclonal antibodies prepared using a transgenic animal introduced with a gene involved with antibody production of a human (EP Patent Application Publication No. 0546073) and the like. When, for example, the antibody of the present disclosure is used in treatment, prevention, or diagnosis using the antibody by administration into the body, the antibody of the present disclosure is preferably a chimeric antibody of human/non-human animal, humanized antibody, or human antibody.

Preferably, the immunoglobulin class of the antibody of the present disclosure is IgG. The subclass of the antibody of the present disclosure is preferably IgG2 or IgG4. More preferably, the subclass of the antibody of the present disclosure is IgG4. Alternatively, the subclass of the antibody of the present disclosure is preferably IgG2. The antibody of the present disclosure can be a monospecific, bispecific (bispecific antibody), trispecific (trispecific antibody) (e.g., WO 1991/003493), tetraspecific (tetraspecific antibody), or greater multi-specific (multi-antigen specific).

In one embodiment, the antibody of the present disclosure has CDRH3 of the amino acid sequence set forth in SEQ ID NO: 27 or SEQ ID NO: 33. Preferably, the antibody of the present disclosure has CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, or CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33. More preferably, the antibody of the present disclosure has CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, and CDRL1 of the amino acid sequence set forth in SEQ ID NO: 28, CDRL2 of the amino acid sequence set forth in SEQ ID NO: 29, and CDRL3 of the amino acid sequence set forth in SEQ ID NO: 30, or CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33 and CDRL1 of the amino acid sequence set forth in SEQ ID NO: 34, CDRL2 of the amino acid sequence set forth in SEQ ID NO: 35, and CDRL3 of the amino acid sequence set forth in SEQ ID NO: 36.

In one embodiment, the antibody of the present disclosure can be an antibody, or a variant thereof, having a heavy chain with the amino acid sequence set forth in SEQ ID NO: 38 or 42 or a variant sequence thereof, and a light chain with the amino acid sequence set forth in SEQ ID NO: 40 or 44 or a variant sequence thereof. Preferably, the antibody of the present disclosure can be an antibody, or a variant thereof, comprising (a) a VH comprising CDRH1 of the amino acid sequence set forth in SEQ ID NO: 53 or a variant sequence thereof, CDRH2 of the amino acid sequence set forth in SEQ ID NO: 54 or a variant sequence thereof, and CDRH3 of the amino acid sequence set forth in SEQ ID NO: 55 or a variant sequence thereof, and a VL comprising CDRL1 of the amino acid sequence set forth in SEQ ID NO: 56 or a variant sequence thereof, CDRL2 of the amino acid sequence set forth in SEQ ID NO: 57 or a variant sequence thereof, and CDRL3 of the amino acid sequence set forth in SEQ ID NO: 58 or a variant sequence thereof, or (b) a VH comprising CDRH1 of the amino acid sequence set forth in SEQ ID NO: 59 or a variant sequence thereof, CDRH2 of the amino acid sequence set forth in SEQ ID NO: 60 or a variant sequence thereof, and CDRH3 of the amino acid sequence set forth in SEQ ID NO: 61 or a variant sequence thereof, and a VL comprising CDRL1 of the amino acid sequence set forth in SEQ ID NO: 62 or a variant sequence thereof, CDRL2 of the amino acid sequence set forth in SEQ ID NO: 63 or a variant sequence thereof, and CDRL3 of the amino acid sequence set forth in SEQ ID NO: 64 or a variant sequence thereof. In a specific embodiment, the antibody can be an antibody, or a variant thereof, comprising (a) a VH having the amino acid sequence set forth in SEQ ID NO: 46 or a variant sequence thereof and a VL having the amino acid sequence set forth in SEQ ID NO: 48 or a variant sequence thereof, or (b) a VH having the amino acid sequence set forth in SEQ ID NO: 50 or a variant sequence thereof and a VL having the amino acid sequence set forth in SEQ ID NO: 52 or a variant sequence thereof. A variant sequence preferably does not comprise an alternation within the CDRs (amino acid substitution, addition, or deletion), but can comprise several alterations (3 or less, 2 or less, preferably 1 or less) within each CDR, as long as the ability to bind and/or function of an antibody before the alteration is maintained. Preferably, a variant sequence can have at least 90% identity to the original sequence.

In another aspect, the antibody of the present disclosure relates to an antibody having a VH with the amino acid sequence set forth in SEQ ID NO: 18 or SEQ ID NO: 22. Preferably, the antibody of the present disclosure has a VH with the amino acid sequence set forth in SEQ ID NO: 18 and a VL with the amino acid sequence set forth in SEQ ID NO: 20, or a VH with the amino acid sequence set forth in SEQ ID NO: 22 and a VL with the amino acid sequence set forth in SEQ ID NO: 24.

Furthermore, the present disclosure relates to an antibody having a VH with an amino acid sequence encoded by a nucleic acid sequence that hybridizes, under a stringent condition, with a nucleic acid sequence encoding the amino acid sequence of SEQ ID NO: 18 or SEQ ID NO: 22. Preferably, the present disclosure relates to an antibody having a VH with an amino acid sequence encoded by a nucleic acid sequence that hybridizes, under a stringent condition, with a nucleic acid sequence encoding the amino acid sequence of SEQ ID NO: 18, and a VL with an amino acid sequence encoded by a nucleic acid sequence that hybridizes, under a stringent condition, with a nucleic acid sequence encoding the amino acid sequence of SEQ ID NO: 20, or an antibody having a VH with an amino acid sequence encoded by a nucleic acid sequence that hybridizes, under a stringent condition, with a nucleic acid sequence encoding the amino acid sequence of SEQ ID NO: 22, and a VL with an amino acid sequence encoded by a nucleic acid sequence that hybridizes, under a stringent condition, with a nucleic acid sequence encoding the amino acid sequence of SEQ ID NO: 24. As used herein, hybridizing under a stringent condition means hybridizing under a hybridization condition that is generally used by those skilled in the art. Whether a sequence hybridizes can be determined by the method described in, for example, Molecular Cloning, a Laboratory Manual, Fourth Edition, Cold Spring Harbor Laboratory Press (2012), Current Protocols in Molecular Biology, Wiley Online Library, or the like. For example, a hybridization condition can be a condition for hybridizing at 42° C. in 6×SSC (0.9M NaCl, 0.09M trisodium citrate) or 6×SSPE (3M NaCl, 0.2M NaH2PO4, 20 mM EDTA-2Na, pH 7.4) and then washing at 42° C. in 0.5×SSC.

The present disclosure also comprises an antibody having a VH with an amino acid sequence with 80% or greater identity to the amino acid sequence of SEQ ID NO: 18 or SEQ ID NO: 22. Preferably, the antibody of the present disclosure has a VH with an amino acid sequence with 80% or greater identity to the amino acid sequence of SEQ ID NO: 18 and a VL with an amino acid sequence with 80% or greater identity to the amino acid sequence of SEQ ID NO: 20, or a VH with 80% or greater identity to the amino acid sequence of SEQ ID NO: 22 and a VL with an amino acid sequence with 80% or greater identity to the amino acid sequence of SEQ ID NO: 24. Identity of amino acid sequences refers to a ratio (%) of the numbers of amino acids of the same type between two types of proteins in the range of amino acid sequence targeted for comparison, and can be determined using a known program such as BLAST or FASTA. The identity described above can be identity that is higher than 80% or greater, such as identity of 85% or greater, 90% or greater, 95% or greater, 98% or greater, or 99% or greater.

An antibody having the VH described above with an amino acid sequence encoded by a nucleic acid sequence that hybridizes under a stringent condition, or an antibody having an amino acid sequence with 80% or greater identity preferably has the CDR sequence described above.

As a more specific example, the present disclosure comprises an antibody having a heavy chain with the amino acid sequence set forth in one SEQ ID NO. selected from SEQ ID NO: 2, SEQ ID NO: 6, SEQ ID NO: 10, and SEQ ID NO: 14. Preferably, the antibody of the present disclosure has a heavy chain with the amino acid sequence set forth in SEQ ID NO: 2 and a light chain with the amino acid sequence set forth in SEQ ID NO: 4, a heavy chain with the amino acid sequence set forth in SEQ ID NO: 6 and a light chain with the amino acid sequence set forth in SEQ ID NO: 8, a heavy chain with the amino acid sequence set forth in SEQ ID NO: 10 and a light chain with the amino acid sequence set forth in SEQ ID NO: 12, or a heavy chain with the amino acid sequence set forth in SEQ ID NO: 14 and a light chain with the amino acid sequence set forth in SEQ ID NO: 16.

In a preferred embodiment, an antibody can comprise (a) a VH comprising CDRH1 of the amino acid sequence set forth in SEQ ID NO: 25, CDRH2 of the amino acid sequence set forth in SEQ ID NO: 26, and CDRH3 of the amino acid sequence set forth in SEQ ID NO: 27, and a VL comprising CDRL1 of the amino acid sequence set forth in SEQ ID NO: 28, CDRL2 of the amino acid sequence set forth in SEQ ID NO: 29, and CDRL3 set forth in SEQ ID NO: 30, or (b) a VH comprising CDRH1 of the amino acid sequence set forth in SEQ ID NO: 31, CDRH2 of the amino acid sequence set forth in SEQ ID NO: 32, and CDRH3 of the amino acid sequence set forth in SEQ ID NO: 33, and a VL comprising CDRL1 of the amino acid sequence set forth in SEQ ID NO: 34, CDRL2 of the amino acid sequence set forth in SEQ ID NO: 35, and CDRL3 set forth in SEQ ID NO: 36. In another preferred embodiment, an antibody can comprise (a) a VH having the amino acid sequence set forth in SEQ ID NO: 18 or a variant sequence thereof, and a VL having the amino acid sequence set forth in SEQ ID NO: 20 or a variant sequence thereof, or (b) a VH having the amino acid sequence set forth in SEQ ID NO: 22 or a variant sequence thereof, and a VL having the amino acid sequence set forth in SEQ ID NO: 24 or a variant sequence thereof. A variant sequence preferably does not comprise an alteration (amino acid substitution, addition, or deletion) within a CDR, but can comprise an alternation of several alternations (3 or less, 2 or less, preferably 1 or less) within each CDR, as long as the ability to bind and/or function of an antibody before the alteration is maintained. Preferably, a variant sequence can have at least 90% identity to the original sequence.

The antibody of the present disclosure can be prepared by immunizing a non-human animal with an immune response, preferably a non-human animal (e.g., MRL/lpr mouse) with an immune response (autoantibody) to itself due to hyperimmunization, with a CD80, CD86, or CD28 protein or an extracellular domain thereof, or a cell expressing CD80, CD86, or CD28 as an immunogen, together with an immunostimulant (e.g., mineral oil or aluminum precipitate and heated dead bacteria or lipopolysaccharide, Freund's complete adjuvant, Freund's incomplete adjuvant, or the like) as needed. An immunized animal is not particularly limited, as long as it is an animal for which a hybridoma can be prepared, such as a mouse, rat, hamster, guinea pig, rabbit, dog, monkey, sheep, goat, chicken, or duck, but is preferably a mouse or a rat, more preferably a mouse, and most preferably an MRL/lpr mouse. An immunogen can be administered to an animal by subcutaneous injection, intraperitoneal injection, intravenous injection, intradermal injection, intramuscular injection, or foot sole injection of $1\times10^6$ cells once or several times at a suitable interval (generally, one immunization every 1 to 6 weeks for a total of about 2 to 10 times). After 1 to 2 weeks from the last immunization, blood is collected from the eye socket or caudal vein of the immunized animal to measure the antibody titer using the serum thereof. The antibody of the present disclosure can be obtained by purification from the serum of an animal exhibiting sufficient antibody titer.

A monoclonal antibody can be obtained by culturing a hybridoma obtained by fusing an antibody producing cell obtained from an immunized animal that has been immunized through the method described above with a myeloma cell. Examples of the fusion method include the method of Milstein et al. (Galfre, G. & Milstein, C. (1981) Methods Enzymol., 73:3-46). An antibody producing cell to be used can be harvested from the spleen, pancreas, lymph node, or peripheral blood of a mouse or rat, which is immunized by the method described above and has serum exhibiting sufficient antibody titer. A myeloma cell to be used is not particularly limited, as long as it is a cell that is derived from a mammal such as a mouse, rat, guinea pig, hamster, rabbit, or human and can proliferate in vitro. Examples of such a cell include P3-X63Ag8 (X63) (Nature, 256, 495, 1975), P3/NS1/1-Ag4-1 (NS1) (Eur. J. Immunol., 6, 292, 1976), P3X63Ag8U1 (P3U1) (Curr. Top. Microbiol. Immunol., 81, 1, 1978), P3X63Ag8.653 (653) (J. Immunol., 123, 1548, 1979), Sp2/0-Ag14 (Sp2/O) (Nature, 276, 269, 1978), Sp2/O/FO-2 (FO-2) (J. Immunol. Methods, 35, 1, 1980), SP2ab, and the like. The cell is preferably a cell derived from an animal of the same species as the antibody producing cell, and more preferably a cell derived from an animal of the same phylogenic tree as the antibody producing cell.

After culture, the culture supernatant is collected, and a clone binding to CD80, CD86, or CD28 is selected through ELISA using a CD80, CD86, or CD28 protein or an extracellular domain thereof, or a cell expressing CD80, CD86, or CD28. A cell producing monoclonal antibody can be obtained by repeating limiting dilution 1 to 5 times on the selected clone to prepare a single cell.

Alternatively, an antibody binding to CD80, CD86, or CD28 can be obtained, for example, by utilizing an antibody phage library (Tomizuka et al., Nature Genet., 15, 146-156 (1997)). When utilizing an antibody phage library, a desired clone can be obtained by, for example, immobilizing a CD80, CD86, or CD28 protein or an extracellular domain thereof, or a cell expressing CD80, CD86, or CD28 to a solid phase, reacting this with a phage library, washing and removing unbound phage, and then collecting the bound phage (panning).

Alternatively, this can be obtained by screening an antibody with high specificity to CD80, CD86, or CD28 in accordance with the method described above from antibodies obtained by designing the amino acid sequence of an antibody of interest or an immune responsive fragment thereof by referring to the amino acid sequence described herein, preparing a DNA encoding the designed amino acid sequence, incorporating the DNA into an expression vector, and introducing and expressing said vector in a suitable host cell.

When the antibody of the present disclosure is a human type chimeric antibody, the antibody can be obtained by preparing a DNA encoding VH and VL of a non-human animal monoclonal antibody, binding this with a constant region cDNA of a human immunoglobulin and integrating this into an expression vector, and introducing and expressing the vector in a suitable host cell (Morrison, S. L. et al., Proc. Natl. Acad. Sci. USA, 81, 6851-6855, 1984).

When the antibody of the present disclosure is a humanized antibody, the antibody can be obtained by constructing a DNA encoding a V region prepared by transplanting an amino acid sequence encoding a CDR of a VH and VL of a non-human animal monoclonal antibody into a Framework Region (FR) of a VH and VL of a human antibody, binding the constructed DNA with a constant region cDNA of a human derived immunoglobulin and integrating this into an expression vector, and introducing and expressing the vector into a suitable host cell (see L. Rieohmann et al., Nature, 332, 323, 1988: Kettleborough, C. A. et al., Protein Eng., 4, 773-783, 1991; Clark M., Immunol. Today., 21, 397-402, 2000). A CDR of a non-human animal monoclonal antibody can be obtained by comparing an amino acid sequence predicted from a DNA sequence encoding a VH and VL of a non-human animal monoclonal antibody obtained by the method described above with the full amino acid sequences of the VH and VL of a known antibody. The amino acid sequences of a known antibody can be obtained from the amino acid sequences of antibodies that are registered in a database such as a protein data bank. An FR of a humanized antibody is not particularly limited as long as an antibody after transplantation attains the effect of the present disclosure, but is preferably an FR of a human antibody with a three-dimensional structure where the variable region (hereinafter, referred to as the "V region") of the humanized antibody is similar to the V region of a non-human animal monoclonal antibody from which the CDR is derived, or a human antibody FR with high homology to the amino acid sequence of an FR of a non-human animal monoclonal antibody to be used. Some of the amino acids constituting an FR derived from a human antibody (particularly amino acids positioned in the vicinity of a CDR three dimensionally) can be substituted with an FR sequence of a non-human animal monoclonal antibody from which a CDR is derived as needed in a humanized antibody (see Queen et al., U.S. Pat. No. 5,585,089). A DNA sequence encoding a V region of a humanized antibody to be used is designed as a DNA sequence corresponding to an amino acid sequence prepared by binding an amino acid sequence of a CDR of a non-human animal monoclonal antibody with an amino acid sequence of an FR of a human antibody. A DNA encoding a V region of a humanized antibody can be prepared by a method that is well known to those skilled in the art based on a designed DNA sequence.

For example, a human antibody can be obtained by utilizing a human antibody phage library or a human antibody producing transgenic mouse (Tomizuka et al., Nature Genet., 15, 146-156 (1997)). When utilizing a human antibody phage library, a desired clone can be obtained by, for example, binding a CD80, CD86, or CD28 protein or an extracellular domain thereof, or a cell expressing CD80, CD86, or CD28 to a solid phase, reacting this with a phage library, washing and removing unbound phage, and then collecting the bound phage (panning). A human antibody producing transgenic mouse is a mouse produced by introducing an Ig gene of a human antibody into an endogenous immunoglobulin (Ig) gene knockout mouse. A human antibody that specifically recognizes CD80, CD86, or CD28 can be obtained by immunizing an antigen protein in accordance with the antibody preparation method of the present disclosure described above, while using a human antibody producing transgenic mouse as an immunized animal.

(Nucleic Acid Molecule/Vector/Host Cell)

In another aspect, the present disclosure relates to a nucleic acid molecule having a polynucleotide encoding the antibody of the present disclosure described above. For example, the nucleic acid molecule of the present disclosure comprises the nucleotide sequence set forth in SEQ ID NO: 17 or SEQ ID NO: 21 as a VH. In another aspect, the nucleic acid molecule of the present disclosure comprises the nucleotide sequence set forth in SEQ ID NO: 19 or SEQ ID NO: 23 as a VL. As a more specific example, the nucleic acid molecule of the present disclosure comprises a polynucleotide encoding a VH having the nucleotide sequence set forth in any one selected from SEQ ID NOs: 1, 5, 9, and 13 and a polynucleotide encoding a VL with the nucleotide sequence set forth in any one selected from SEQ ID NOs: 3, 7, 11, and 15. The nucleic acid molecule of the present disclosure can have a nucleic acid sequence that hybridizes under a stringent condition with the SEQ ID NO. described above. Furthermore, the present disclosure encompasses a vector having said nucleic acid molecule. Such a vector is not particularly limited, as long as it is a vector that can be utilized in the expression of an antibody. A suitable viral vector, a plasmid vector, or the like can be selected in accordance with the host that is used. In another aspect, the present disclosure relates to a host cell comprising said vector. The host cell is not particularly limited as long as it is a host cell that can be utilized in the expression of an antibody. Examples thereof include mammalian cells (mouse cells, rat cells, rabbit cells, human cells, and the like) yeast, and microorganisms (*E. coli* and the like). The present disclosure comprises a method of manufacturing the antibody of the present disclosure, comprising culturing the host cell described above. A medium culturing method can be appropriately determined by well-known means of those skilled in the art in accordance with the host cell that is used.

The nucleic acid of the present disclosure can be obtained by cloning from a hybridoma producing an antibody obtained above, or designing an appropriate nucleic acid sequence based on the amino acid sequence of the antibody obtained above or an immune responsive fragment thereof. The vector of the present disclosure can be obtained by incorporating the resulting nucleic acid into a vector suitable for expression as appropriate. The vector of the present disclosure can comprise a region that is required for expression (promotor, enhancer, terminator, or the like) in addition to the nucleic acid of the present disclosure. The host cell of the present disclosure can be obtained by introducing the vector of the present disclosure into a suitable cell line (e.g., animal cell, insect cell, plant cell, yeast, or microorganism such as *E. coli*).

(Composition)

In one embodiment of the present disclosure, the present disclosure provides a composition for preparing a cell having immune tolerance induced, comprising at least one of the antibodies described herein. In one embodiment of the present disclosure, a composition can comprise an anti-CD80 antibody, an anti-CD86 antibody, an anti-CD28 antibody, a bispecific antibody to CD80 and CD86, or any combination thereof. Rejection due to organ transplantation can be reduced by, for example, administering to cell having immune tolerance induced to a subject receiving organ transplantation. A cell having immune tolerance induced can be a cell derived from a subject (recipient) or a donor, or a mixture thereof. The composition of the present disclosure surprisingly does not substantially induce release of cytokines due to a cytokine producing cell (e.g., macrophage, neutrophil, or natural killer (NK) cell). Since cytokines attenuate immune tolerance, it is advantageous that release of cytokines is not induced.

In another aspect, the present disclosure relates to a medical composition comprising the antibody described herein. In one example, the medical composition of the present disclosure comprises an anti-CD80 antibody, an anti-CD86 antibody, an anti-CD28 antibody, or a bispecific antibody to CD80 and CD86. The medical composition of the present disclosure can be used to induce immune tolerance. Throughout the entire specification, "to induce immune tolerance" includes cases of use, for example, to induce immune tolerance to a transplanted organ, i.e., to suppress excessive immune responses to a causative agent that becomes an immunogen in a patient with an autoimmune disease or allergic disease to alleviate or treat a symptom of such diseases in order to suppress rejection in organ transplantation. In another embodiment, the pharmaceutical composition of the present disclosure is used to prepare a cell having immune tolerance induced.

As used herein, "organ" to be transplanted in "organ transplantation" is not particularly limited. Examples thereof include a heart, kidney, lung, pancreas, esophagus, stomach, small intestine, large intestine, skin, nerve, blood, blood cells including immune system cells, bone, cartilage, blood vessel, cornea, eye ball, bone marrow, and liver. As used herein, "organ" includes a part of an organ and cells constituting an organ in addition to the entirety or a mass of an organ. For example, transplanted organs also include myocardial cells, corneal cells, and the like. Organ transplantation also includes transplantation of an organ made using heterologous stem cells in regenerative medicine or the like into a patient in addition to transplantation of an organ of another individual into a patient.

The antibody of the present disclosure can be used as a medical composition by purifying and then formulating in accordance with a conventional method as needed. The present disclosure also comprises use of the antibody of the present disclosure for the manufacture of a medical composition for inducing immune tolerance. Alternatively, the present disclosure comprises use of the antibody of the present disclosure for inducing immune tolerance. Furthermore, the present disclosure relates to a method of inducing immune tolerance, comprising adding or administering the antibody of the present disclosure. For example, the present disclosure comprises a method of suppressing rejection in organ transplantation, comprising administering the antibody of the present disclosure to a patient receiving organ transplantation, a method of treating an autoimmune disease or allergic disease, comprising administering the antibody of the present disclosure to a patient with an autoimmune disease or allergic disease, and a method of suppressing rejection in transplantation of an iPS cell or ES cell or a cell, tissue, or organ derived (differentiated) therefrom, comprising administering the antibody of the present disclosure to a patient receiving transplantation of an iPS cell or ES cell or a cell, tissue, or organ derived (differentiated) therefrom.

Examples of cells, tissue, or organ derived (differentiated) from iPS cells or ES cells include, but are not limited to, nervous cells or tissue, corneal cells or tissue, myocardial cells or tissue, liver cells or tissue, cartilage cells or tissue, skin cells or tissue, kidney cells or tissue, and the like. In a preferred embodiment, cells, tissue, or organ derived (differentiated) from iPS cells or ES cells include nervous cells or tissue, myocardial cells or tissue, cartilage cells or tissue, and skin cells or tissue.

The medical composition of the present disclosure can be used through direct administration to a patient, or through contacting the composition with a PBMC harvested from a patient whose immune tolerance is to be induced, together with an antigen of interest inducing immune tolerance ex vivo to prepare an immune cell that is anergic to the antigen.

When the medical composition of the present disclosure is directly administered to a patient, any oral or parenteral formulation can be used. Examples of a composition for parenteral administration include eye drops, injections, nasal drops, suppositories, patches, ointments, and the like. The composition is preferably an injection. Examples of the dosage forms of the medical composition of the present disclosure include a liquid agent and a lyophilized formulation. When the medical composition of the present disclosure is used as an injection, an additive, e.g., a solubilizing agent such as propylene glycol or ethylenediamine, buffer such as phosphate, tonicity agent such as sodium chloride or glycerine, stabilizer such as sulfite, preservative such as phenol, or analgesic such as lidocaine, can be added as needed (see "Japanese Pharmaceutical Excipients Directory", Yakuji Nippo, Limited, "Handbook of Pharmaceutical Excipients Fifth Edition" APhA Publications). When the medical composition of the present disclosure is used as an injection, examples of a storage container include an ampule, vial, prefilled syringe, pen-shaped injection cartridge, IV bag, and the like.

For example, the medical composition of the present disclosure (therapeutic drug or preventive drug) can be utilized as an injection. The dosage form thereof includes intravenous injection, subcutaneous injection, intradermal injection, intramuscular injection, intravitreous injection, intravenous drip injection, and the like. Such injections can be prepared in accordance with a known method, for example, by dissolving, suspending, or emulsifying the antibody described above in an aseptic aqueous or oily solution that is generally used in injection. For example, tonicity solution comprising saline, glucose, sucrose, mannitol, or other adjuvant or the like can be used as an aqueous solution for injection, and can be used in conjunction with a suitable solubilizing agent such as alcohol (e.g., ethanol), polyalcohol (e.g., propylene glycol or polyethylene glycol), anionic surfactant [e.g., polysorbate 80, polysorbate 20, HCO-50 (polyoxyethylene (50 mol) adduct of hydrogenated castor oil)] or the like. For example, sesame oil, soybean oil or the like can be used as an oily solution, which may be used concomitantly with benzyl benzoate, benzyl alcohol, or the like as a solubilizing agent. The prepared injection is generally filled in a suitable ampule, vial, or syringe. A suitable excipient can be added to the antibody of the present disclosure or an immune responsive fragment thereof to prepare a lyophilized formulation, which is dissolved in injection water, saline, or the like when needed as an injection solution. While oral injection of a protein such as an antibody is generally considered difficult due to decomposition by digestive organs, oral administration may be possible by creativity and ingenuity in the dosage form, such as an antibody fragment or modified antibody fragment. Examples of orally administered formulations include capsules, tablets, syrup, granules, and the like.

The medical composition of the present disclosure is suitably prepared into a dosage form in a dosing unit that matches the dosage of an active ingredient. Exemplary dosage form in a dosing unit includes an injection (ampule, vial, or prefilled syringe). Generally, 5 to 500 mg, 5 to 100 mg, or 10 to 250 mg of the antibody of the present disclosure or an immune responsive fragment thereof can be contained per dosage form in a dosing unit.

Administration of the medical composition of the present disclosure can be topical or systemic. The administration method is not particularly limited. The composition is administered parenterally or orally as described above. Examples of parenteral routes of administration include intraocular, subcutaneous, intraperitoneal, blood (intravenous or intra-arterial), or spinal fluid injection, drop, and the like, and is preferably administration into the blood. The medical composition of the present disclosure (therapeutic drug or preventive drug) can be temporarily administered, or continuously or intermittently administered. For example, the administration can be continuous administration for 1 minute to 2 weeks.

The dosage of the medical composition of the present disclosure is not particularly limited, as long as it is a dosage attaining a desired therapeutic or preventive effect. The dosage can be appropriately determined depending on the symptom, sex, age, or the like. The dosage of the medical composition of the present disclosure can be determined, for example, with the degree of induction of immune tolerance as an indicator. For example, as a single dose of an active ingredient of the medical composition of the present disclosure, it is advantageous to administer generally about 0.01 to 20 mg/kg body weight, preferably about 0.1 to 10 mg/kg body weight, and still more preferably about 0.1 to 5 mg/kg body weight about 1 to 10 times a month and preferably about 1 to 5 times a month by intravenous injection. An amount corresponding thereto can be administered for other parenteral or oral administration. If the symptom is particularly severe, the amount or the number of administrations can be increased in accordance with the symptom.

When the medical composition of the present disclosure is contacted with a PBMC harvested from a patient whose immune tolerance is to be induced, together with an antigen of interest inducing immune tolerance ex vivo to prepare an immune cell that is anergic to the antigen, the composition can be prepared in a form such as liquid, powder, tablet, gel, or granule in accordance with the composition for administration described above.

(Immune Tolerance Induced Cells)

In another aspect, the present disclosure provides a cell having immune tolerance induced by the antibody described herein. Immune tolerance can be induced by mixing a cell derived from a subject with an antigen that is not derived from the subject or an antigen containing material. In still another aspect of the present disclosure, the present disclosure provides a method for manufacturing a cell for treating or preventing a disease, disorder, or condition caused by an antigen that is not derived from a subject, comprising mixing the antibody described herein, a cell derived from a subject, and an antigen that is not derived from the subject or an antigen containing material (e.g., cell). The disease, disorder, or condition can be selected from the group consisting of graft rejection, allergy, autoimmune disease, graft-versus-host disease, and immune rejection caused by transplantation of an iPS cell or an ES cell and a cell, tissue, or organ derived from said cells.

In an embodiment where the disease or the like targeted by the present disclosure is graft rejection, an anergic cell can be induced by mixing the antibody described above with a recipient derived cell (PBMC or splenocyte) and a donor derived antigen or a donor derived antigen containing material. A donor derived antigen containing material can be a PBMC, splenocyte, or a cell derived from an organ to be transplanted.

In an embodiment where the disease targeted by the present disclosure or the like is allergy, an anergic cell can in induced by mixing the antibody described above with a subject derived cell (PBMC or splenocyte) and an allergy inducing antigen that is not derived from the subject.

In an embodiment where the disease targeted by the present disclosure or the like is an autoimmune disease, an anergic cell can in induced by mixing the antibody described above with a subject derived cell (PBMC or splenocyte) and a subject derived antigen that is the cause of the autoimmune disease.

In an embodiment where the disease targeted by the present disclosure or the like is a graft-versus-host disease, an anergic cell can be induced by mixing the antibody described above with a PBMC or splenocyte of a donor providing the graft and recipient derived antigen or a material containing the antigen. The material containing an antigen derived from a recipient can be a PBMC, splenocyte, a cell around a site where an organ is transplanted, or a cell derived therefrom.

In an embodiment where the disease targeted by the present disclosure or the like is immune rejection caused by transplantation of an iPS cell or an ES cell and a cell, tissue, or organ derived from said cells, an anergic cell can be induced by mixing the antibody described above with a subject derived cell (PBMC or splenocyte) and a cell differentiated from an iPS cell or ES cell used in transplantation.

Therapeutic examples of a disease or the like according to the present disclosure are shown below, but are not limited thereto.

(Allergy and Autoimmune Disease)

For allergy and autoimmune diseases, a macrophage obtained from the peripheral blood of a patient is differentiated into a dendritic cell (macrophage derived dendritic cell) with high antigen presenting ability by a conventional method. The cell after irradiation of radiation (γ rays) is made to present an antigen that is the cause of hyper-reaction in allergy or autoimmune disease, and co-cultured for 1 to 2 weeks with a T cell group contained form the same patient peripheral blood in the presence of an anti-CD80 antibody and/or anti-CD86 antibody to obtain an anergic cell that is specific to the antigen causing the allergy or autoimmune disease. The anergic cell is administered to a patient to induce immune tolerance specific to the antigen causing the allergy or autoimmune disease for use in the prevention or treatment of allergy and autoimmune disease. The number of dosings can be multiple, depending on whether the dosing is preventive therapy or treatment, and various conditions such as the severity of symptoms.

(Graft-Versus-Host Disease)

For graft-versus-host disease, in contrast to the treatment of graft rejection, a cell that can be the cause of graft-versus-host disease such as a PBMC or T cell of a donor providing a graft is co-cultured for 1 to 2 weeks with a PBMC derived from a host irradiated with radiation (γ rays) or other cells in the presence of an anti-CD80 antibody and/or anti-CD86 antibody to obtain an anergic cell that is specific to a host. Administration of such an anergic cell to a host suppresses responses to a host by a graft causing the graft-versus-host disease (and induces immune tolerance) to prevent or treat graft-versus-host disease. The number of dosings can be multiple, depending on whether the dosing is preventive therapy or treatment, and various conditions such as the tissue to be transplanted, the size thereof, or the severity of symptoms.

(Immune Rejection Caused by Transplantation of an iPS Cell or an ES Cell and a Cell, Tissue, or Organ Derived from Said Cells)

In applications to treatment using an iPS cell or ES cell, a dendritic cell or a cell used in transplantation differentiated from an iPS cell or ES cell is irradiated with radiation (γ rays), and the cell is co-cultured for 1 to 2 weeks with a PBMC or T cell group of a patient receiving transplantation in the presence of an anti-CD80 antibody and/or anti-CD86 antibody to obtain an anergic cell that is specific to a cell differentiated from an iPS cell or ES cell. Administration of such an anergic cell to a host induces immune tolerance that is specific to an iPS cell or ES cell derived transplanted cell, tissue, and organ and prevent and treat rejection thereto. The number of dosings can be multiple, depending on whether the dosing is preventive therapy or treatment, and various conditions such as the tissue to be transplanted, the size thereof, or the severity of symptoms.

In a specific embodiment, the present disclosure relates to a method of inducing anergy of a PBMC of a patient to an antigen, comprising contacting the antibody described above (including a composition comprising the antibody described above; the same applies hereinafter) with an antigen to which immune tolerance is to be induced or a cell having said antigen on a surface, and a PBMC. The method of inducing immune tolerance of the present disclosure is performed ex vivo. If, for example, suppression of rejection against a transplanted organ of a patient receiving transplantation is intended in organ transplantation, a PBMC is a cell harvested from the patient receiving the organ transplantation. If a PBMC is intended to treat or improve an autoimmune disease or allergic disease, the PBMC is a cell harvested from the patient.

For example, immune tolerance to suppress rejection of organ transplantation can be induced by the following method. A PBMC of a patient (recipient) receiving organ transplantation and a PBMC of a subject (donor) providing an organ are prepared, and the donor PBMC is irradiated with 30 Gy radiation. The donor PBMC is mixed with the recipient PBMC at 1:1, and the antibody of the present disclosure (preferably a combination of an anti-human CD80 antibody and anti-human CD86 antibody) is added. A recipient PBMC that is anergic to the donor can be prepared by culturing for 3 to 7 days in a 37° C. and 5% $CO_2$ incubator in a medium for PBMCs.

For example, immune tolerance to treat or improve an autoimmune disease or allergic disease can also be induced by the following method. A patient PBMC is prepared and mixed with an antigen causing an autoimmune disease or allergic disease, and the antibody of the present disclosure (preferably a combination of an anti-human CD80 antibody and anti-human CD86 antibody) is added. A recipient PBMC that is anergic to the antigen can be prepared by culturing for 3 to 7 days in a 37° C. and 5% $CO_2$ incubator in a medium for PBMCs.

The present disclosure comprises a cell (e.g., PBMC) having anergy induced by the method described above. An anergy induced cell (e.g., PBMC) can induce immune tolerance in a patient by administration to a patient, so that an anergy induced cell (e.g., PBMC) can be used as a cell therapy agent. Accordingly, the present disclosure relates to a cell therapy agent comprising a cell (e.g., PBMC) with anergy induced by the method described above as an active ingredient, preferably a cell therapy agent for suppressing rejection in organ transplantation, comprising a cell (e.g., PBMC) of a patient receiving transplantation with anergy to a transplanted organ induced as an active ingredient, or a cell therapy agent for treating an autoimmune disease or allergic disease, comprising a cell (e.g., PBMC) with anergy to an antigen causing an autoimmune disease or allergic disease due to hyperactive immune response induced as an active ingredient, or a cell therapy agent for suppressing rejection in transplantation of an iPS cell or an ES cell and a cell, tissue, or organ derived from said cells. Exemplary rejection includes graft-versus-host disease.

The cell therapy agent of the present disclosure can induce immune tolerance in a patient by administration to the patient. For example, the present disclosure comprises a method of suppressing rejection in organ transplantation, comprising administering a cell therapy agent for suppressing rejection in organ transplantation, comprising a cell (e.g., PBMC) of a patient receiving transplantation with anergy to a transplanted organ induced as an active ingredient to the patient receiving organ transplantation. The present disclosure also comprises a method of treating an autoimmune disease or allergic disease, comprising administering a cell therapy agent for treating an autoimmune disease or allergic disease, comprising a cell (e.g., PBMC) with anergy to an antigen causing an autoimmune disease or allergic disease due to hyperactive immune response induced as an active ingredient to a patient with an autoimmune disease or allergic disease. The present disclosure also comprises a method of suppressing rejection in transplantation of an iPS cell or an ES cell or a cell, tissue, or organ derived from said cells, comprising administering a cell therapy agent for suppressing rejection in transplantation of an iPS cell or an ES cell or a cell, tissue, or organ derived from said cells, comprising a cell (e.g., PBMC) of a patient receiving transplantation with anergy to an iPS cell or an ES cell or a cell, tissue, or organ derived from said cells to be transplanted as an active ingredient to a patient receiving organ transplantation.

The cell therapy agent of the present disclosure comprises a PBMC in a serum containing/free-medium or saline that can be administered to human. When cells are adsorbent, cells can be supported and stored on a detachable substrate and used by detaching the cells upon use. For example, a substrate from which cells are detachable from a change in temperature (RepCell, CellSeed Inc. Japan) or the like can be used.

The present disclosure can be a method of inducing immune tolerance in a patient, comprising contacting the antibody described above with an antigen for which immune tolerance is to be induced or a cell having the antigen on a surface, and a cell (e.g., PBMC) to induce anergy to the antigen of the cell (e.g., PBMC) of the patient, and administering the anergy induced cell (e.g., PBMC) to the patient. For example, the present disclosure comprises a method of suppressing rejection in organ transplantation, comprising preparing a cell (e.g., PBMC) derived from a patient with immune tolerance to a transplanted organ induced by inducing anergy to the transplanted organ of a cell (e.g., PBMC) of a patient by contacting a donor derived cell with the cell (e.g., PBMC) of the patient, and administering the prepared cell (e.g., PBMC) to a patient receiving organ transplantation. The present disclosure also can be a method of treating or improving an autoimmune disease or an allergic disease, comprising preparing a cell (e.g., PBMC) derived from a patient with immune tolerance to an antigen causing an autoimmune disease or an allergic disease induced by inducing anergy to the antigen of a cell (e.g., PBMC) of a patient by contacting the antigen causing an autoimmune disease or an allergic disease with the cell (e.g., PBMC) of the patient, and administering the prepared cell (e.g., PBMC) to a patient of an autoimmune disease or an allergic disease. The present disclosure also comprises a method of suppressing rejection in transplantation of an iPS cell or an ES cell or a cell, tissue, or organ derived from said cells, comprising preparing a cell (e.g., PBMC) derived from a patient with immune tolerance to an iPS cell or an ES cell or a cell, tissue, or organ derived from said cells to be transplanted induced by inducing anergy to the iPS cell or an ES cell or a cell, tissue, or organ derived from said cells of a cell (e.g., PBMC) of a patient by contacting the iPS cell or an ES cell or a cell, tissue, or organ derived from said cells with the cell (e.g., PBMC) of the patient, and administering the prepared cell (e.g., PBMC) to a patient receiving transplantation of the iPS cell or an ES cell or a cell, tissue, or organ derived from said cells.

Administration of a cell therapy agent (anergy induced cell, such as PBMC) is not particularly limited herein as long as the dosage attains a desired therapeutic or preventive effect and can be appropriately determined depending on the symptom, sex, age, or the like. The dosage of the cell therapy agent of the present disclosure can be determined, for example, by using the degree of induction of immune tolerance as an indicator. For example, a single dose of anergy induced PBMCs of the cell therapy agent of the present disclosure is advantageously administered through intravenous injection at generally about 1.0 to $3.7 \times 10^7$ cells/kg body weight, preferably about 2.0 to $5.0 \times 10^7$ cells/kg body weight, and more preferably about 3.0 to $5.0 \times 10^7$ cells/kg body weight, about 1 to 10 times a month and preferably 1 to 5 times a month. If an immune suppression effect is not observed, the amount or number of administration can be increased depending on the symptom.

(Note)

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure is more specifically described hereinafter based on the Examples. However, the present disclosure is not limited to the Examples. Throughout the entire application, all of the cited references are directly incorporated herein by reference.

The Examples are described hereinafter. The organisms used in the following Examples were handled in compliance with the guidelines specified by the Juntendo University and regulatory agencies. Animal experiments were conducted in compliance with the Juntendo University Animal Experiment Control Rules that have been enacted based on "Act on Welfare and Management of Animals", "Guideline for Raising and Keeping of Laboratory Animals" (2006 Ministry of the Environment Notification No. 88), and "Fundamental guidelines for proper conduct of animal experiment and related activities in Academic research institutions" (2006 Ministry of Education, Culture, Sports, Science and Technology Notification No. 71). The experiments were planned based on the so-called 3R. A plan has been already approved and accepted after submission thereof and review by the animal experiment committee at the Juntendo University. Use of genetically engineered mice has been approved after examination of the experimental plan for using recombinant DNA producing animals by the university safety committee. For recombinant DNA experiments, a plan has been already approved and accepted after submission thereof and review by the DNA safety committee at the Juntendo University, and studies were conducted in accordance with the relevant regulations such as "Law Concerning the Conservation and Sustainable Use of Biological Diversity through Regulations on the Use of Living Modified Organisms". Experiment using human peripheral blood (PBMC) was examined based on the principle of fair review and information disclosure and is already approved as being suitable by the ethics committee at the Juntendo University. The studies were conducted while strictly protecting personal information and maintaining anonymity after obtaining information consent for the purpose/plan/method of the studies from specimen providers. Experiments were conducted while complying with the ethical guidelines specified by the ethics committees of the Juntendo University School of Medicine and Sagamihara National Hospital and "guidelines for clinical studies" specified by the Ministry of Health, Labour and Welfare. For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, BD bioscience, BioLegend, or the like).

(Example 1) Mixed Lymphocyte Reaction (MLR) in the Presence of Anti-Human CD80 and Anti-CD86 Antibodies (Subclass IgG1)

(Materials and Methods)

Mononuclear cells (PBMC) were separated from human peripheral blood of three volunteers (one was designated as a donor (donor C), and two were designated as recipients (recipient A and recipient B)) by using Promo cell's Lymphocyte separation Media (Cat. No. C-44010), and adjusted so that the concentration would be $4 \times 10^6$ cells/ml in Biowest's 2% human serum type AB (pool) containing ALyS505N-0 medium (Cell Science & Technology Institute (CSTI) 1020P10). 30 Gy radiation (γ rays) was irradiated onto the donor PBMCs.

Donor PBMCs and recipient PBMCs were dispensed into 4 wells of a 96-well plate (Corning, Cat. No. 3799) at 100 μL/well each so that the ratio would be 1:1 (final total of 200 μL/well). A combination of a humanized anti-human CD80 antibody (v2 (subclass IgG1)) and anti-human CD86 antibody (v5 (subclass IgG1)) or a combination of eBioscience's mouse anti-human CD80 antibody (Cat. No. 16-0809-85) (subclass IgG1) and mouse anti-human CD86 antibody (Cat. No. 16-0869-85) (subclass IgG2) was added thereto at 10 μl so that the concentration after adding each antibody would be 0.1, 1, or 10 μg/mL, and culture was started in a 37° C. 5% $CO_2$ incubator. On day 4 from starting the culture, $^3$H-thymidine (10 μL) was added. On day 5 from starting the culture (after 16 to 20 hours from addition of $^3$H-thymidine), cultured cells were harvested with a Cell Harvester (Molecular Devices). The amount of $^3$H-thymidine incorporation was measured with a scintillation counter.

For IFNγ production, a PBMC mixture that has been mixed by the same method described above with addition of each antibody in the same manner was dispensed into 3 wells of a 48-well Plate (Corning, Cat. No. 3548) at 500 μL/well, and culture was started in a 37° C. 5% $CO_2$ incubator. On day 6 of culture, supernatant was collected. The collected sample was diluted 10 to 25-fold, and then measurement was taken using Biolegend's Human IFNγ ELISA MAX™ Deluxe, Cat. 430104.

(Results)

Figure 2:
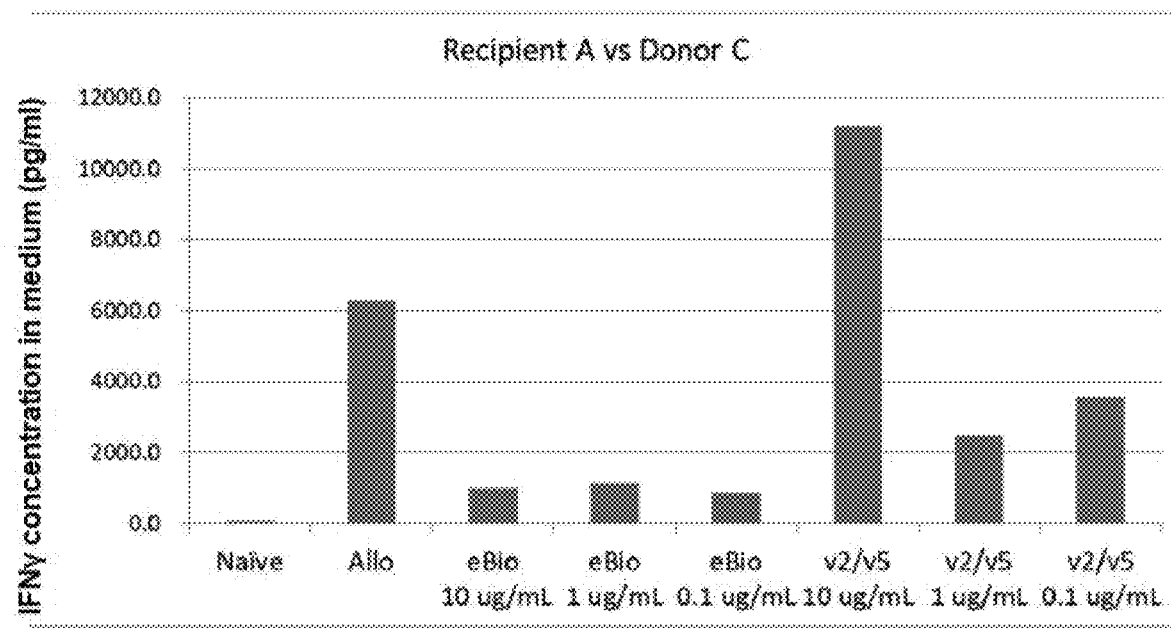
FIG. 2 shows results of a mixed lymphocyte reaction (IFNγ production) in the presence of anti-human CD80 and anti-CD86 antibodies (IgG1). The vertical axis indicates the concentration in a medium (pg/ml).
Figure 2:
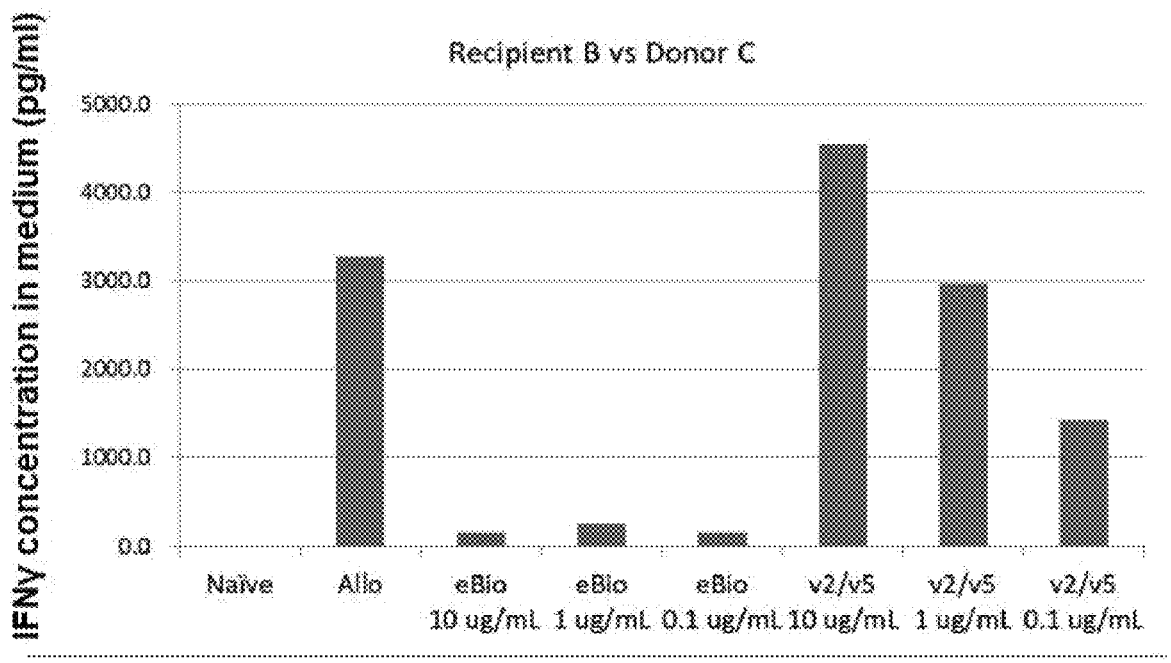

As a result, as shown in FIG. 1, the combination of a humanized anti-human CD80 antibody (v2 (subclass IgG1)) and humanized anti-human CD86 antibody (v5 (subclass IgG1)) had low $^3$H-thymidine incorporation at nearly the same level as the combination of eBioscience's mouse anti-human CD80 antibody and mouse anti-human CD86 antibody, i.e., suppressed activation of immune cells. Meanwhile, as shown in FIG. 2, IFNγ production evaluation resulted in low production in the presence of eBioscience's mouse anti-human CD80 and CD86 antibodies, whereas IFNγ production dependent on the amount of antibodies added was observed in the presence of a humanized anti-human CD80 and CD86 antibodies (subclass IgG1). At 10 μg/mL, production equal to or greater than that in the absence of antibodies (FIG. 2: Allo) was observed. Although not wishing to be bound by any theory, it is understood that eBioscience's antibodies have low IFNγ production due to being mouse antibodies and having low reactivity.

(Example 2) Mixed Lymphocyte Reaction (MLR) in the Presence of Anti-Human CD80 and Anti-CD86 Antibodies (Subclass IgG1)

(Materials and Methods)

$^3$H-thymidine incorporation when a combination of a humanized anti-human CD80 antibody (v2 (subclass IgG1)) and anti-human CD86 antibody (v5 or v9 (subclass IgG1))) or a combination of eBioscience's mouse anti-human CD80 antibody (Cat. No. 16-0809-85) and mouse anti-human CD86 antibody (Cat. No. 16-0869-85) was added so that the concentration after addition of each antibody would be 10 μg/mL was evaluated by the same method as Example 1. Of the three volunteers, one was designated as a donor (donor F), and two were designated as recipients (recipient D and recipient E).

Further, IFNγ production was evaluated for a combination of a humanized anti-human CD80 antibody (v2 (subclass IgG1)) and humanized anti-human CD86 antibody (v9 (subclass IgG1)) and a combination of eBioscience's mouse anti-human CD80-antibody and anti-human CD86 antibody. For the combination of a humanized anti-human CD80 antibody (v2 (subclass IgG1)) and anti-human CD86 antibody (v9 (subclass IgG1)), IFNγ production when radiation irradiated donor PBMCs were not added was also evaluated in addition to the method of Example 1.

(Results)

Figure 3:
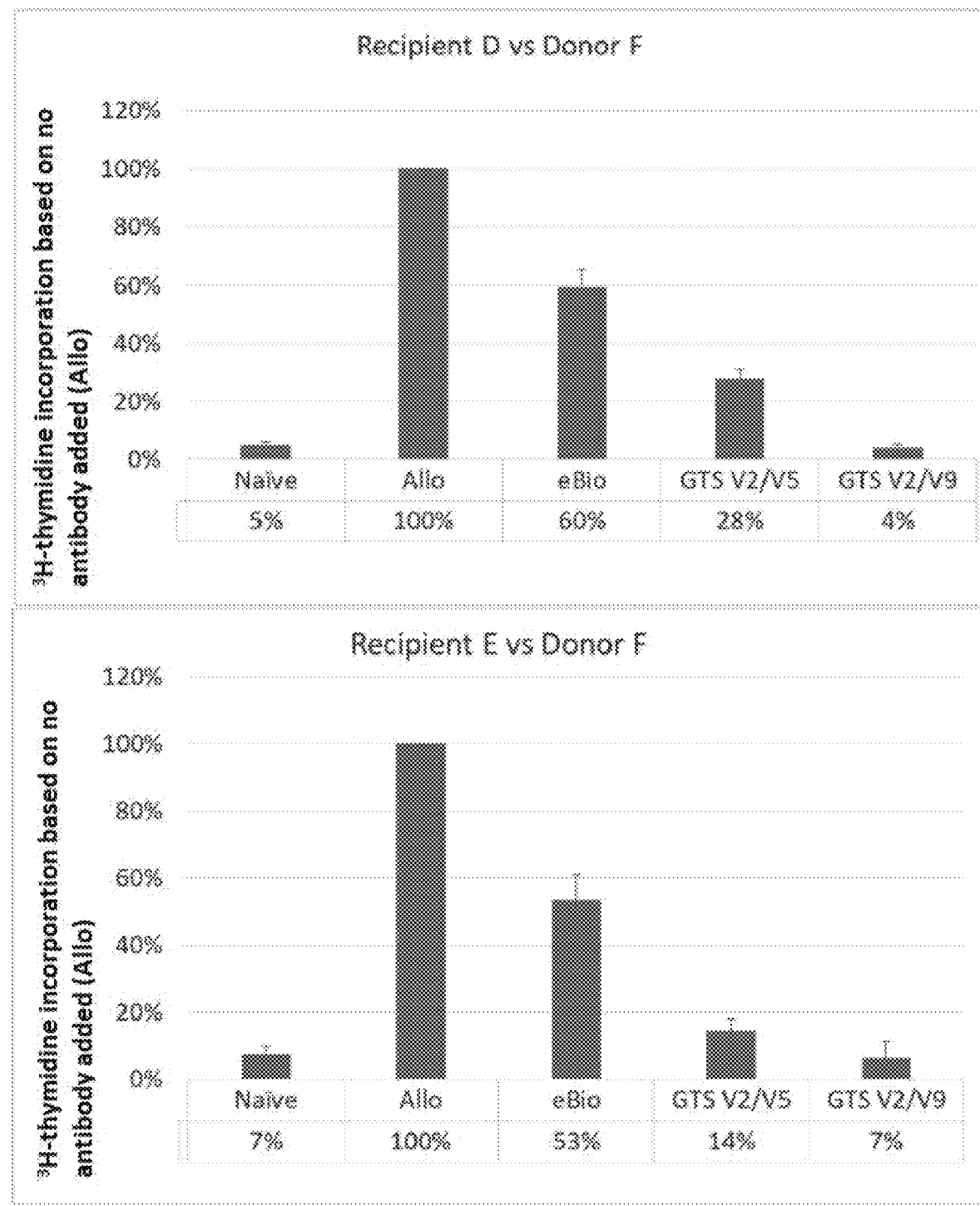
FIG. 3 shows results of a mixed lymphocyte reaction ($^3$H-thymidine incorporation) in the presence of anti-human CD80 and anti-CD86 antibodies (IgG1). The vertical axis indicates $^3$H-thymidine incorporation, based on no antibody added (Allo).
Figure 4:
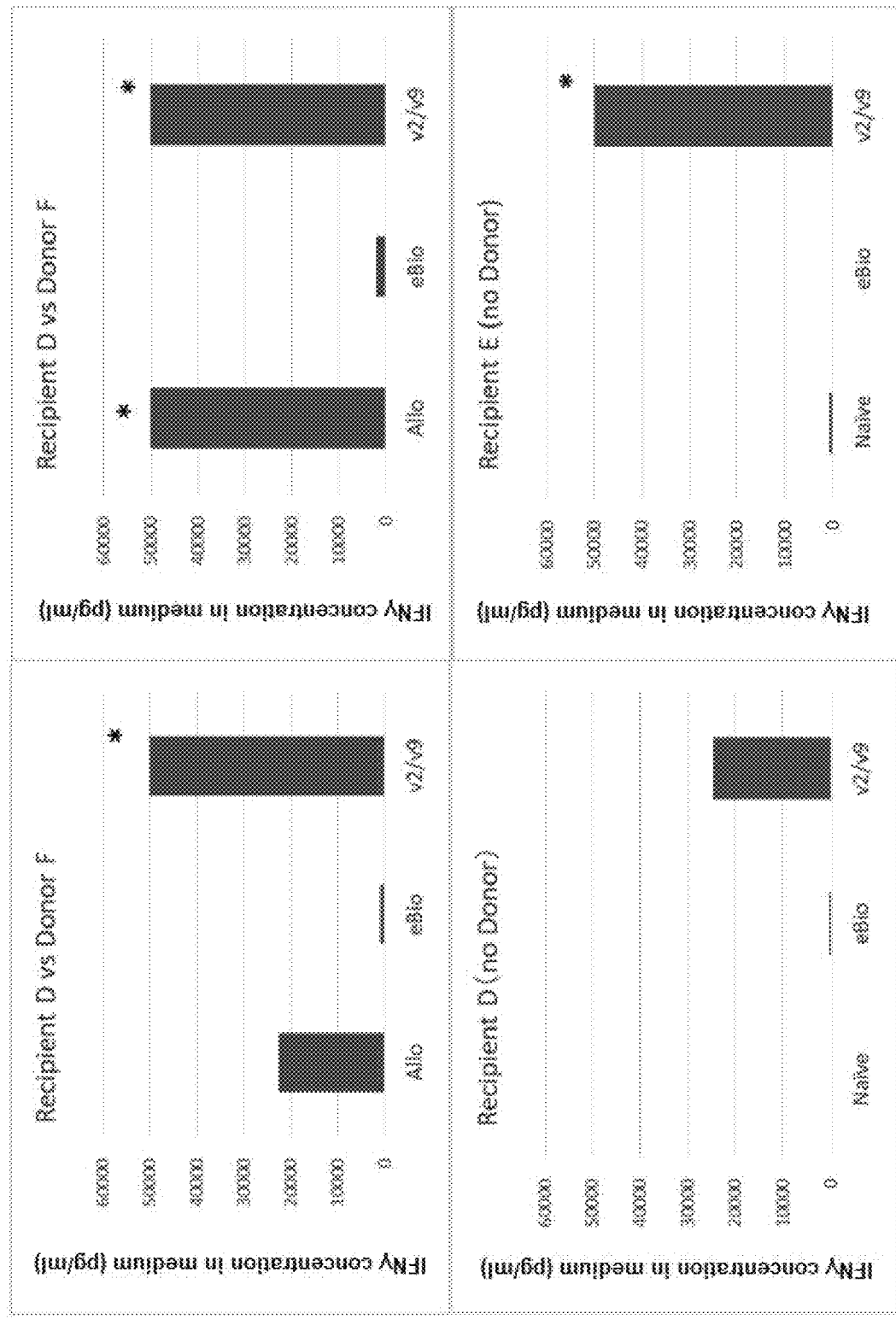
FIG. 4 shows results of a mixed lymphocyte reaction (IFNγ production) in the presence of anti-human CD80 and anti-CD86 antibodies (IgG1). Top row: with donor stimulation, bottom row: no donor stimulation. * represents 50000 pg/mL or greater. The vertical axis indicates the concentration in a medium (pg/ml).

As a result, as shown in FIG. 3, the combination of a humanized anti-human CD80 antibody and anti-human CD86 antibody exhibited greater suppression of 3H-thymidine incorporation than the combination of mouse anti-human CD80-antibody and anti-human CD86 antibody. Meanwhile, as shown in FIG. 4, IFNγ production was low with eBioscience's mouse anti-human CD80 and CD86 antibodies in the same manner as Example 1. Production equal to or greater than that upon donor simulation in the absence of an antibody was observed for humanized anti-human CD80 and CD86 antibodies. Furthermore, the same IFNγ production was observed when humanized anti-CD80 and anti-human CD86 antibodies were added, even radiation irradiated donor PBMCs were not added.

(Example 3) Mixed Lymphocyte Reaction (MLR) in the Presence of Anti-Human CD80 and Anti-CD86 Antibodies (Subclasses IgG1, IgG2, and IgG4)

In Example 2, IFNγ production was observed even when radiation irradiated donor PBMCs were not added. Thus, the classes of humanized anti-human CD80 antibody and anti-human CD86 antibody were switched, and $^3$H-thymidine incorporation when a combination of the humanized anti-human CD80 antibody (v2 (subclass IgG2 or IgG4)) and anti-human CD86 antibody (v9 (subclass IgG2 or IgG4)) of the same subclass, and a combination of eBioscience's mouse anti-human CD80 antibody (Cat. No. 16-0809-85) and anti-human CD86 antibody (Cat. No. 16-0869-85) were added so that the concentration after addition of each antibody would be 1, 3, or 10 μg/mL, and IFNγ production when the antibodies were added so that the concentration after addition of each antibody would be 10 μg/mL. Of the three volunteers, one was designated as a donor (donor I), and two were designated as recipients (recipient G and recipient H). The following is the specific experimental system.

[$^3$H-thymidine incorporation (each antibody concentration: 1, 3, and 10 μg/mL) (FIG. 5)
  no antibody addition (Allo), radiation irradiated donor PBMC added
  eBioscience's mouse anti-human CD80 antibody and mouse anti-human CD86 antibody
  humanized anti-human CD80 antibody (v2 (IgG2)) and humanized anti-human CD86 antibody (v9 (IgG2))
  humanized anti-human CD80 antibody (v2 (IgG4)) and humanized anti-human CD86 antibody (v9 (IgG4))
[IFNγ production (each antibody concentration: 10 μg/mL) (FIG. 6)
With addition of radiation irradiated donor PBMC (Allo)
  no antibody addition
  eBioscience's mouse anti-human CD80 antibody and anti-human CD86 antibody
  humanized anti-human CD80 antibody (v2 (IgG2)) and humanized anti-human CD86 antibody (v9 (IgG2))
  humanized anti-human CD80 antibody (v2 (IgG4)) and humanized anti-human CD86 antibody (v9 (IgG4))
No addition of radiation irradiated donor PBMC (Naïve)
  no antibody addition (Allo)
  eBioscience's mouse CD80 antibody and anti-CD86 antibody
  humanized anti-CD80 antibody (v2 (IgG1)) and humanized anti-human CD86 antibody (v9 (IgG1))
  humanized anti-CD80 antibody (v2 (IgG2)) and humanized anti-human CD86 antibody (v9 (IgG2))
  humanized anti-CD80 antibody (v2 (IgG4)) and humanized anti-human CD86 antibody (v9 (IgG4))
(Results)

Figure 5:
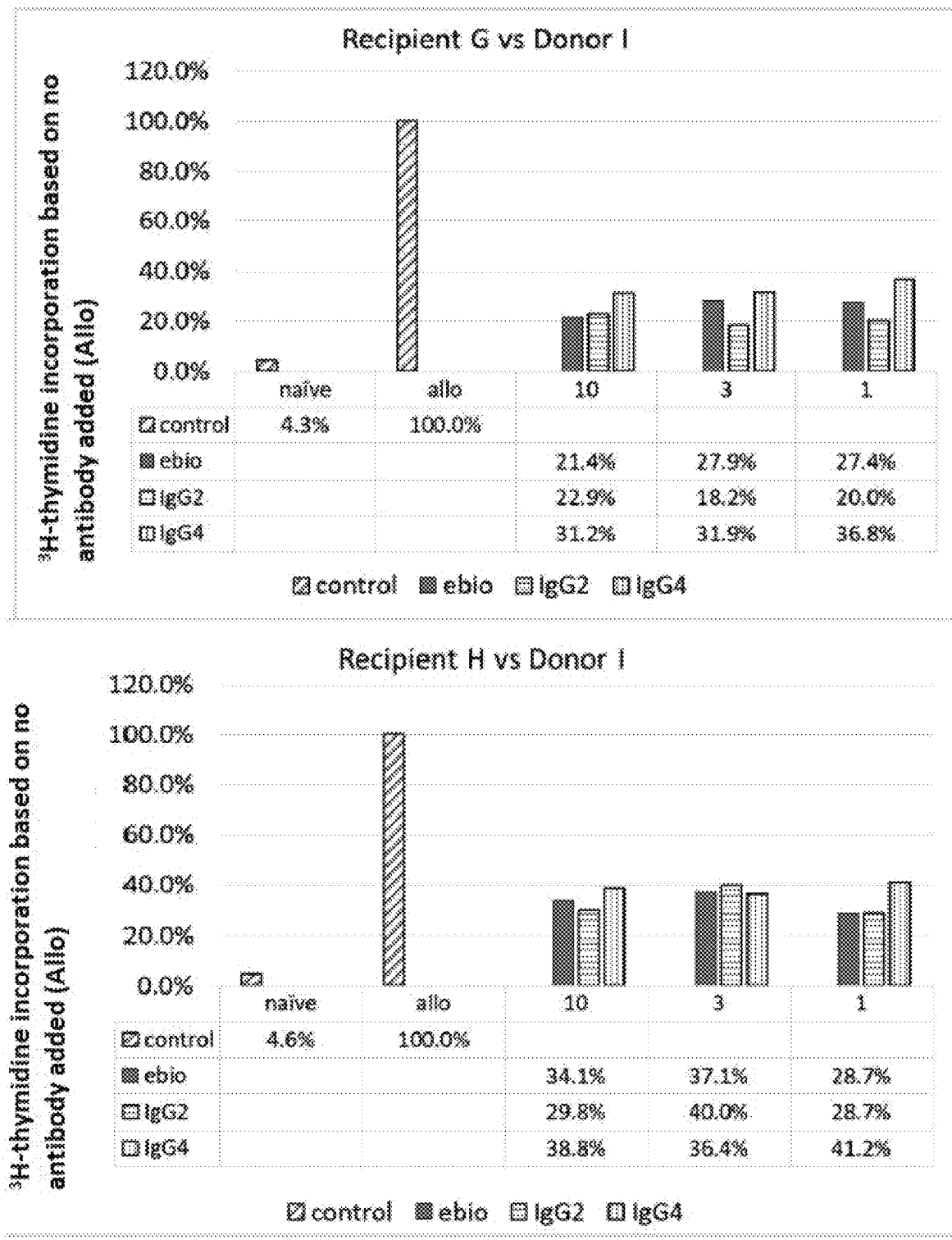
FIG. 5 shows results of a mixed lymphocyte reaction ($^3$H-thymidine incorporation) in the presence of anti-CD80 and anti-CD86 antibodies (IgG2, IgG4). The vertical axis indicates $^3$H-thymidine incorporation, based on no antibody added (Allo). 10, 3, and 1 are concentrations of each added antibody (μg/ml).
Figure 6:
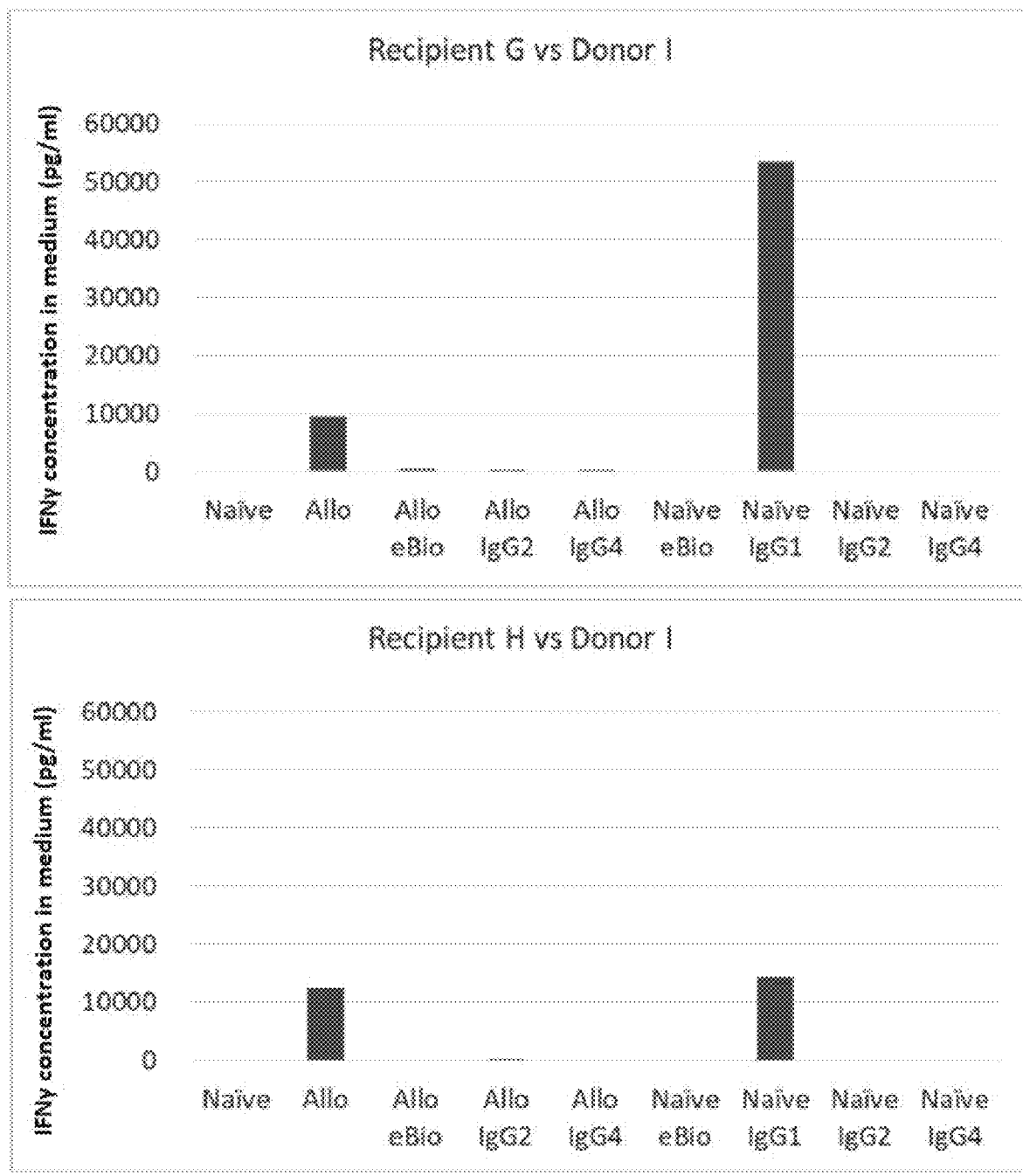
FIG. 6 shows results of a mixed lymphocyte reaction (IFNγ production) in the presence of anti-CD80 and anti- CD86 antibodies (IgG1, IgG2, IgG4). The vertical axis indicates the concentration in a medium (pg/ml).

As a result, as shown in FIG. 5, subclasses IgG2 and IgG4 exhibited suppression of $^3$H-thymidine incorporation in the same manner as Examples 1 and 2. Meanwhile, as shown in FIG. 6, IFNγ production was observed in subclass IgG1, but surprisingly IFNγ was not produced at all in subclasses IgG2 and IgG4.

(Example 4) Mixed Lymphocyte Reaction (MLR) when Cells Obtained from Culturing in the Presence of Anti-Human CD80 and Anti-Human CD86 Antibodies (Subclass IgG1, IgG2, or IgG4) were Added (Materials and Methods)

Culture was continued up to day 14 by the method described in Example 1 in the presence of a combination of subclasses IgG1, IgG2, and IgG4 of humanized anti-human CD80 antibody (v2) and anti-human CD86 antibody (v9). The humanized anti-human CD80 antibody (v2) of subclass IgG2 consists of a heavy chain with the amino acid sequence of SEQ ID NO: 2 and a light chain with the amino acid sequence of SEQ ID NO: 4. The humanized anti-human CD80 antibody (v2) of subclass IgG4 consists of a heavy chain with the amino acid sequence of SEQ ID NO: 6 and a light chain with the amino acid sequence of SEQ ID NO: 8. The anti-human CD86 antibody (v9) of subclass IgG2 consists of a heavy chain with the amino acid sequence of SEQ ID NO: 10 and a light chain with the amino acid sequence of SEQ ID NO: 12. The anti-human CD86 antibody (v9) of subclass IgG4 consists of a heavy chain with the amino acid sequence of SEQ ID NO: 14 and a light chain with the amino acid sequence of SEQ ID NO: 16. After culture, the resulting anergic cells, recipient PBMCs (R-PBMC), and radiation irradiated donor PBMCs (D-PBMC) were mixed in accordance with the following table, and then $^3$H-thymidine incorporation was evaluated after mixing by the method described in Example 1.

TABLE 1

| Cell suspension | | R-PBMC | Anergic T | D-PBMC | Medium |
|---|---|---|---|---|---|
| Naïve (R-PBMC only) | μL | 200.0 | 0.0 | 0.0 | 300.0 |
|  | cells | 4.0 × 10$^5$ | 0 | 0.0 | 0 |
| Allo (R-PBMC + D-PBMC) | μL | 200.0 | 0.0 | 200.0 | 100.0 |
|  | cells | 4.0 × 10$^5$ | 0 | 4.0 × 10$^5$ | 0 |
| R-PBMC:Anergic T = 1:1/2 | μL | 200.0 | 100.0 | 200.0 | 0.0 |
|  | cells | 4.0 × 10$^5$ | 2.0 × 10$^5$ | 4.0 × 10$^5$ | 0 |
| R-PBMC:Anergic T = 1:1/4 | μL | 200.0 | 50.0 | 200.0 | 50.0 |
|  | cells | 4.0 × 10$^5$ | 1.0 × 10$^5$ | 4.0 × 10$^5$ | 0 |
| R-PBMC:Anergic T = 1:1/8 | μL | 200.0 | 25.0 | 200.0 | 75.0 |
|  | cells | 4.0 × 10$^5$ | 5.0 × 10$^4$ | 4.0 × 10$^5$ | 0 |

(Results)

Figure 7:
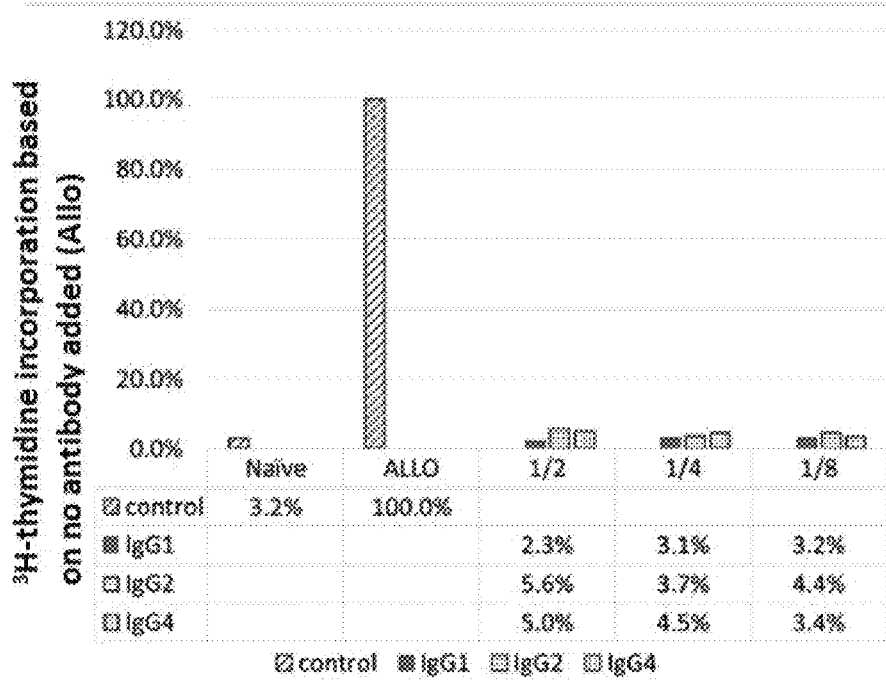
FIG. 7 shows results of a mixed lymphocyte reaction ($^3$H-thymidine incorporation) upon addition of a cell obtained in the presence of anti-CD80 and anti-CD86 antibodies (IgG1, IgG2, IgG4). The vertical axis indicates $^3$H-thymidine incorporation, based on no antibody added (Allo). ½, ¼, and ⅛ are ratios of mixture of cells obtained in the presence of anti-CD80 and anti-CD86 antibodies (IgG1, IgG2, IgG4) to naïve responder cells.

As a result, as shown in FIG. 7, cells obtained in the presence of antibodies of any subclass suppressed $^3$H-thymidine incorporation equally.

(Example 5) Induction of Immune Tolerance in Patient Who has Received Organ Transplantation Tests were conducted by the same method as the method described in Satoru Todo et al. Hepatorogy, 64 (vol. 2), 632-643 (2016). Briefly, anergic T cells that are specific to a donor antigen are induced by co-culturing lymphocytes harvested from the spleen or peripheral blood of a recipient, donor derived lymphocytes irradiated with 30 Gy radiation, and humanized anti-CD80 antibody and anti-CD86 antibody of subclass IgG4 used in Example 4. The anergic T cells are administered on day 13 after surgery to a recipient who has received liver transplantation. The status is subsequently followed up.

(Example 6) Chimeric Anti-Human CD80 and Chimeric Anti-Human CD86 Antibodies (Subclass IgG1)

Antibody Preparation

The inventors attempted to improve anti-human CD80 antibodies and anti-human CD86 antibodies for use in cell therapy. Specifically, based on eBioscience's mouse anti-human CD80 antibody and mouse anti-human CD86 antibody, chimeric antibodies of each of them were prepared. The prepared chimeric anti-human CD80 antibody (subclass IgG1) consists of a heavy chain with the amino acid sequence of SEQ ID NO: 38 and a light chain with the amino acid sequence of SEQ ID NO: 40. The prepared chimeric anti-human CD86 antibody (subclass IgG1) consists of a heavy chain with the amino acid sequence of SEQ ID NO: 42 and a light chain with the amino acid sequence of SEQ ID NO: 44. A plasmid encoding them was commissioned to a third party (TPG Biologics, Inc. Taiwan) and expressed from a CHO cell, and antibodies were produced/purified.

Mixed lymphocyte reaction (MLR) in the presence of chimeric anti-human CD80 and chimeric anti-CD86 antibodies (subclass IgG1)

IFNγ Production

In almost the same manner as the method described in Example 1, mononuclear cells (PBMC) were separated from human peripheral blood of two volunteers (one was designated as a donor, and the other was designated as a recipient) by using Promo cell's Lymphocyte separation Media (Cat. No. C-44010), and adjusted so that the concentration would be $2 \times 10^6$ cells/ml in Biowest's 2% human serum type AB (pool) containing ALyS505N-0 medium (Cell Science & Technology Institute (CSTI) 1020P10). 30 Gy radiation (γ rays) was irradiated onto the donor PBMCs.

The experimental system was constructed as follows.
1. "naïve": recipient PBMC, $1 \times 10^6$ cells
2. "allo": recipient PBMC, $1 \times 10^6$ cells and donor PBMC, $1 \times 10^6$ cells
3. "chimeric anti-CD80": recipient PBMC, $1 \times 10^6$ cells and chimeric anti-human CD80 antibody, 4 µg
4. "chimeric anti-CD86": recipient PBMC, $1 \times 10^6$ cells and chimeric anti-human CD86 antibody, 4 µg Systems 1. to 4. were placed in each well of a 96 well plate (Corning, Cat. No. 3799) so that the final reaction volume would be 200 µL (final concentration of antibodies was about 20 µg/mL), and culture was started in a 37° C. 5% $CO_2$ incubator. On day 5 and day 6 from starting the culture, supernatant was collected. The collected sample was diluted 20 to 25-fold, and then measurement was taken using Biolegend's Human IFNγ ELISA MAX$^7$m Deluxe, Cat. 430104.

Results

Figure 8:
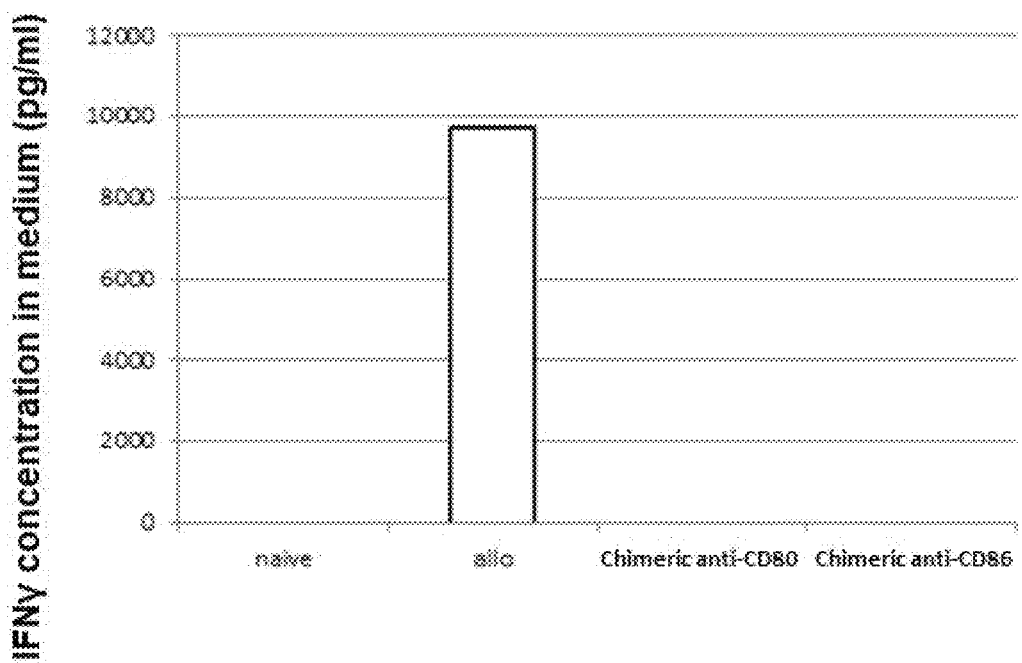
FIG. 8 shows results of a mixed lymphocyte reaction (IFNγ production) in the presence of chimeric anti-CD80 antibodies and chimeric anti-CD86 antibodies. The vertical axis indicates the concentration in a medium (pg/ml).

As shown in FIG. 8, neither the chimeric anti-human CD80 antibody nor the chimeric anti-human CD86 antibody demonstrated detectable IFNγ production.

Measurement of the Amount of $^3$H-Thymidine Incorporation

Basically, experiments were conducted in accordance with the methods described in Examples 1 and 4. Recipient PBMCs and donor PBMCs that were freshly separated from human peripheral blood were used, or those cryopreserved at −80° C. were rapidly thawed and used. These cells were both adjusted so that the concentration would be $4 \times 10^6$ cells/mL in Biowest's 2% human serum type AB (pool) containing ALyS505N-0 medium (Cell Science & Technology Institute (CSTI) 1020P10). 20 Gy radiation was irradiated onto the donor PBMCs. The donor PBMCs and recipient PBMCs were mixed at 1:1, and a chimeric anti-human CD80 antibody and chimeric anti-human CD86 antibody were added to the mixture so that the final concentration would each be 10 µg/ml. The cells were cultured for 7 days in a 37° C. 5% $CO_2$ incubator on a 6 cm to 10 cm Petri dish (culture volume of 6 to 18 mL).

On day 7 from starting the culture, cultured recipient PBMCs were collected by centrifugation and adjusted to $4 \times 10^6$ cells/mL in the medium described above. To the cultured recipient PBMCs, newly prepared and irradiated donor PBMCs were added so that the cell count ratio would be 2:1, and a chimeric anti-human CD80 antibody and chimeric anti-human CD86 antibody were added so that each would have a final concentration of 5 µg/ml. The cells were cultured for 7 days under the same conditions as above (cell density: $4 \times 10^6$ cells/mL).

On day 14 from starting the culture, induced cells were collected by centrifugation. Each cell was mixed at the following ratio:
1. "naïve": recipient PBMC, $4 \times 10^5$ cells
2. "allo": recipient PBMC, $4 \times 10^5$ cells and donor PBMC, $4 \times 10^5$ cells
3. "1:½": recipient PBMC, $4 \times 10^5$ cells, donor PBMC, $4 \times 10^5$ cells, and induced cells $2 \times 10^5$ cells
4. "1:¼": recipient PBMC, $4 \times 10^5$ cells, donor PBMC, $4 \times 10^5$ cells, and induced cells $1 \times 10^5$ cells
5. "1:⅛": recipient PBMC, $4 \times 10^5$ cells, donor PBMC, $4 \times 10^5$ cells, and induced cells $5 \times 10^5$ cells
6. "1:1/16": recipient PBMC, $4 \times 10^5$ cells, donor PBMC, $4 \times 10^5$ cells, and induced cells $2.5 \times 10^5$ cells Systems 1. to 6. were each dispensed in 4 wells of a 96 well plate (Corning, Cat. No. 3799) and co-cultured in a 37° C. 5% $CO_2$ incubator. On day 4 from starting the co-culture, $^3$H-thymidine (10 µl) was added. On day 5 from starting the co-culture (16 to 20 hours after adding $^3$H-thymidine incorporation), $^3$H-thymidine in the culture was removed to measure the amount of $^3$H-thymidine incorporation.

Results

Figure 9:
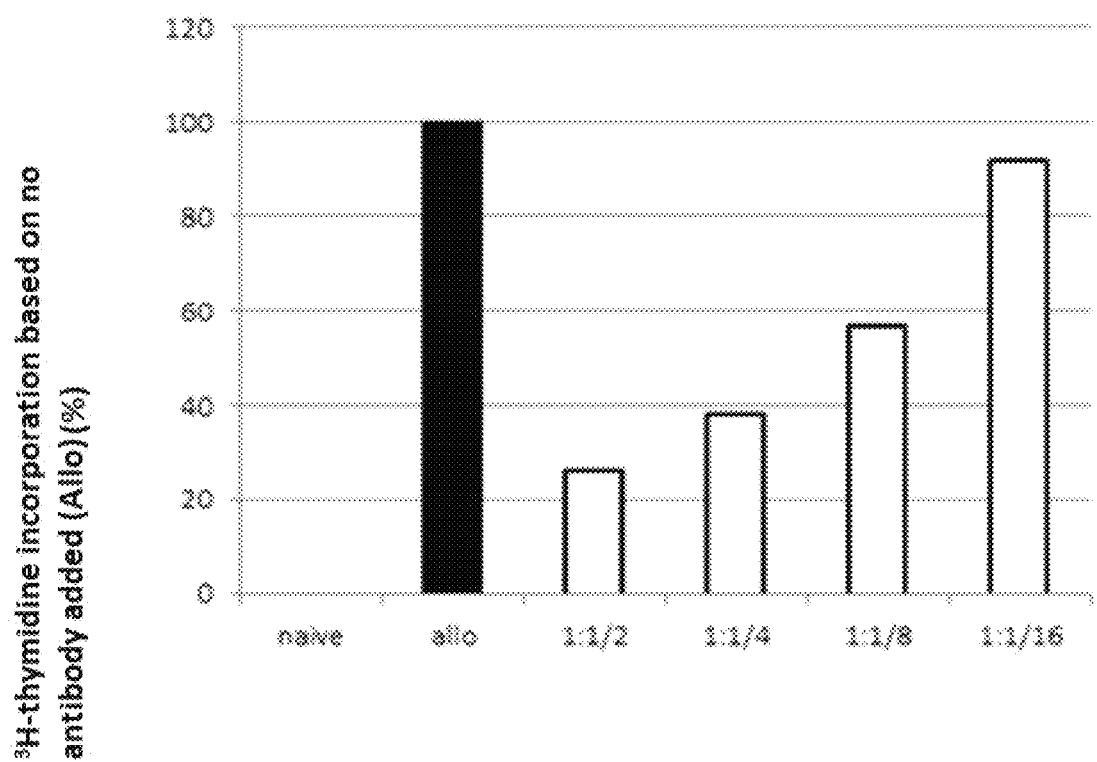
FIG. 9 shows results of a mixed lymphocyte reaction ($^3$H-thymidine incorporation) upon addition of a cell obtained in the presence of chimeric anti-CD80 and chimeric anti-CD86 antibodies. The vertical axis indicates 3H-thymidine incorporation, based on no antibody added (Allo). ½, ¼, ⅛, and ¹⁄₁₆ are ratios of mixture of cells obtained in the presence of chimeric anti-CD80 and chimeric anti-CD86 antibodies to naïve responder cells.

As shown in FIG. 9, induced cells reduced the amount of $^3$H-thymidine incorporation in a dose dependent manner (i.e., activation of immune cells was suppressed). Therefore, chimeric anti-human CD80 antibodies and chimeric anti-human CD86 antibodies were demonstrated to be antibodies suitable for cell therapy, which can induce anergic T cells without causing detrimental IFNγ production.

[Note]

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application claims priority to Japanese Patent Application No. 2018-118996 (filed on Jun. 22, 2018). It is understood that the content thereof (can be the entire document) is incorporated herein by reference. Further, a part of or the entire content of Japanese Patent Application No. 2018-119001 and Japanese Patent Application No. 2018-1190031 (both filed on Jun. 22, 2018) and international applications claiming priority thereto is incorporated herein by reference.

INDUSTRIAL APPLICABILITY

The present disclosure provides an antibody with a structure having a feature of improving the effect of immune tolerance or not attenuating the effect of immune tolerance. A technology that can be utilized in industries (pharmaceutical) related to formulations or the like based on such a technology is provided.

SEQUENCE LISTING FREE TEXT

SEQ ID NO: 1: heavy chain nucleic acid sequence of anti-CD80 antibody (IgG2)
SEQ ID NO: 2: heavy chain amino acid sequence of anti-CD80 antibody (IgG2)
SEQ ID NO: 3: light chain nucleic acid sequence of anti-CD80 antibody (IgG2)
SEQ ID NO: 4: light chain amino acid sequence of anti-CD80 antibody (IgG2)
SEQ ID NO: 5: heavy chain nucleic acid sequence of anti-CD80 antibody (IgG4)
SEQ ID NO: 6: heavy chain amino acid sequence of anti-CD80 antibody (IgG4)
SEQ ID NO: 7: light chain nucleic acid sequence of anti-CD80 antibody (IgG4)
SEQ ID NO: 8: light chain amino acid sequence of anti-CD80 antibody (IgG4)
SEQ ID NO: 9: heavy chain nucleic acid sequence of anti-CD86 antibody (IgG2)
SEQ ID NO: 10: heavy chain amino acid sequence of anti-CD86 antibody (IgG2)
SEQ ID NO: 11: light chain nucleic acid sequence of anti-CD86 antibody (IgG2)
SEQ ID NO: 12: light chain amino acid sequence of anti-CD86 antibody (IgG2)
SEQ ID NO: 13: heavy chain nucleic acid sequence of anti-CD86 antibody (IgG4)
SEQ ID NO: 14: heavy chain amino acid sequence of anti-CD86 antibody (IgG4)
SEQ ID NO: 15: light chain nucleic acid sequence of anti-CD86 antibody (IgG4)
SEQ ID NO: 16: light chain amino acid sequence of anti-CD86 antibody (IgG4)
SEQ ID NO: 17: heavy chain variable region nucleic acid sequence of anti-CD80 antibody (IgG2)
SEQ ID NO: 18: heavy chain variable region amino acid sequence of anti-CD80 antibody (IgG2)
SEQ ID NO: 19: light chain variable region nucleic acid sequence of anti-CD80 antibody (IgG2)
SEQ ID NO: 20: light chain variable region amino acid sequence of anti-CD80 antibody (IgG2)
SEQ ID NO: 21: heavy chain variable region nucleic acid sequence of anti-CD86 antibody (IgG2)
SEQ ID NO: 22: heavy chain variable region amino acid sequence of anti-CD86 antibody (IgG2)
SEQ ID NO: 23: light chain variable region nucleic acid sequence of anti-CD86 antibody (IgG2)
SEQ ID NO: 24: light chain variable region amino acid sequence of anti-CD86 antibody (IgG2)
SEQ ID NO: 25: amino acid sequence of CDRH1 of anti-CD80 antibody (IgG2)
SEQ ID NO: 26: amino acid sequence of CDRH2 of anti-CD80 antibody (IgG2)
SEQ ID NO: 27: amino acid sequence of CDRH3 of anti-CD80 antibody (IgG2)
SEQ ID NO: 28: amino acid sequence of CDRL1 of anti-CD80 antibody (IgG2)
SEQ ID NO: 29: amino acid sequence of CDRL2 of anti-CD80 antibody (IgG2)
SEQ ID NO: 30: amino acid sequence of CDRL3 of anti-CD80 antibody (IgG2)
SEQ ID NO: 31: amino acid sequence of CDRH1 of anti-CD86 antibody (IgG2)
SEQ ID NO: 32: amino acid sequence of CDRH2 of anti-CD86 antibody (IgG2)
SEQ ID NO: 33: amino acid sequence of CDRH3 of anti-CD86 antibody (IgG2)
SEQ ID NO: 34: amino acid sequence of CDRL1 of anti-CD86 antibody (IgG2)
SEQ ID NO: 35: amino acid sequence of CDRL2 of anti-CD86 antibody (IgG2)
SEQ ID NO: 36: amino acid sequence of CDRL3 of anti-CD86 antibody (IgG2)
SEQ ID NO: 37: heavy chain nucleic acid sequence of chimeric anti-CD80 antibody
SEQ ID NO: 38: heavy chain amino acid sequence of chimeric anti-CD80 antibody
SEQ ID NO: 39: light chain nucleic acid sequence of chimeric anti-CD80 antibody
SEQ ID NO: 40: light chain amino acid sequence of chimeric anti-CD80 antibody
SEQ ID NO: 41: heavy chain nucleic acid sequence of chimeric anti-CD86 antibody
SEQ ID NO: 42: heavy chain amino acid sequence of chimeric anti-CD86 antibody
SEQ ID NO: 43: light chain nucleic acid sequence of chimeric anti-CD86 antibody
SEQ ID NO: 44: light chain amino acid sequence of chimeric anti-CD86 antibody
SEQ ID NO: 45: heavy chain variable region nucleic acid sequence of chimeric anti-CD80 antibody
SEQ ID NO: 46: heavy chain variable region amino acid sequence of chimeric anti-CD80 antibody
SEQ ID NO: 47: light chain variable region nucleic acid sequence of chimeric anti-CD80 antibody
SEQ ID NO: 48: light chain variable region amino acid sequence of chimeric anti-CD80 antibody
SEQ ID NO: 49: heavy chain variable region nucleic acid sequence of chimeric anti-CD86 antibody
SEQ ID NO: 50: heavy chain variable region amino acid sequence of chimeric anti-CD86 antibody
SEQ ID NO: 51: light chain variable region nucleic acid sequence of chimeric anti-CD86 antibody
SEQ ID NO: 52: light chain variable region amino acid sequence of chimeric anti-CD86 antibody
SEQ ID NO: 53: amino acid sequence of CDRH1 of chimeric anti-CD80 antibody
SEQ ID NO: 54: amino acid sequence of CDRH2 of chimeric anti-CD80 antibody
SEQ ID NO: 55: amino acid sequence of CDRH3 of chimeric anti-CD80 antibody
SEQ ID NO: 56: amino acid sequence of CDRL1 of chimeric anti-CD80 antibody
SEQ ID NO: 57: amino acid sequence of CDRL2 of chimeric anti-CD80 antibody
SEQ ID NO: 58: amino acid sequence of CDRL3 of chimeric anti-CD80 antibody
SEQ ID NO: 59: amino acid sequence of CDRH1 of chimeric anti-CD86 antibody
SEQ ID NO: 60: amino acid sequence of CDRH2 of chimeric anti-CD86 antibody
SEQ ID NO: 61: amino acid sequence of CDRH3 of chimeric anti-CD86 antibody
SEQ ID NO: 62: amino acid sequence of CDRL1 of chimeric anti-CD86 antibody
SEQ ID NO: 63: amino acid sequence of CDRL2 of chimeric anti-CD86 antibody
SEQ ID NO: 64: amino acid sequence of CDRL3 of chimeric anti-CD86 antibody

The invention claimed is:

1. An antibody or variant thereof that inhibits an interaction between CD80 and/or CD86 expressed on a surface of a cell, and CD28 expressed on a surface of another cell, wherein the antibody or variant thereof induces immune tolerance to a cell derived from a subject; does not substantially induce the production of a cytokine by immunostimulation; reduces $^3$H-thymidine uptake in the cell derived from the subject compared to a cell in which immune tolerance has not been induced; and is a chimeric antibody, and wherein the antibody or variant thereof comprises:
 a heavy chain having the amino acid sequence of SEQ ID NO: 38 and a light chain having the amino acid sequence of SEQ ID NO: 40, or
 a heavy chain having the amino acid sequence of SEQ ID NO: 42 and a light chain having the amino acid sequence of SEQ ID NO: 44.

2. The antibody or variant thereof of claim 1, wherein the cytokine comprises interferon γ.

3. The antibody or variant thereof of claim 1, wherein a subclass of the antibody is IgG1.

4. An antibody or variant thereof that inhibits an interaction between CD80 and/or CD86 expressed on a surface of a cell, and CD28 expressed on a surface of another cell, wherein the antibody or variant thereof induces immune tolerance to a cell derived from a subject: does not substantially induce the production of a cytokine by immunostimulation: reduces $^3$H-thymidine uptake in the cell derived from the subject compared to a cell in which immune tolerance has not been induced; and is a chimeric antibody, and wherein the antibody or variant thereof comprises:
 (a) a VH comprising CDRH1 of the amino acid sequence set forth in SEQ ID NO: 53, CDRH2 of the amino acid sequence set forth in SEQ ID NO: 54, and CDRH3 of the amino acid sequence set forth in SEQ ID NO: 55, and a VL comprising CDRL1 of the amino acid sequence set forth in SEQ ID NO: 56, CDRL2 of the amino acid sequence set forth in SEQ ID NO: 57, and CDRL3 set forth in SEQ ID NO: 58; or
 (b) a VH comprising CDRH1 of the amino acid sequence set forth in SEQ ID NO: 59, CDRH2 of the amino acid sequence set forth in SEQ ID NO: 60, and CDRH3 of the amino acid sequence set forth in SEQ ID NO: 61, and a VL comprising CDRL1 of the amino acid sequence set forth in SEQ ID NO: 62, CDRL2 of the amino acid sequence set forth in SEQ ID NO: 63, and CDRL3 set forth in SEQ ID NO: 64.

5. The antibody or variant thereof of claim 4, comprising:
 (a) a VH having the amino acid sequence set forth in SEQ ID NO: 46 or a variant sequence thereof, and a VL having the amino acid sequence set forth in SEQ ID NO: 48 or a variant sequence thereof, or
 (b) a VH having the amino acid sequence set forth in SEQ ID NO: 50 or a variant sequence thereof, and a VL having the amino acid sequence set forth in SEQ ID NO: 52 or a variant sequence thereof.

6. The antibody or variant thereof of claim 1, wherein an Fc moiety of the antibody is a moiety that does not substantially induce the production of a cytokine by immunostimulation.

7. The antibody or variant thereof of claim 1, having an ability to induce immune tolerance.

8. The antibody or variant thereof of claim 1, wherein the cell expressing CD80 and/or CD86 is an antigen presenting cell, and the other cell expressing CD28 is a T cell.

9. A nucleic acid molecule encoding the amino acid sequence or a portion thereof of the antibody or variant thereof of claim 1.

10. The nucleic acid molecule of claim 9, comprising:
 (a) a polynucleotide encoding a VH, having the nucleotide sequence set forth in SEQ ID NO: 45, and a polynucleotide encoding a VL, having the nucleotide sequence set forth in SEQ ID NO: 47; or
 (b) a polynucleotide encoding a VH, having the nucleotide sequence set forth in SEQ ID NO: 49, and a polynucleotide encoding a VL, having the nucleotide sequence set forth in SEQ ID NO: 51.

11. A method for manufacturing a cell for treating or preventing a disease, disorder, or condition caused by an antigen that is not derived from a subject, comprising mixing the antibody or variant thereof of claim 1, a cell derived from the subject, and an antigen that is not derived from the subject or a material containing the antigen.

12. The method of claim 11, wherein the disease, disorder, or condition is selected from the group consisting of graft rejection, allergy, autoimmune disease, graft-versus-host disease, and immune rejection caused by transplantation of an iPS cell or an ES cell and a cell, tissue, or organ derived from said cells.

13. The method of claim 11, wherein the material containing the antigen is a cell.

14. A composition, comprising:
 (a) a first antibody that is the antibody or variant thereof of claim 1 which comprises a heavy chain having the amino acid sequence of SEQ ID NO: 38 and a light chain having the amino acid sequence of SEQ ID NO: 40; and (b) a second antibody that is the antibody or variant thereof of claim 1 which comprises a heavy chain having the amino acid sequence of SEQ ID NO: 42 and a light chain having the amino acid sequence of SEQ ID NO: 44.

* * * * *

UNITED STATES PATENT AND TRADEMARK OFFICE
CERTIFICATE OF CORRECTION

| | | |
|---|---|---|
| PATENT NO. | : 12,139,537 B2 | Page 1 of 1 |
| APPLICATION NO. | : 17/254006 | |
| DATED | : November 12, 2024 | |
| INVENTOR(S) | : Ryu Maeda et al. | |

It is certified that error appears in the above-identified patent and that said Letters Patent is hereby corrected as shown below:

In the Claims

Column 111, Claim 4, Line 43:
"from a subject: does not" should read: --from a subject; does not--.

Column 111, Claim 4, Lines 44-45:
"immunostimulation: reduces" should read: --immunostimulation; reduces--.

Column 112, Claim 5, Line 18:
"sequence thereof, or" should read: --sequence thereof; or--.

Signed and Sealed this
Twenty-first Day of January, 2025

Coke Morgan Stewart
*Acting Director of the United States Patent and Trademark Office*

SEQUENCE LISTING

<160> NUMBER OF SEQ ID NOS: 64

<210> SEQ ID NO 1
<211> LENGTH: 1347
<212> TYPE: DNA
<213> ORGANISM: Artificial Sequence
<220> FEATURE:
<223> OTHER INFORMATION: antibody
<220> FEATURE:
<221> NAME/KEY: CDS
<222> LOCATION: (1)..(1347)

<400> SEQUENCE: 1

```
gag gtg cag ttg gtt gaa tct ggc gga gga ctg gtt cag cct ggc gga      48
Glu Val Gln Leu Val Glu Ser Gly Gly Gly Leu Val Gln Pro Gly Gly
1               5                   10                  15 tct ctg aga ctg tct tgt gcc gcc tct ggc ttc gtg ttc agc tcc gac      96
Ser Leu Arg Leu Ser Cys Ala Ala Ser Gly Phe Val Phe Ser Ser Asp
            20                  25                  30 gat atg tcc tgg gtc cga cag gct cct ggc aaa gga ttg gag tgg gtc     144
Asp Met Ser Trp Val Arg Gln Ala Pro Gly Lys Gly Leu Glu Trp Val
        35                  40                  45 gcc tac atc tct tct ggc ggc gac tac acc tac tat ccc gac acc gtg     192
Ala Tyr Ile Ser Ser Gly Gly Asp Tyr Thr Tyr Tyr Pro Asp Thr Val
    50                  55                  60 aag ggc aga ttc acc atc tcc aga gac aac gcc aag aac tcc ctg tac     240
Lys Gly Arg Phe Thr Ile Ser Arg Asp Asn Ala Lys Asn Ser Leu Tyr
65                  70                  75                  80 ctg cag atg aac agc ctg aga gcc gag gac acc gcc gtg tac tac tgt     288
Leu Gln Met Asn Ser Leu Arg Ala Glu Asp Thr Ala Val Tyr Tyr Cys
                85                  90                  95 gcc aga cac ctg tac ggc tcc tcc agc tac tac gtg atg gac tat tgg     336
Ala Arg His Leu Tyr Gly Ser Ser Ser Tyr Tyr Val Met Asp Tyr Trp
            100                 105                 110 ggc cag ggc acc ctg gtc aca gtg tcc tct gct tcc acc aag gga ccc     384
Gly Gln Gly Thr Leu Val Thr Val Ser Ser Ala Ser Thr Lys Gly Pro
        115                 120                 125 agc gtt ttc cct ctg gct cct tgc tcc aga tcc acc tcc gag tct aca     432
Ser Val Phe Pro Leu Ala Pro Cys Ser Arg Ser Thr Ser Glu Ser Thr
    130                 135                 140 gct gct ctg ggc tgc ctg gtc aag gac tac ttt cct gag cct gtg acc     480
Ala Ala Leu Gly Cys Leu Val Lys Asp Tyr Phe Pro Glu Pro Val Thr
145                 150                 155                 160 gtg tcc tgg aac tct ggc gct ctg aca tct ggc gtg cac acc ttt cca     528
Val Ser Trp Asn Ser Gly Ala Leu Thr Ser Gly Val His Thr Phe Pro
                165                 170                 175 gct gtg ctg cag tcc tct ggc ctg tac tct ctg tcc tcc gtc gtg acc     576
Ala Val Leu Gln Ser Ser Gly Leu Tyr Ser Leu Ser Ser Val Val Thr
            180                 185                 190 gtg cct tcc tct aac ttt ggc acc cag acc tac acc tgt aat gtg gac     624
Val Pro Ser Ser Asn Phe Gly Thr Gln Thr Tyr Thr Cys Asn Val Asp
        195                 200                 205 cac aag cct tcc aac acc aag gtg gac aag acc gtg gaa cgg aag tgc     672
His Lys Pro Ser Asn Thr Lys Val Asp Lys Thr Val Glu Arg Lys Cys
    210                 215                 220 tgc gtg gaa tgc cct cct tgt cct gct cct cct gtg gct ggc cct tcc     720
Cys Val Glu Cys Pro Pro Cys Pro Ala Pro Pro Val Ala Gly Pro Ser
225                 230                 235                 240 gtg ttt ctg ttc cct cca aag cct aag gac acc ctg atg atc tct cgg     768
Val Phe Leu Phe Pro Pro Lys Pro Lys Asp Thr Leu Met Ile Ser Arg
                245                 250                 255
```

```
acc cct gaa gtg acc tgc gtg gtg gtg gat gtg tct cac gag gat ccc    816
Thr Pro Glu Val Thr Cys Val Val Val Asp Val Ser His Glu Asp Pro
        260                 265                 270 gaa gtg cag ttc aat tgg tac gtg gac ggc gtg gaa gtg cac aac gcc    864
Glu Val Gln Phe Asn Trp Tyr Val Asp Gly Val Glu Val His Asn Ala
    275                 280                 285 aag acc aag cct aga gag gaa cag ttc aac tcc acc ttc aga gtg gtg    912
Lys Thr Lys Pro Arg Glu Glu Gln Phe Asn Ser Thr Phe Arg Val Val
290                 295                 300 tcc gtg ctg acc gtg gtg cat cag gat tgg ctg aac ggc aaa gag tac    960
Ser Val Leu Thr Val Val His Gln Asp Trp Leu Asn Gly Lys Glu Tyr
305                 310                 315                 320 aag tgc aag gtg tcc aac aag ggc ctg cct gct cct atc gaa aag acc   1008
Lys Cys Lys Val Ser Asn Lys Gly Leu Pro Ala Pro Ile Glu Lys Thr
                325                 330                 335 atc tct aag acc aag ggg cag ccc cgg gaa cct cag gtt tac aca ctg   1056
Ile Ser Lys Thr Lys Gly Gln Pro Arg Glu Pro Gln Val Tyr Thr Leu
            340                 345                 350 cct cca agc cgg gaa gag atg acc aag aac cag gtg tcc ctg acc tgc   1104
Pro Pro Ser Arg Glu Glu Met Thr Lys Asn Gln Val Ser Leu Thr Cys
        355                 360                 365 ctc gtg aag ggc ttc tac cct tcc gat atc gcc gtg gaa tgg gag agc   1152
Leu Val Lys Gly Phe Tyr Pro Ser Asp Ile Ala Val Glu Trp Glu Ser
    370                 375                 380 aat ggc cag cct gag aac aac tac aag acc aca cct cct atg ctg gac   1200
Asn Gly Gln Pro Glu Asn Asn Tyr Lys Thr Thr Pro Pro Met Leu Asp
385                 390                 395                 400 tcc gac ggc tca ttc ttc ctg tac tcc aag ctg aca gtg gac aag tcc   1248
Ser Asp Gly Ser Phe Phe Leu Tyr Ser Lys Leu Thr Val Asp Lys Ser
                405                 410                 415 aga tgg cag cag ggc aac gtg ttc tcc tgc tcc gtg atg cac gag gcc   1296
Arg Trp Gln Gln Gly Asn Val Phe Ser Cys Ser Val Met His Glu Ala
            420                 425                 430 ctg cac aat cac tac acc cag aag tcc ctg tct ctg tcc cct ggc aaa   1344
Leu His Asn His Tyr Thr Gln Lys Ser Leu Ser Leu Ser Pro Gly Lys
        435                 440                 445 tga                                                               1347

<210> SEQ ID NO 2
<211> LENGTH: 448
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Asp
            20                  25                  30

Asp Met Ser Trp Val Arg Gln Ala Pro Gly Lys Gly Leu Glu Trp Val
        35                  40                  45

Ala Tyr Ile Ser Ser Gly Gly Asp Tyr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Ser Ser Ser Tyr Tyr Val Met Asp Tyr Trp
```

|  |  |  | 100 |  |  |  | 105 |  |  |  | 110 |  |
|---|---|---|---|---|---|---|---|---|---|---|---|---|

Gly Gln Gly Thr Leu Val Thr Val Ser Ser Ala Ser Thr Lys Gly Pro
            115                      120                  125

Ser Val Phe Pro Leu Ala Pro Cys Ser Arg Ser Thr Ser Glu Ser Thr
130                      135                      140

Ala Ala Leu Gly Cys Leu Val Lys Asp Tyr Phe Pro Glu Pro Val Thr
145                      150                      155                      160

Val Ser Trp Asn Ser Gly Ala Leu Thr Ser Gly Val His Thr Phe Pro
            165                      170                  175

Ala Val Leu Gln Ser Ser Gly Leu Tyr Ser Leu Ser Ser Val Val Thr
            180                      185                  190

Val Pro Ser Ser Asn Phe Gly Thr Gln Thr Tyr Thr Cys Asn Val Asp
            195                      200                  205

His Lys Pro Ser Asn Thr Lys Val Asp Lys Thr Val Glu Arg Lys Cys
            210                      215                  220

Cys Val Glu Cys Pro Pro Cys Pro Ala Pro Pro Val Ala Gly Pro Ser
225                      230                      235                      240

Val Phe Leu Phe Pro Pro Lys Pro Lys Asp Thr Leu Met Ile Ser Arg
            245                      250                  255

Thr Pro Glu Val Thr Cys Val Val Asp Val Ser His Glu Asp Pro
                260                      265                  270

Glu Val Gln Phe Asn Trp Tyr Val Asp Gly Val Glu Val His Asn Ala
            275                      280                  285

Lys Thr Lys Pro Arg Glu Glu Gln Phe Asn Ser Thr Phe Arg Val Val
            290                      295                  300

Ser Val Leu Thr Val Val His Gln Asp Trp Leu Asn Gly Lys Glu Tyr
305                      310                      315                      320

Lys Cys Lys Val Ser Asn Lys Gly Leu Pro Ala Pro Ile Glu Lys Thr
            325                      330                  335

Ile Ser Lys Thr Lys Gly Gln Pro Arg Glu Pro Gln Val Tyr Thr Leu
            340                      345                  350

Pro Pro Ser Arg Glu Glu Met Thr Lys Asn Gln Val Ser Leu Thr Cys
            355                      360                  365

Leu Val Lys Gly Phe Tyr Pro Ser Asp Ile Ala Val Glu Trp Glu Ser
            370                      375                  380

Asn Gly Gln Pro Glu Asn Asn Tyr Lys Thr Thr Pro Pro Met Leu Asp
385                      390                      395                      400

Ser Asp Gly Ser Phe Phe Leu Tyr Ser Lys Leu Thr Val Asp Lys Ser
            405                      410                  415

Arg Trp Gln Gln Gly Asn Val Phe Ser Cys Ser Val Met His Glu Ala
            420                      425                  430

Leu His Asn His Tyr Thr Gln Lys Ser Leu Ser Leu Ser Pro Gly Lys
            435                      440                  445

```
<210> SEQ ID NO 3
<211> LENGTH: 645
<212> TYPE: DNA
<213> ORGANISM: Artificial Sequence
<220> FEATURE:
<223> OTHER INFORMATION: andibody
<220> FEATURE:
<221> NAME/KEY: CDS
<222> LOCATION: (1)..(645)

<400> SEQUENCE: 3 gac atc cag atg acc cag tct cca tcc tct ctg tct gcc agc ctg ggc        48
```

```
                                        -continued

Asp Ile Gln Met Thr Gln Ser Pro Ser Ser Leu Ser Ala Ser Leu Gly
1               5                   10                  15 gac aga atc acc atc acc tgt cac gcc agc cag aac atc aac gtg tgg       96
Asp Arg Ile Thr Ile Thr Cys His Ala Ser Gln Asn Ile Asn Val Trp
            20                  25                  30 ctg tcc tgg tat cag cag aag ccc ggc aag atc ccc aag ctg ctg gtg      144
Leu Ser Trp Tyr Gln Gln Lys Pro Gly Lys Ile Pro Lys Leu Leu Val
        35                  40                  45 tac aag gcc tcc aat ctg cac acc ggc gtg ccc tct aga ttc tcc gga      192
Tyr Lys Ala Ser Asn Leu His Thr Gly Val Pro Ser Arg Phe Ser Gly
    50                  55                  60 tct ggc tct ggc acc gac ttt acc ctg aca atc tcc agc ctg cag cct      240
Ser Gly Ser Gly Thr Asp Phe Thr Leu Thr Ile Ser Ser Leu Gln Pro
65                  70                  75                  80 gag gac ttc gcc acc tac tat tgt cag cag ggc cag agc tac cct ctg      288
Glu Asp Phe Ala Thr Tyr Tyr Cys Gln Gln Gly Gln Ser Tyr Pro Leu
                85                  90                  95 acc ttt ggc gct ggc acc aag ctg gaa atc aag cgg aca gtg gcc gct      336
Thr Phe Gly Ala Gly Thr Lys Leu Glu Ile Lys Arg Thr Val Ala Ala
            100                 105                 110 cct tcc gtg ttc atc ttc cca cct tcc gac gag cag ctg aag tcc ggc      384
Pro Ser Val Phe Ile Phe Pro Pro Ser Asp Glu Gln Leu Lys Ser Gly
        115                 120                 125 aca gct tct gtc gtg tgc ctg ctg aac aac ttc tac cct cgg gaa gcc      432
Thr Ala Ser Val Val Cys Leu Leu Asn Asn Phe Tyr Pro Arg Glu Ala
    130                 135                 140 aag gtg cag tgg aag gtg gac aat gcc ctg cag tcc ggc aac tcc caa      480
Lys Val Gln Trp Lys Val Asp Asn Ala Leu Gln Ser Gly Asn Ser Gln
145                 150                 155                 160 gag tct gtg acc gag cag gac tcc aag gac agc acc tac agc ctg tcc      528
Glu Ser Val Thr Glu Gln Asp Ser Lys Asp Ser Thr Tyr Ser Leu Ser
                165                 170                 175 tcc aca ctg acc ctg tcc aag gcc gac tac gag aag cac aag gtg tac      576
Ser Thr Leu Thr Leu Ser Lys Ala Asp Tyr Glu Lys His Lys Val Tyr
            180                 185                 190 gcc tgc gaa gtg acc cat cag ggc ctg tct agc cct gtg acc aag tct      624
Ala Cys Glu Val Thr His Gln Gly Leu Ser Ser Pro Val Thr Lys Ser
        195                 200                 205 ttc aac cgg ggc gag tgc tga                                          645
Phe Asn Arg Gly Glu Cys
    210

<210> SEQ ID NO 4
<211> LENGTH: 214
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Leu Gly
1               5                   10                  15

Asp Arg Ile Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Val
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Gln Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 1350
<212> TYPE: DNA
<213> ORGANISM: Artificial Sequence
<220> FEATURE:
<223> OTHER INFORMATION: antibody
<220> FEATURE:
<221> NAME/KEY: CDS
<222> LOCATION: (1)..(1350)

<400> SEQUENCE: 5 gag gtg cag ttg gtt gaa tct ggc gga gga ctg gtt cag cct ggc gga        48
Glu Val Gln Leu Val Glu Ser Gly Gly Gly Leu Val Gln Pro Gly Gly
1               5                   10                  15 tct ctg aga ctg tct tgt gcc gcc tct ggc ttc gtg ttc agc tcc gac       96
Ser Leu Arg Leu Ser Cys Ala Ala Ser Gly Phe Val Phe Ser Ser Asp
            20                  25                  30 gat atg tcc tgg gtc cga cag gct cct ggc aaa gga ttg gag tgg gtc      144
Asp Met Ser Trp Val Arg Gln Ala Pro Gly Lys Gly Leu Glu Trp Val
        35                  40                  45 gcc tac atc tct tct ggc ggc gac tac acc tac tat ccc gac acc gtg      192
Ala Tyr Ile Ser Ser Gly Gly Asp Tyr Thr Tyr Tyr Pro Asp Thr Val
    50                  55                  60 aag ggc aga ttc acc atc tcc aga gac aac gcc aag aac tcc ctg tac      240
Lys Gly Arg Phe Thr Ile Ser Arg Asp Asn Ala Lys Asn Ser Leu Tyr
65                  70                  75                  80 ctg cag atg aac agc ctg aga gcc gag gac acc gcc gtg tac tac tgt      288
Leu Gln Met Asn Ser Leu Arg Ala Glu Asp Thr Ala Val Tyr Tyr Cys
                85                  90                  95 gcc aga cac ctg tac ggc tcc tcc agc tac tac gtg atg gac tat tgg      336
Ala Arg His Leu Tyr Gly Ser Ser Ser Tyr Tyr Val Met Asp Tyr Trp
            100                 105                 110 ggc cag ggc acc ctg gtc aca gtg tcc tct gct tct acc aag ggc ccc      384
Gly Gln Gly Thr Leu Val Thr Val Ser Ser Ala Ser Thr Lys Gly Pro
        115                 120                 125 tcc gtg ttc cct ctg gcc cct tgc tcc aga tcc acc tcc gag tct acc      432
Ser Val Phe Pro Leu Ala Pro Cys Ser Arg Ser Thr Ser Glu Ser Thr
    130                 135                 140 gcc gct ctg ggc tgc ctc gtg aag gac tac ttc ccc gag ccc gtg aca      480
Ala Ala Leu Gly Cys Leu Val Lys Asp Tyr Phe Pro Glu Pro Val Thr
```

|   |   |   |   |   |   |   |   |   |   |   |   | |
|---|---|---|---|---|---|---|---|---|---|---|---|---|
| 145 | | | | 150 | | | | 155 | | | 160 | |
| gtg | tcc | tgg | aac | tct | ggc | gct | ctg | acc | tcc | ggc | gtg cac acc ttt cca | 528 |
| Val | Ser | Trp | Asn | Ser | Gly | Ala | Leu | Thr | Ser | Gly | Val His Thr Phe Pro | |
| | | | | 165 | | | | 170 | | | 175 | |
| gca | gtg | ctg | cag | tcc | tcc | ggc | ctg | tac | tcc | ctg | tcc gtc gtg act | 576 |
| Ala | Val | Leu | Gln | Ser | Ser | Gly | Leu | Tyr | Ser | Leu | Ser Val Val Thr | |
| | | 180 | | | | | 185 | | | | 190 | |
| gtg | ccc | tcc | agc | tct | ctg | ggc | acc | aag | acc | tac | acc tgt aac gtg gac | 624 |
| Val | Pro | Ser | Ser | Ser | Leu | Gly | Thr | Lys | Thr | Tyr | Thr Cys Asn Val Asp | |
| | | | 195 | | | | | 200 | | | 205 | |
| cac | aag | ccc | tcc | aac | acc | aag | gtg | gac | aag | aga | gtg gaa tct aag tac | 672 |
| His | Lys | Pro | Ser | Asn | Thr | Lys | Val | Asp | Lys | Arg | Val Glu Ser Lys Tyr | |
| | 210 | | | | | 215 | | | | 220 | | |
| ggc | cct | ccc | tgc | ccc | cct | tgt | cct | gcc | cct | gaa | ttt ctg ggc gga ccc | 720 |
| Gly | Pro | Pro | Cys | Pro | Pro | Cys | Pro | Ala | Pro | Glu | Phe Leu Gly Gly Pro | |
| 225 | | | | 230 | | | | 235 | | | 240 | |
| agc | gtg | ttc | ctg | ttc | ccc | cca | aag | ccc | aag | gac | acc ctg atg atc tcc | 768 |
| Ser | Val | Phe | Leu | Phe | Pro | Pro | Lys | Pro | Lys | Asp | Thr Leu Met Ile Ser | |
| | | | | 245 | | | | 250 | | | 255 | |
| cgg | acc | ccc | gaa | gtg | acc | tgc | gtg | gtg | gtg | gat | gtg tcc cag gaa gat | 816 |
| Arg | Thr | Pro | Glu | Val | Thr | Cys | Val | Val | Val | Asp | Val Ser Gln Glu Asp | |
| | | | 260 | | | | | 265 | | | 270 | |
| ccc | gag | gtg | cag | ttc | aat | tgg | tac | gtg | gac | ggc | gtg gaa gtg cac aac | 864 |
| Pro | Glu | Val | Gln | Phe | Asn | Trp | Tyr | Val | Asp | Gly | Val Glu Val His Asn | |
| | 275 | | | | | 280 | | | | 285 | | |
| gcc | aag | acc | aag | cct | aga | gag | gaa | cag | ttc | aac | tcc acc tac cgg gtg | 912 |
| Ala | Lys | Thr | Lys | Pro | Arg | Glu | Glu | Gln | Phe | Asn | Ser Thr Tyr Arg Val | |
| | 290 | | | | | 295 | | | | 300 | | |
| gtg | tcc | gtg | ctg | acc | gtg | ctg | cac | cag | gat | tgg | ctg aac ggc aaa gag | 960 |
| Val | Ser | Val | Leu | Thr | Val | Leu | His | Gln | Asp | Trp | Leu Asn Gly Lys Glu | |
| 305 | | | | 310 | | | | 315 | | | 320 | |
| tac | aag | tgc | aag | gtg | tcc | aac | aag | ggc | ctg | ccc | agc tcc atc gaa aag | 1008 |
| Tyr | Lys | Cys | Lys | Val | Ser | Asn | Lys | Gly | Leu | Pro | Ser Ser Ile Glu Lys | |
| | | | 325 | | | | | 330 | | | 335 | |
| acc | atc | tcc | aag | gcc | aag | ggc | cag | ccc | cgg | gaa | ccc cag gtg tac aca | 1056 |
| Thr | Ile | Ser | Lys | Ala | Lys | Gly | Gln | Pro | Arg | Glu | Pro Gln Val Tyr Thr | |
| | | 340 | | | | | 345 | | | | 350 | |
| ctg | cct | cca | agc | cag | gaa | gag | atg | acc | aag | aac | cag gtg tcc ctg acc | 1104 |
| Leu | Pro | Pro | Ser | Gln | Glu | Glu | Met | Thr | Lys | Asn | Gln Val Ser Leu Thr | |
| | | 355 | | | | | 360 | | | | 365 | |
| tgt | ctc | gtg | aaa | ggc | ttc | tac | ccc | tcc | gat | atc | gcc gtg gaa tgg gag | 1152 |
| Cys | Leu | Val | Lys | Gly | Phe | Tyr | Pro | Ser | Asp | Ile | Ala Val Glu Trp Glu | |
| | 370 | | | | | 375 | | | | 380 | | |
| tcc | aac | ggc | cag | cct | gag | aac | aac | tac | aag | acc | acc ccc cct gtg ctg | 1200 |
| Ser | Asn | Gly | Gln | Pro | Glu | Asn | Asn | Tyr | Lys | Thr | Thr Pro Pro Val Leu | |
| 385 | | | | 390 | | | | 395 | | | 400 | |
| gac | tcc | gac | ggc | tcc | ttc | ttc | ctg | tac | tct | cgc | ctg acc gtg gac aag | 1248 |
| Asp | Ser | Asp | Gly | Ser | Phe | Phe | Leu | Tyr | Ser | Arg | Leu Thr Val Asp Lys | |
| | | | 405 | | | | | 410 | | | 415 | |
| tcc | cgg | tgg | cag | gaa | ggc | aac | gtg | ttc | tcc | tgc | tcc gtg atg cac gag | 1296 |
| Ser | Arg | Trp | Gln | Glu | Gly | Asn | Val | Phe | Ser | Cys | Ser Val Met His Glu | |
| | | 420 | | | | | 425 | | | | 430 | |
| gcc | ctg | cac | aac | cac | tac | acc | cag | aag | tcc | ctg | tct ctg tcc ctg ggc | 1344 |
| Ala | Leu | His | Asn | His | Tyr | Thr | Gln | Lys | Ser | Leu | Ser Leu Ser Leu Gly | |
| | | 435 | | | | | 440 | | | | 445 | |
| aag | tga | | | | | | | | | | | 1350 |
| Lys | | | | | | | | | | | | |

<210> SEQ ID NO 6

<211> LENGTH: 449
<212> TYPE: PRT
<213> ORGANISM: Artificial Sequence
<220> FEATURE:
<223> OTHER INFORMATION: Synthetic Construct

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Asp
            20                  25                  30

Asp Met Ser Trp Val Arg Gln Ala Pro Gly Lys Gly Leu Glu Trp Val
        35                  40                  45

Ala Tyr Ile Ser Ser Gly Gly Asp Tyr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Ser Ser Tyr Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 7
<211> LENGTH: 645
<212> TYPE: DNA
<213> ORGANISM: Artificial Sequence
<220> FEATURE:
<223> OTHER INFORMATION: antibody
<220> FEATURE:
<221> NAME/KEY: CDS
<222> LOCATION: (1)..(645)

<400> SEQUENCE: 7 gac atc cag atg acc cag tct cca tcc tct ctg tct gcc agc ctg ggc     48
Asp Ile Gln Met Thr Gln Ser Pro Ser Ser Leu Ser Ala Ser Leu Gly
1               5                   10                  15 gac aga atc acc atc acc tgt cac gcc agc cag aac atc aac gtg tgg     96
Asp Arg Ile Thr Ile Thr Cys His Ala Ser Gln Asn Ile Asn Val Trp
            20                  25                  30 ctg tcc tgg tat cag cag aag ccc ggc aag atc ccc aag ctg ctg gtg    144
Leu Ser Trp Tyr Gln Gln Lys Pro Gly Lys Ile Pro Lys Leu Leu Val
        35                  40                  45 tac aag gcc tcc aat ctg cac acc ggc gtg ccc tct aga ttc tcc gga    192
Tyr Lys Ala Ser Asn Leu His Thr Gly Val Pro Ser Arg Phe Ser Gly
    50                  55                  60 tct ggc tct ggc acc gac ttt acc ctg aca atc tcc agc ctg cag cct    240
Ser Gly Ser Gly Thr Asp Phe Thr Leu Thr Ile Ser Ser Leu Gln Pro
65                  70                  75                  80 gag gac ttc gcc acc tac tat tgt cag cag ggc cag agc tac cct ctg    288
Glu Asp Phe Ala Thr Tyr Tyr Cys Gln Gln Gly Gln Ser Tyr Pro Leu
                85                  90                  95 acc ttt ggc gct ggc acc aag ctg gaa atc aag cgg aca gtg gcc gct    336
Thr Phe Gly Ala Gly Thr Lys Leu Glu Ile Lys Arg Thr Val Ala Ala
            100                 105                 110 cct tcc gtg ttc atc ttc cca cct tcc gac gag cag ctg aag tcc ggc    384
Pro Ser Val Phe Ile Phe Pro Pro Ser Asp Glu Gln Leu Lys Ser Gly
        115                 120                 125 aca gct tct gtc gtg tgc ctg ctg aac aac ttc tac cct cgg gaa gcc    432
Thr Ala Ser Val Val Cys Leu Leu Asn Asn Phe Tyr Pro Arg Glu Ala
    130                 135                 140 aag gtg cag tgg aag gtg gac aat gcc ctg cag tcc ggc aac tcc caa    480
Lys Val Gln Trp Lys Val Asp Asn Ala Leu Gln Ser Gly Asn Ser Gln
145                 150                 155                 160 gag tct gtg acc gag cag gac tcc aag gac agc acc tac agc ctg tcc    528
Glu Ser Val Thr Glu Gln Asp Ser Lys Asp Ser Thr Tyr Ser Leu Ser
                165                 170                 175 tcc aca ctg acc ctg tcc aag gcc gac tac gag aag cac aag gtg tac    576
Ser Thr Leu Thr Leu Ser Lys Ala Asp Tyr Glu Lys His Lys Val Tyr
            180                 185                 190 gcc tgc gaa gtg acc cat cag ggc ctg tct agc cct gtg acc aag tct    624
Ala Cys Glu Val Thr His Gln Gly Leu Ser Ser Pro Val Thr Lys Ser
        195                 200                 205
```

```
ttc aac cgg ggc gag tgc tga                                              645
Phe Asn Arg Gly Glu Cys
    210

<210> SEQ ID NO 8
<211> LENGTH: 214
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Leu Gly
1               5                   10                  15

Asp Arg Ile Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Val
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 1347
<212> TYPE: DNA
<213> ORGANISM: Artificial Sequence
<220> FEATURE:
<223> OTHER INFORMATION: antibody
<220> FEATURE:
<221> NAME/KEY: CDS
<222> LOCATION: (1)..(1347)

<400> SEQUENCE: 9 cag gtg cag ttg gtt cag tct ggc gcc gaa gtg aag aaa cct ggc gcc   48
Gln Val Gln Leu Val Gln Ser Gly Ala Glu Val Lys Lys Pro Gly Ala
1               5                   10                  15 tct gtg aag gtg tcc tgc aag gct tcc ggc tac acc ttt acc agc tac   96
Ser Val Lys Val Ser Cys Lys Ala Ser Gly Tyr Thr Phe Thr Ser Tyr
            20                  25                  30 gtg atc cac tgg gtc cga cag gct cca gga caa ggc ttg gag tgg atg  144
```

```
                Val Ile His Trp Val Arg Gln Ala Pro Gly Gln Gly Leu Glu Trp Met
                         35                  40                  45 ggc tac atc aac ccc tac cac gac gtg acc aag tac aac gag aag ttc         192
Gly Tyr Ile Asn Pro Tyr His Asp Val Thr Lys Tyr Asn Glu Lys Phe
         50                  55                  60 cag ggc aga gtg acc atg acc aga gac acc tcc acc agc acc gtg tac         240
Gln Gly Arg Val Thr Met Thr Arg Asp Thr Ser Thr Ser Thr Val Tyr
 65                  70                  75                  80 atg gaa ctg tcc agc ctg aga tcc gag gac acc gcc gtg tac tac tgc         288
Met Glu Leu Ser Ser Leu Arg Ser Glu Asp Thr Ala Val Tyr Tyr Cys
                     85                  90                  95 gcc aga cag ggc gac cct tac tcc ggc aac tac cag ttt acc tac tgg         336
Ala Arg Gln Gly Asp Pro Tyr Ser Gly Asn Tyr Gln Phe Thr Tyr Trp
                100                 105                 110 ggc cag ggc acc ctg gtc aca gtt tct tcc gct tcc acc aag gga ccc         384
Gly Gln Gly Thr Leu Val Thr Val Ser Ser Ala Ser Thr Lys Gly Pro
            115                 120                 125 agc gtt ttc cct ctg gct cct tgc tcc aga tcc acc tcc gag tct aca         432
Ser Val Phe Pro Leu Ala Pro Cys Ser Arg Ser Thr Ser Glu Ser Thr
        130                 135                 140 gct gct ctg ggc tgc ctg gtc aag gac tac ttt cct gag cct gtg acc         480
Ala Ala Leu Gly Cys Leu Val Lys Asp Tyr Phe Pro Glu Pro Val Thr
145                 150                 155                 160 gtg tcc tgg aac tct ggc gct ctg aca tct ggc gtg cac acc ttt cca         528
Val Ser Trp Asn Ser Gly Ala Leu Thr Ser Gly Val His Thr Phe Pro
                165                 170                 175 gct gtg ctg cag tcc tct ggc ctg tac tct ctg tcc tcc gtc gtg acc         576
Ala Val Leu Gln Ser Ser Gly Leu Tyr Ser Leu Ser Ser Val Val Thr
            180                 185                 190 gtg cct tcc tct aac ttt ggc acc cag acc tac acc tgt aat gtg gac         624
Val Pro Ser Ser Asn Phe Gly Thr Gln Thr Tyr Thr Cys Asn Val Asp
        195                 200                 205 cac aag cct tcc aac acc aag gtg gac aag acc gtg gaa cgg aag tgc         672
His Lys Pro Ser Asn Thr Lys Val Asp Lys Thr Val Glu Arg Lys Cys
    210                 215                 220 tgc gtg gaa tgc cct cct tgt cct gct cct cct gtg gct ggc cct tcc         720
Cys Val Glu Cys Pro Pro Cys Pro Ala Pro Pro Val Ala Gly Pro Ser
225                 230                 235                 240 gtg ttt ctg ttc cct cca aag cct aag gac acc ctg atg atc tct cgg         768
Val Phe Leu Phe Pro Pro Lys Pro Lys Asp Thr Leu Met Ile Ser Arg
                245                 250                 255 acc cct gaa gtg acc tgc gtg gtg gtg gat gtg tct cac gag gat ccc         816
Thr Pro Glu Val Thr Cys Val Val Val Asp Val Ser His Glu Asp Pro
            260                 265                 270 gaa gtg cag ttc aat tgg tac gtg gac ggc gtg gaa gtg cac aac gcc         864
Glu Val Gln Phe Asn Trp Tyr Val Asp Gly Val Glu Val His Asn Ala
        275                 280                 285 aag acc aag cct aga gag gaa cag ttc aac tcc acc ttc aga gtg gtg         912
Lys Thr Lys Pro Arg Glu Glu Gln Phe Asn Ser Thr Phe Arg Val Val
    290                 295                 300 tcc gtg ctg acc gtg gtg cat cag gat tgg ctg aac ggc aaa gag tac         960
Ser Val Leu Thr Val Val His Gln Asp Trp Leu Asn Gly Lys Glu Tyr
305                 310                 315                 320 aag tgc aag gtg tcc aac aag ggc ctg cct gct cct atc gaa aag acc        1008
Lys Cys Lys Val Ser Asn Lys Gly Leu Pro Ala Pro Ile Glu Lys Thr
                325                 330                 335 atc tct aag acc aag ggg cag ccc cgg gaa cct cag gtt tac aca ctg        1056
Ile Ser Lys Thr Lys Gly Gln Pro Arg Glu Pro Gln Val Tyr Thr Leu
            340                 345                 350
```

| | | |
|---|---|---|
| cct cca agc cgg gaa gag atg acc aag aac cag gtg tcc ctg acc tgc<br>Pro Pro Ser Arg Glu Glu Met Thr Lys Asn Gln Val Ser Leu Thr Cys<br>355 360 365 | | 1104 |
| ctc gtg aag ggc ttc tac cct tcc gat atc gcc gtg gaa tgg gag agc<br>Leu Val Lys Gly Phe Tyr Pro Ser Asp Ile Ala Val Glu Trp Glu Ser<br>370 375 380 | | 1152 |
| aat ggc cag cct gag aac aac tac aag acc aca cct cct atg ctg gac<br>Asn Gly Gln Pro Glu Asn Asn Tyr Lys Thr Thr Pro Pro Met Leu Asp<br>385 390 395 400 | | 1200 |
| tcc gac ggc tca ttc ttc ctg tac tcc aag ctg aca gtg gac aag tcc<br>Ser Asp Gly Ser Phe Phe Leu Tyr Ser Lys Leu Thr Val Asp Lys Ser<br>405 410 415 | | 1248 |
| aga tgg cag cag ggc aac gtg ttc tcc tgc tcc gtg atg cac gag gcc<br>Arg Trp Gln Gln Gly Asn Val Phe Ser Cys Ser Val Met His Glu Ala<br>420 425 430 | | 1296 |
| ctg cac aat cac tac acc cag aag tcc ctg tct ctg tcc cct ggc aaa<br>Leu His Asn His Tyr Thr Gln Lys Ser Leu Ser Leu Ser Pro Gly Lys<br>435 440 445 | | 1344 |
| tga | | 1347 |

<210> SEQ ID NO 10
<211> LENGTH: 448
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Ile His Trp Val Arg Gln Ala Pro Gly Gln Gly Leu Glu Trp Met
            35                  40                  45

Gly Tyr Ile Asn Pro Tyr His Asp Val Thr Lys Tyr Asn Glu Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Gly Asp Pro Tyr Ser Gly Asn Tyr Gln Phe Thr Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser

```
                   225                 230                 235                 240
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 11
<211> LENGTH: 645
<212> TYPE: DNA
<213> ORGANISM: Artificial Sequence
<220> FEATURE:
<223> OTHER INFORMATION: antibody
<220> FEATURE:
<221> NAME/KEY: CDS
<222> LOCATION: (1)..(645)

<400> SEQUENCE: 11 gac atc cag atg acc cag tct cca tcc tct ctg tcc gcc tct gtg ggc      48
Asp Ile Gln Met Thr Gln Ser Pro Ser Ser Leu Ser Ala Ser Val Gly
1               5                   10                  15 gac aga gtg acc atc acc tgt aga gcc tct cag gac gtg tcc acc gag      96
Asp Arg Val Thr Ile Thr Cys Arg Ala Ser Gln Asp Val Ser Thr Glu
            20                  25                  30 gtc gtg tgg tat cag cag aag cct ggc aag gcc cct aag ctg ctg atc     144
Val Val Trp Tyr Gln Gln Lys Pro Gly Lys Ala Pro Lys Leu Leu Ile
        35                  40                  45 tac tcc gcc tcc tac cgg tac tct ggc gtg ccc tct aga ttc tcc ggc     192
Tyr Ser Ala Ser Tyr Arg Tyr Ser Gly Val Pro Ser Arg Phe Ser Gly
    50                  55                  60 tct ggc tct ggc acc gac ttt acc ctg aca atc tcc agc ctg cag cct     240
Ser Gly Ser Gly Thr Asp Phe Thr Leu Thr Ile Ser Ser Leu Gln Pro
65                  70                  75                  80 gag gac ttc gcc acc tac tac tgc cag cag cac tac agc acc cct tac     288
Glu Asp Phe Ala Thr Tyr Tyr Cys Gln Gln His Tyr Ser Thr Pro Tyr
                85                  90                  95 acc ttt ggc cag ggc acc aag ctg gaa atc aag cgg aca gtg gcc gct     336
Thr Phe Gly Gln Gly Thr Lys Leu Glu Ile Lys Arg Thr Val Ala Ala
```

```
Thr Phe Gly Gln Gly Thr Lys Leu Glu Ile Lys Arg Thr Val Ala Ala
            100                 105                 110 cct tcc gtg ttc atc ttc cca cct tcc gac gag cag ctg aag tcc ggc       384
Pro Ser Val Phe Ile Phe Pro Pro Ser Asp Glu Gln Leu Lys Ser Gly
            115                 120                 125 aca gct tct gtc gtg tgc ctg ctg aac aac ttc tac cct cgg gaa gcc       432
Thr Ala Ser Val Val Cys Leu Leu Asn Asn Phe Tyr Pro Arg Glu Ala
        130                 135                 140 aag gtg cag tgg aag gtg gac aat gcc ctg cag tcc ggc aac tcc caa       480
Lys Val Gln Trp Lys Val Asp Asn Ala Leu Gln Ser Gly Asn Ser Gln
145                 150                 155                 160 gag tct gtg acc gag cag gac tcc aag gac agc acc tac agc ctg tcc       528
Glu Ser Val Thr Glu Gln Asp Ser Lys Asp Ser Thr Tyr Ser Leu Ser
                165                 170                 175 tcc aca ctg acc ctg tcc aag gcc gac tac gag aag cac aag gtg tac       576
Ser Thr Leu Thr Leu Ser Lys Ala Asp Tyr Glu Lys His Lys Val Tyr
            180                 185                 190 gcc tgc gaa gtg acc cat cag ggc ctg tct agc cct gtg acc aag tct       624
Ala Cys Glu Val Thr His Gln Gly Leu Ser Ser Pro Val Thr Lys Ser
        195                 200                 205 ttc aac cgg ggc gag tgc tga                                           645
Phe Asn Arg Gly Glu Cys
    210

<210> SEQ ID NO 12
<211> LENGTH: 214
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Glu
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 13
<211> LENGTH: 1350
<212> TYPE: DNA
<213> ORGANISM: Artificial Sequence
<220> FEATURE:
<223> OTHER INFORMATION: andibody
<220> FEATURE:
<221> NAME/KEY: CDS
<222> LOCATION: (1)..(1350)

<400> SEQUENCE: 13

```
cag gtg cag ttg gtt cag tct ggc gcc gaa gtg aag aaa cct ggc gcc        48
Gln Val Gln Leu Val Gln Ser Gly Ala Glu Val Lys Lys Pro Gly Ala
1               5                   10                  15 tct gtg aag gtg tcc tgc aag gct tcc ggc tac acc ttt acc agc tac        96
Ser Val Lys Val Ser Cys Lys Ala Ser Gly Tyr Thr Phe Thr Ser Tyr
            20                  25                  30 gtg atc cac tgg gtc cga cag gct cca gga caa ggc ttg gag tgg atg       144
Val Ile His Trp Val Arg Gln Ala Pro Gly Gln Gly Leu Glu Trp Met
        35                  40                  45 ggc tac atc aac ccc tac cac gac gtg acc aag tac aac gag aag ttc       192
Gly Tyr Ile Asn Pro Tyr His Asp Val Thr Lys Tyr Asn Glu Lys Phe
    50                  55                  60 cag ggc aga gtg acc atg acc aga gac acc tcc acc agc acc gtg tac       240
Gln Gly Arg Val Thr Met Thr Arg Asp Thr Ser Thr Ser Thr Val Tyr
65                  70                  75                  80 atg gaa ctg tcc agc ctg aga tcc gag gac acc gcc gtg tac tac tgc       288
Met Glu Leu Ser Ser Leu Arg Ser Glu Asp Thr Ala Val Tyr Tyr Cys
                85                  90                  95 gcc aga cag ggc gac cct tac tcc ggc aac tac cag ttt acc tac tgg       336
Ala Arg Gln Gly Asp Pro Tyr Ser Gly Asn Tyr Gln Phe Thr Tyr Trp
            100                 105                 110 ggc cag ggc acc ctg gtc aca gtt tct tcc gct tct acc aag ggc ccc       384
Gly Gln Gly Thr Leu Val Thr Val Ser Ser Ala Ser Thr Lys Gly Pro
        115                 120                 125 tcc gtg ttc cct ctg gcc cct tgc tcc aga tcc acc tcc gag tct acc       432
Ser Val Phe Pro Leu Ala Pro Cys Ser Arg Ser Thr Ser Glu Ser Thr
    130                 135                 140 gcc gct ctg ggc tgc ctc gtg aag gac tac ttc ccc gag ccc gtg aca       480
Ala Ala Leu Gly Cys Leu Val Lys Asp Tyr Phe Pro Glu Pro Val Thr
145                 150                 155                 160 gtg tcc tgg aac tct ggc gct ctg acc tcc ggc gtg cac acc ttt cca       528
Val Ser Trp Asn Ser Gly Ala Leu Thr Ser Gly Val His Thr Phe Pro
                165                 170                 175 gca gtg ctg cag tcc tcc ggc ctg tac tcc ctg tcc gtc gtg act           576
Ala Val Leu Gln Ser Ser Gly Leu Tyr Ser Leu Ser Val Val Thr
            180                 185                 190 gtg ccc tcc agc tct ctg ggc acc aag acc tac acc tgt aac gtg gac       624
Val Pro Ser Ser Ser Leu Gly Thr Lys Thr Tyr Thr Cys Asn Val Asp
        195                 200                 205 cac aag ccc tcc aac acc aag gtg gac aag aga gtg gaa tct aag tac       672
His Lys Pro Ser Asn Thr Lys Val Asp Lys Arg Val Glu Ser Lys Tyr
    210                 215                 220 ggc cct ccc tgc ccc cct tgt cct gcc cct gaa ttt ctg ggc gga ccc       720
Gly Pro Pro Cys Pro Pro Cys Pro Ala Pro Glu Phe Leu Gly Gly Pro
225                 230                 235                 240 agc gtg ttc ctg ttc ccc cca aag ccc aag gac acc ctg atg atc tcc       768
Ser Val Phe Leu Phe Pro Pro Lys Pro Lys Asp Thr Leu Met Ile Ser
```

```
                  245                 250                 255
cgg acc ccc gaa gtg acc tgc gtg gtg gtg gat gtg tcc cag gaa gat      816
Arg Thr Pro Glu Val Thr Cys Val Val Val Asp Val Ser Gln Glu Asp
            260                 265                 270 ccc gag gtg cag ttc aat tgg tac gtg gac ggc gtg gaa gtg cac aac      864
Pro Glu Val Gln Phe Asn Trp Tyr Val Asp Gly Val Glu Val His Asn
            275                 280                 285 gcc aag acc aag cct aga gag gaa cag ttc aac tcc acc tac cgg gtg      912
Ala Lys Thr Lys Pro Arg Glu Glu Gln Phe Asn Ser Thr Tyr Arg Val
            290                 295                 300 gtg tcc gtg ctg acc gtg ctg cac cag gat tgg ctg aac ggc aaa gag      960
Val Ser Val Leu Thr Val Leu His Gln Asp Trp Leu Asn Gly Lys Glu
305                 310                 315                 320 tac aag tgc aag gtg tcc aac aag ggc ctg ccc agc tcc atc gaa aag     1008
Tyr Lys Cys Lys Val Ser Asn Lys Gly Leu Pro Ser Ser Ile Glu Lys
                325                 330                 335 acc atc tcc aag gcc aag ggc cag ccc cgg gaa ccc cag gtg tac aca     1056
Thr Ile Ser Lys Ala Lys Gly Gln Pro Arg Glu Pro Gln Val Tyr Thr
            340                 345                 350 ctg cct cca agc cag gaa gag atg acc aag aac cag gtg tcc ctg acc     1104
Leu Pro Pro Ser Gln Glu Glu Met Thr Lys Asn Gln Val Ser Leu Thr
            355                 360                 365 tgt ctc gtg aaa ggc ttc tac ccc tcc gat atc gcc gtg gaa tgg gag     1152
Cys Leu Val Lys Gly Phe Tyr Pro Ser Asp Ile Ala Val Glu Trp Glu
370                 375                 380 tcc aac ggc cag cct gag aac aac tac aag acc acc ccc cct gtg ctg     1200
Ser Asn Gly Gln Pro Glu Asn Asn Tyr Lys Thr Thr Pro Pro Val Leu
385                 390                 395                 400 gac tcc gac ggc tcc ttc ttc ctg tac tct cgc ctg acc gtg gac aag     1248
Asp Ser Asp Gly Ser Phe Phe Leu Tyr Ser Arg Leu Thr Val Asp Lys
                405                 410                 415 tcc cgg tgg cag gaa ggc aac gtg ttc tcc tgc tcc gtg atg cac gag     1296
Ser Arg Trp Gln Glu Gly Asn Val Phe Ser Cys Ser Val Met His Glu
            420                 425                 430 gcc ctg cac aac cac tac acc cag aag tcc ctg tct ctg tcc ctg ggc     1344
Ala Leu His Asn His Tyr Thr Gln Lys Ser Leu Ser Leu Ser Leu Gly
            435                 440                 445 aag tga                                                              1350
Lys

<210> SEQ ID NO 14
<211> LENGTH: 449
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Ala Pro Gly Gln Gly Leu Glu Trp Met
        35                  40                  45

Gly Tyr Ile Asn Pro Tyr His Asp Val Thr Lys Tyr Asn Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                    85                  90                  95
Ala Arg Gln Gly Asp Pro Tyr Ser Gly Asn Tyr Gln Phe Thr Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                    405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 15
<211> LENGTH: 645
<212> TYPE: DNA
<213> ORGANISM: Artificial Sequence
<220> FEATURE:
<223> OTHER INFORMATION: antibody
<220> FEATURE:
<221> NAME/KEY: CDS
```

<222> LOCATION: (1)..(645)

<400> SEQUENCE: 15

```
gac atc cag atg acc cag tct cca tcc tct ctg tcc gcc tct gtg ggc        48
Asp Ile Gln Met Thr Gln Ser Pro Ser Ser Leu Ser Ala Ser Val Gly
1               5                   10                  15 gac aga gtg acc atc acc tgt aga gcc tct cag gac gtg tcc acc gag        96
Asp Arg Val Thr Ile Thr Cys Arg Ala Ser Gln Asp Val Ser Thr Glu
                20                  25                  30 gtc gtg tgg tat cag cag aag cct ggc aag gcc cct aag ctg ctg atc       144
Val Val Trp Tyr Gln Gln Lys Pro Gly Lys Ala Pro Lys Leu Leu Ile
            35                  40                  45 tac tcc gcc tcc tac cgg tac tct ggc gtg ccc tct aga ttc tcc ggc       192
Tyr Ser Ala Ser Tyr Arg Tyr Ser Gly Val Pro Ser Arg Phe Ser Gly
        50                  55                  60 tct ggc tct ggc acc gac ttt acc ctg aca atc tcc agc ctg cag cct       240
Ser Gly Ser Gly Thr Asp Phe Thr Leu Thr Ile Ser Ser Leu Gln Pro
65                  70                  75                  80 gag gac ttc gcc acc tac tac tgc cag cag cac tac agc acc cct tac       288
Glu Asp Phe Ala Thr Tyr Tyr Cys Gln Gln His Tyr Ser Thr Pro Tyr
                85                  90                  95 acc ttt ggc cag ggc acc aag ctg gaa atc aag cgg aca gtg gcc gct       336
Thr Phe Gly Gln Gly Thr Lys Leu Glu Ile Lys Arg Thr Val Ala Ala
                100                 105                 110 cct tcc gtg ttc atc ttc cca cct tcc gac gag cag ctg aag tcc ggc       384
Pro Ser Val Phe Ile Phe Pro Pro Ser Asp Glu Gln Leu Lys Ser Gly
            115                 120                 125 aca gct tct gtc gtg tgc ctg ctg aac aac ttc tac cct cgg gaa gcc       432
Thr Ala Ser Val Val Cys Leu Leu Asn Asn Phe Tyr Pro Arg Glu Ala
        130                 135                 140 aag gtg cag tgg aag gtg gac aat gcc ctg cag tcc ggc aac tcc caa       480
Lys Val Gln Trp Lys Val Asp Asn Ala Leu Gln Ser Gly Asn Ser Gln
145                 150                 155                 160 gag tct gtg acc gag cag gac tcc aag gac agc acc tac agc ctg tcc       528
Glu Ser Val Thr Glu Gln Asp Ser Lys Asp Ser Thr Tyr Ser Leu Ser
                165                 170                 175 tcc aca ctg acc ctg tcc aag gcc gac tac gag aag cac aag gtg tac       576
Ser Thr Leu Thr Leu Ser Lys Ala Asp Tyr Glu Lys His Lys Val Tyr
                180                 185                 190 gcc tgc gaa gtg acc cat cag ggc ctg tct agc cct gtg acc aag tct       624
Ala Cys Glu Val Thr His Gln Gly Leu Ser Ser Pro Val Thr Lys Ser
            195                 200                 205 ttc aac cgg ggc gag tgc tga                                            645
Phe Asn Arg Gly Glu Cys
        210
```

<210> SEQ ID NO 16
<211> LENGTH: 214
<212> TYPE: PRT
<213> ORGANISM: Artificial Sequence
<220> FEATURE:
<223> OTHER INFORMATION: Synthetic Construct

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Glu
                20                  25                  30

Val Val Trp Tyr Gln Gln Lys Pro Gly Lys Ala Pro Lys Leu Leu Ile
            35                  40                  45
```

```
Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 17
<211> LENGTH: 366
<212> TYPE: DNA
<213> ORGANISM: Artificial Sequence
<220> FEATURE:
<223> OTHER INFORMATION: antibody variable region
<220> FEATURE:
<221> NAME/KEY: CDS
<222> LOCATION: (1)..(366)

<400> SEQUENCE: 17

```
gag gtg cag ttg gtt gaa tct ggc gga gga ctg gtt cag cct ggc gga      48
Glu Val Gln Leu Val Glu Ser Gly Gly Gly Leu Val Gln Pro Gly Gly
 1               5                  10                  15 tct ctg aga ctg tct tgt gcc gcc tct ggc ttc gtg ttc agc tcc gac      96
Ser Leu Arg Leu Ser Cys Ala Ala Ser Gly Phe Val Phe Ser Ser Asp
            20                  25                  30 gat atg tcc tgg gtc cga cag gct cct ggc aaa gga ttg gag tgg gtc     144
Asp Met Ser Trp Val Arg Gln Ala Pro Gly Lys Gly Leu Glu Trp Val
        35                  40                  45 gcc tac atc tct tct ggc ggc gac tac acc tac tat ccc gac acc gtg     192
Ala Tyr Ile Ser Ser Gly Gly Asp Tyr Thr Tyr Tyr Pro Asp Thr Val
    50                  55                  60 aag ggc aga ttc acc atc tcc aga gac aac gcc aag aac tcc ctg tac     240
Lys Gly Arg Phe Thr Ile Ser Arg Asp Asn Ala Lys Asn Ser Leu Tyr
 65                  70                  75                  80 ctg cag atg aac agc ctg aga gcc gag gac acc gcc gtg tac tac tgt     288
Leu Gln Met Asn Ser Leu Arg Ala Glu Asp Thr Ala Val Tyr Tyr Cys
                85                  90                  95 gcc aga cac ctg tac ggc tcc tcc agc tac tac gtg atg gac tat tgg     336
Ala Arg His Leu Tyr Gly Ser Ser Ser Tyr Tyr Val Met Asp Tyr Trp
            100                 105                 110 ggc cag ggc acc ctg gtc aca gtg tcc tct                             366
Gly Gln Gly Thr Leu Val Thr Val Ser Ser
        115                 120
```

<210> SEQ ID NO 18
<211> LENGTH: 122
<212> TYPE: PRT
<213> ORGANISM: Artificial Sequence
<220> FEATURE:
<223> OTHER INFORMATION: Synthetic Construct

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Asp
            20                  25                  30

Asp Met Ser Trp Val Arg Gln Ala Pro Gly Lys Gly Leu Glu Trp Val
        35                  40                  45

Ala Tyr Ile Ser Ser Gly Gly Asp Tyr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Leu Tyr Gly Ser Ser Ser Tyr Tyr Val Met Asp Tyr Trp
            100                 105                 110

Gly Gln Gly Thr Leu Val Thr Val Ser Ser
        115                 120
```

<210> SEQ ID NO 19
<211> LENGTH: 321
<212> TYPE: DNA
<213> ORGANISM: Artificial Sequence
<220> FEATURE:
<223> OTHER INFORMATION: antibody variable region
<220> FEATURE:
<221> NAME/KEY: CDS
<222> LOCATION: (1)..(321)

<400> SEQUENCE: 19

```
gac atc cag atg acc cag tct cca tcc tct ctg tct gcc agc ctg ggc      48
Asp Ile Gln Met Thr Gln Ser Pro Ser Ser Leu Ser Ala Ser Leu Gly
1               5                   10                  15 gac aga atc acc atc acc tgt cac gcc agc cag aac atc aac gtg tgg      96
Asp Arg Ile Thr Ile Thr Cys His Ala Ser Gln Asn Ile Asn Val Trp
            20                  25                  30 ctg tcc tgg tat cag cag aag ccc ggc aag atc ccc aag ctg ctg gtg     144
Leu Ser Trp Tyr Gln Gln Lys Pro Gly Lys Ile Pro Lys Leu Leu Val
        35                  40                  45 tac aag gcc tcc aat ctg cac acc ggc gtg ccc tct aga ttc tcc gga     192
Tyr Lys Ala Ser Asn Leu His Thr Gly Val Pro Ser Arg Phe Ser Gly
    50                  55                  60 tct ggc tct ggc acc gac ttt acc ctg aca atc tcc agc ctg cag cct     240
Ser Gly Ser Gly Thr Asp Phe Thr Leu Thr Ile Ser Ser Leu Gln Pro
65                  70                  75                  80 gag gac ttc gcc acc tac tat tgt cag cag ggc cag agc tac cct ctg     288
Glu Asp Phe Ala Thr Tyr Tyr Cys Gln Gln Gly Gln Ser Tyr Pro Leu
                85                  90                  95 acc ttt ggc gct ggc acc aag ctg gaa atc aag                         321
Thr Phe Gly Ala Gly Thr Lys Leu Glu Ile Lys
            100                 105
```

<210> SEQ ID NO 20
<211> LENGTH: 107
<212> TYPE: PRT
<213> ORGANISM: Artificial Sequence

```
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Leu Gly
1               5                   10                  15

Asp Arg Ile Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Val
        35                  40                  45

Tyr Lys Ala Ser Asn Leu His Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
                85                  90                  95

Thr Phe Gly Ala Gly Thr Lys Leu Glu Ile Lys
            100                 105

<210> SEQ ID NO 21
<211> LENGTH: 366
<212> TYPE: DNA
<213> ORGANISM: Artificial Sequence
<220> FEATURE:
<223> OTHER INFORMATION: antibody variable region
<220> FEATURE:
<221> NAME/KEY: CDS
<222> LOCATION: (1)..(366)

<400> SEQUENCE: 21 cag gtg cag ttg gtt cag tct ggc gcc gaa gtg aag aaa cct ggc gcc        48
Gln Val Gln Leu Val Gln Ser Gly Ala Glu Val Lys Lys Pro Gly Ala
1               5                   10                  15 tct gtg aag gtg tcc tgc aag gct tcc ggc tac acc ttt acc agc tac        96
Ser Val Lys Val Ser Cys Lys Ala Ser Gly Tyr Thr Phe Thr Ser Tyr
            20                  25                  30 gtg atc cac tgg gtc cga cag gct cca gga caa ggc ttg gag tgg atg       144
Val Ile His Trp Val Arg Gln Ala Pro Gly Gln Gly Leu Glu Trp Met
        35                  40                  45 ggc tac atc aac ccc tac cac gac gtg acc aag tac aac gag aag ttc       192
Gly Tyr Ile Asn Pro Tyr His Asp Val Thr Lys Tyr Asn Glu Lys Phe
    50                  55                  60 cag ggc aga gtg acc atg acc aga gac acc tcc acc agc acc gtg tac       240
Gln Gly Arg Val Thr Met Thr Arg Asp Thr Ser Thr Ser Thr Val Tyr
65                  70                  75                  80 atg gaa ctg tcc agc ctg aga tcc gag gac acc gcc gtg tac tac tgc       288
Met Glu Leu Ser Ser Leu Arg Ser Glu Asp Thr Ala Val Tyr Tyr Cys
                85                  90                  95 gcc aga cag ggc gac cct tac tcc ggc aac tac cag ttt acc tac tgg       336
Ala Arg Gln Gly Asp Pro Tyr Ser Gly Asn Tyr Gln Phe Thr Tyr Trp
            100                 105                 110 ggc cag ggc acc ctg gtc aca gtt tct tcc                               366
Gly Gln Gly Thr Leu Val Thr Val Ser Ser
        115                 120

<210> SEQ ID NO 22
<211> LENGTH: 122
<212> TYPE: PRT
<213> ORGANISM: Artificial Sequence
<220> FEATURE:
<223> OTHER INFORMATION: Synthetic Construct
```

-continued

```
<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Ala Pro Gly Gln Gly Leu Glu Trp Met
        35                  40                  45

Gly Tyr Ile Asn Pro Tyr His Asp Val Thr Lys Tyr Asn Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gln Gly Asp Pro Tyr Ser Gly Asn Tyr Gln Phe Thr Tyr Trp
            100                 105                 110

Gly Gln Gly Thr Leu Val Thr Val Ser Ser
        115                 120

<210> SEQ ID NO 23
<211> LENGTH: 321
<212> TYPE: DNA
<213> ORGANISM: Artificial Sequence
<220> FEATURE:
<223> OTHER INFORMATION: antibody variable region
<220> FEATURE:
<221> NAME/KEY: CDS
<222> LOCATION: (1)..(321)

<400> SEQUENCE: 23 gac atc cag atg acc cag tct cca tcc tct ctg tcc gcc tct gtg ggc       48
Asp Ile Gln Met Thr Gln Ser Pro Ser Ser Leu Ser Ala Ser Val Gly
1               5                   10                  15 gac aga gtg acc atc acc tgt aga gcc tct cag gac gtg tcc acc gag       96
Asp Arg Val Thr Ile Thr Cys Arg Ala Ser Gln Asp Val Ser Thr Glu
            20                  25                  30 gtc gtg tgg tat cag cag aag cct ggc aag gcc cct aag ctg ctg atc      144
Val Val Trp Tyr Gln Gln Lys Pro Gly Lys Ala Pro Lys Leu Leu Ile
        35                  40                  45 tac tcc gcc tcc tac cgg tac tct ggc gtg ccc tct aga ttc tcc ggc      192
Tyr Ser Ala Ser Tyr Arg Tyr Ser Gly Val Pro Ser Arg Phe Ser Gly
    50                  55                  60 tct ggc tct ggc acc gac ttt acc ctg aca atc tcc agc ctg cag cct      240
Ser Gly Ser Gly Thr Asp Phe Thr Leu Thr Ile Ser Ser Leu Gln Pro
65                  70                  75                  80 gag gac ttc gcc acc tac tac tgc cag cag cac tac agc acc cct tac      288
Glu Asp Phe Ala Thr Tyr Tyr Cys Gln Gln His Tyr Ser Thr Pro Tyr
                85                  90                  95 acc ttt ggc cag ggc acc aag ctg gaa atc aag                          321
Thr Phe Gly Gln Gly Thr Lys Leu Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Ser Thr Glu
            20                  25                  30

Val Val Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Tyr
                85                  90                  95

Thr Phe Gly Gln Gly Thr Lys Leu Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: CDR

<400> SEQUENCE: 25

Ser Asp Asp Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: CDR

<400> SEQUENCE: 26

Tyr Ile Ser Ser Gly Gly Asp Tyr Thr Tyr Tyr Pro Asp Thr Val Lys
1               5                   10                  15

Gly

<210> SEQ ID NO 27
<211> LENGTH: 13
<212> TYPE: PRT
<213> ORGANISM: Artificial Sequence
<220> FEATURE:
<223> OTHER INFORMATION: CDR

<400> SEQUENCE: 27

His Leu Tyr Gly Ser Ser Ser Tyr Tyr Val Met Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: CDR

<400> SEQUENCE: 28

His Ala Ser Gln Asn Ile Asn Val Trp Leu Ser
1               5                   10

<210> SEQ ID NO 29
<211> LENGTH: 7
<212> TYPE: PRT
<213> ORGANISM: Artificial Sequence
<220> FEATURE:
```

<223> OTHER INFORMATION: CDR

<400> SEQUENCE: 29

Lys Ala Ser Asn Leu His Thr
1               5

<210> SEQ ID NO 30
<211> LENGTH: 9
<212> TYPE: PRT
<213> ORGANISM: Artificial Sequence
<220> FEATURE:
<223> OTHER INFORMATION: CDR

<400> SEQUENCE: 30

Gln Gln Gly Gln Ser Tyr Pro Leu Thr
1               5

<210> SEQ ID NO 31
<211> LENGTH: 5
<212> TYPE: PRT
<213> ORGANISM: Artificial Sequence
<220> FEATURE:
<223> OTHER INFORMATION: CDR

<400> SEQUENCE: 31

Ser Tyr Val Ile His
1               5

<210> SEQ ID NO 32
<211> LENGTH: 17
<212> TYPE: PRT
<213> ORGANISM: Artificial Sequence
<220> FEATURE:
<223> OTHER INFORMATION: CDR

<400> SEQUENCE: 32

Tyr Ile Asn Pro Tyr His Asp Val Thr Lys Tyr Asn Glu Lys Phe Gln
1               5                   10                  15

Gly

<210> SEQ ID NO 33
<211> LENGTH: 13
<212> TYPE: PRT
<213> ORGANISM: Artificial Sequence
<220> FEATURE:
<223> OTHER INFORMATION: CDR

<400> SEQUENCE: 33

Gln Gly Asp Pro Tyr Ser Gly Asn Tyr Gln Phe Thr Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CDR

<400> SEQUENCE: 34

Arg Ala Ser Gln Asp Val Ser Thr Glu Val Val
1               5                   10

<210> SEQ ID NO 35
<211> LENGTH: 7
<212> TYPE: PRT
<213> ORGANISM: Artificial Sequence

```
<220> FEATURE:
<223> OTHER INFORMATION: CDR

<400> SEQUENCE: 35

Ser Ala Ser Tyr Arg Tyr Ser
1               5

<210> SEQ ID NO 36
<211> LENGTH: 9
<212> TYPE: PRT
<213> ORGANISM: Artificial Sequence
<220> FEATURE:
<223> OTHER INFORMATION: CDR

<400> SEQUENCE: 36

Gln Gln His Tyr Ser Thr Pro Tyr Thr
1               5

<210> SEQ ID NO 37
<211> LENGTH: 1359
<212> TYPE: DNA
<213> ORGANISM: artificial sequence
<220> FEATURE:
<223> OTHER INFORMATION: heavy chain of chimera anti-CD80 antibody

<400> SEQUENCE: 37
gaagtgaagc tgttggagtc tggcggcgga ctggttaagc ctggcggatc tctgaagctg      60
tcttgtgccg cctctggctt cgtgttcagc tccgacgata tgtcctgggt ccgacagtct     120
cctgagaagc ggcttgagtg ggtcgcctac atctcttccg gcggagacta cacctactat     180
cccgacaccg tgaagggcag attcaccatc tccagagaca cgccaagaa caccctgtac      240 ctgcagatgt ccagcctgaa gtctgaggac accgccatgt actactgcgc cagacacctg     300
tacggctcct ccagctacta cgtgatggac tattggggcc agggcacctc tgtcacagtg     360
tcctctgctt ccaccaaggg acccagcgtg ttccctctgg ctccttccag caagtctacc     420 tctgcggaa cagctgctct gggctgcctg gtcaaggact actttcctga gcctgtgacc      480
gtgtcctgga ctctggcgc tctgacatct ggcgtgcaca cattccctgc tgtgctgcag      540
tcctccggcc tgtactctct gtcctctgtc gtgaccgtgc cttccagctc tctgggaacc     600
cagacctaca tctgcaatgt gaaccacaag ccttccaaca ccaaggtgga caagaaggtg     660
gaacccaagt cctgcgacaa gacccacacc tgtcctccat gtcctgctcc agaactgctc     720
ggcggacctt ccgtgttcct gtttcctcca aagcctaagg acaccctgat gatctctcgg     780 accctgaag tgacctgcgt ggtggtggat gtgtcccacg aggacccaga agtgaagttc      840
aattggtacg tggacggcgt ggaagtgcac aacgccaaga ccaagcctag agaggaacag     900
tacaactcca cctacagagt ggtgtccgtg ctgaccgtgc tgcaccagga ttggctgaac     960
ggcaaagagt acaagtgcaa ggtgtccaac aaggccctgc ctgctcctat cgaaaagacc    1020
atctccaagg ccaagggcca gcctcgagaa cccaggtttt acaccttgcc tccatctcgg    1080
gacgagctga ccaagaacca ggtgtccctg acctgtctcg tgaagggctt ctaccctcc     1140 gacattgccg tggaatggga gtctaatggc cagccagaga caactacaa gacaacccct     1200 cctgtgctga ctccgacgg ctcattcttc ctgtactcca agctgacagt ggacaagtcc     1260
agatggcagc agggcaacgt gttctcctgc tccgtgatgc acgaggccct gcacaatcac    1320
tacacacaga agtccctgtc tctgagcccc ggcaaatga                            1359

<210> SEQ ID NO 38
```

```
<211> LENGTH: 452
<212> TYPE: PRT
<213> ORGANISM: artificial sequence
<220> FEATURE:
<223> OTHER INFORMATION: heavy chain of chimera anti-CD80 antibody

<400> SEQUENCE: 38

Glu Val Lys Leu Leu Glu Ser Gly Gly Gly Leu Val Lys Pro Gly Gly
1               5                   10                  15

Ser Leu Lys Leu Ser Cys Ala Ala Ser Gly Phe Val Phe Ser Ser Asp
            20                  25                  30

Asp Met Ser Trp Val Arg Gln Ser Pro Glu Lys Arg Leu Glu Trp Val
        35                  40                  45

Ala Tyr Ile Ser Ser Gly Gly Asp Tyr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Leu Tyr Gly Ser Ser Tyr Tyr Val Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450
```

<210> SEQ ID NO 39
<211> LENGTH: 645
<212> TYPE: DNA
<213> ORGANISM: artificial sequence
<220> FEATURE:
<223> OTHER INFORMATION: light chain of chimera anti-CD80 antibody

<400> SEQUENCE: 39

```
gacatccaga tgacccagtc tccatcctct ctgtctgcca gcctgggcga caccatcacc    60
atcacatgtc acgccagcca gaacatcaac gtgtggctgt cctggtatca gcagaagccc   120
ggcaacatcc ccaagctgct ggtgtacaag gcctccaatc tgcacaccgg cgtgccctct   180
agattctccg gatctggctc tggcaccggc tttaccctga caatcagctc cttgcagccc   240
gaggacattg ccacctacta ctgtcagcag ggccagagct accctctgac ctttggcgct   300
ggcaccaagc tggaactgaa gcggacagtg gccgctcctt ccgtgttcat cttcccacct   360
tccgacgagc agctgaagtc cggcacagct tctgtcgtgt gcctgctgaa caacttctac   420
cctcgggaag ccaaggtgca gtggaaggtg acaatgccc tgcagtccgg caactcccaa    480
gagtctgtga ccgagcagga ctccaaggac agcacctaca gcctgtcctc cacactgacc   540
ctgtccaagg ccgactacga aaagcacaag gtgtacgcct gcgaagtgac ccatcagggc   600
ctgtctagcc ctgtgaccaa gtctttcaac cggggcgagt gctga              645
```

<210> SEQ ID NO 40
<211> LENGTH: 214
<212> TYPE: PRT
<213> ORGANISM: artificial sequence
<220> FEATURE:
<223> OTHER INFORMATION: light chain of chimera anti-CD80 antibody

<400> SEQUENCE: 40

```
Asp Ile Gln Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Val
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 41
<211> LENGTH: 1359
<212> TYPE: DNA
<213> ORGANISM: artificial sequence
<220> FEATURE:
<223> OTHER INFORMATION: heavy chain of chimera anti-CD86 antibody

<400> SEQUENCE: 41
gaggttcagt tgcagcagtc tggacccgag ctggtcaagc ctggcacctc cgtgaagatg      60
tcctgcaagg cctccggcta caccttcacc agctacgtga tccactgggt caaagagaag     120
ccaggccagg ccttgagtg gatcggctac atcaaccct accacgacgt gaccaagtac       180
aacgagaagt tcaagggcag agctaccctg acctccgaca gtcctcttc caccgcctac      240 atggaactgt ccagcctgac ctctgaggac tccgccgtgt actactgctc tagacagggc      300 gaccccttact ccggcaacta ccagtttacc tactggggcc agggcaccct ggtcacagtt    360
tctgccgctt ccaccaaggg acccagcgtg ttccctctgg ctccttccag caagtctacc     420
tctggcggaa cagctgctct gggctgcctg gtcaaggact actttcctga gcctgtgacc     480
gtgtcctgga actctggcgc tctgacatct ggcgtgcaca cattccctgc tgtgctgcag     540
tcctccggcc tgtactctct gtcctctgtc gtgaccgtgc cttccagctc tctgggaacc     600
cagacctaca tctgcaatgt gaaccacaag ccttccaaca ccaaggtgga caagaaggtg     660
gaacccaagt cctgcgacaa gacccacacc tgtcctccat gtcctgctcc agaactgctc     720
ggcggacctt ccgtgttcct gtttcctcca agcctaagg acaccctgat gatctctcgg     780
acccctgaag tgacctgcgt ggtggtggat gtgtcccacg aggacccaga agtgaagttc     840
aattggtacg tggacggcgt ggaagtgcac aacgccaaga ccaagcctag agaggaacag     900
tacaactcca cctacagagt ggtgtccgtg ctgaccgtgc tgcaccagga ttggctgaac     960
ggcaaagagt acaagtgcaa ggtgtccaac aaggccctgc ctgctcctat cgaaaagacc    1020
atctccaagg ccaagggcca gcctcgagaa ccccaggttt acaccttgcc tccatctcgg    1080
gacgagctga ccaagaacca ggtgtccctg acctgtctcg tgaagggctt ctaccctcc    1140 gacattgccg tggaatggga gtctaatggc cagccagaga caactacaa gacaaccct     1200 cctgtgctga ctccgacgg ctcattcttc ctgtactcca agctgacagt ggacaagtcc    1260
agatggcagc agggcaacgt gttctcctgc tccgtgatgc acgaggccct gcacaatcac    1320
tacacacaga gtccctgtc tctgagcccc ggcaaatga                            1359

<210> SEQ ID NO 42
```

```
<211> LENGTH: 452
<212> TYPE: PRT
<213> ORGANISM: artificial sequence
<220> FEATURE:
<223> OTHER INFORMATION: heavy chain of chimera anti-CD86 antibody

<400> SEQUENCE: 42

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Ser Tyr
            20                  25                  30

Val Ile His Trp Val Lys Glu Lys Pro Gly Gln Gly Leu Glu Trp Ile
        35                  40                  45

Gly Tyr Ile Asn Pro Tyr His Asp Val Thr Lys Tyr Asn Glu Lys Phe
    50                  55                  60

Lys Gly Arg Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Arg Gln Gly Asp Pro Tyr Ser Gly Asn Tyr Gln Phe Thr Tyr Trp
            100                 105                 110

Gly Gln Gly Thr Leu Val Thr Val Ser Ala Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 43
<211> LENGTH: 645
<212> TYPE: DNA
<213> ORGANISM: artificial sequence
<220> FEATURE:
<223> OTHER INFORMATION: light chain of chimera anti-CD86 antibody

<400> SEQUENCE: 43
gacatcgtga tgtcccagag ccacaagttc atgtccacct ccgtgggcga cagagtgtct    60
atcgcctgca aggcctctca ggacgtgtcc acagaggtcg tgtggttcca gcagaagcct   120
ggccagtctc ctaagctgct gatctactcc gcctcctaca gatacaccgg cgtgcccgat   180
agattcaccg gctctggctc tggcaccgac tttaccttca ccatcagctc cgtgcaggcc   240
gaggatctgg ccgtgtacta ctgtcagcag cactacagca ccccttacac ctttggcgga   300
ggcaccaagc tggaaatcaa gcggacagtg gccgctcctt ccgtgttcat cttcccacct   360
tccgacgagc agctgaagtc cggcacagct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctaca gcctgtcctc cacactgacc   540
ctgtccaagg ccgactacga aagcacaag gtgtacgcct gcgaagtgac ccatcagggc   600
ctgtctagcc ctgtgaccaa gtctttcaac cggggcgagt gctga              645

<210> SEQ ID NO 44
<211> LENGTH: 214
<212> TYPE: PRT
<213> ORGANISM: artificial sequence
<220> FEATURE:
<223> OTHER INFORMATION: light chain of chimera anti-CD86 antibody

<400> SEQUENCE: 44

Asp Ile Val Met Ser Gln Ser His Lys Phe Met Ser Thr Ser Val Gly
1               5                   10                  15

Asp Arg Val Ser Ile Ala Cys Lys Ala Ser Gln Asp Val Ser Thr Glu
            20                  25                  30

Val Val Trp Phe Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 45
<211> LENGTH: 366
<212> TYPE: DNA
<213> ORGANISM: artificial sequence
<220> FEATURE:
<223> OTHER INFORMATION: heavy chain variable region of chimera
      anti-CD80 antibody

<400> SEQUENCE: 45
gaagtgaagc tgttggagtc tggcggcgga ctggttaagc ctggcggatc tctgaagctg    60
tcttgtgccg cctctggctt cgtgttcagc tccgacgata tgtcctgggt ccgacagtct   120
cctgagaagc ggcttgagtg ggtcgcctac atctcttccg gcggagacta cacctactat   180
cccgacaccg tgaagggcag attcaccatc tccagagaca cgccaagaa caccctgtac    240 ctgcagatgt ccagcctgaa gtctgaggac accgccatgt actactgcgc cagacacctg   300
tacggctcct ccagctacta cgtgatggac tattggggcc agggcacctc tgtcacagtg   360
tcctct                                                              366

<210> SEQ ID NO 46
<211> LENGTH: 122
<212> TYPE: PRT
<213> ORGANISM: artificial sequence
<220> FEATURE:
<223> OTHER INFORMATION: heavy chain variable region of chimera
      anti-CD80 antibody

<400> SEQUENCE: 46

Glu Val Lys Leu Leu Glu Ser Gly Gly Gly Leu Val Lys Pro Gly Gly
1               5                   10                  15

Ser Leu Lys Leu Ser Cys Ala Ala Ser Gly Phe Val Phe Ser Ser Asp
            20                  25                  30

Asp Met Ser Trp Val Arg Gln Ser Pro Glu Lys Arg Leu Glu Trp Val
        35                  40                  45

Ala Tyr Ile Ser Ser Gly Gly Asp Tyr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Leu Tyr Gly Ser Ser Tyr Tyr Val Met Asp Tyr Trp
            100                 105                 110

Gly Gln Gly Thr Ser Val Thr Val Ser Ser
```

<210> SEQ ID NO 47
<211> LENGTH: 321
<212> TYPE: DNA
<213> ORGANISM: artificial sequence
<220> FEATURE:
<223> OTHER INFORMATION: light chain variable region of chimera
      anti-CD80 antibody

<400> SEQUENCE: 47

```
gacatccaga tgacccagtc tccatcctct ctgtctgcca gcctgggcga caccatcacc    60
atcacatgtc acgccagcca gaacatcaac gtgtggctgt cctggtatca gcagaagccc   120
ggcaacatcc ccaagctgct ggtgtacaag gcctccaatc tgcacaccgg cgtgccctct   180
agattctccg gatctggctc tggcaccggc tttacccctg caatcagctc cttgcagccc   240
gaggacattg ccacctacta ctgtcagcag ggccagagct accctctgac ctttggcgct   300
ggcaccaagc tggaactgaa g                                             321
```

<210> SEQ ID NO 48
<211> LENGTH: 107
<212> TYPE: PRT
<213> ORGANISM: artificial sequence
<220> FEATURE:
<223> OTHER INFORMATION: light chain variable region of chimera
      anti-CD80 antibody

<400> SEQUENCE: 48

Asp Ile Gln Met Thr Gln Ser Pro Ser Ser Leu Ser Ala Ser Leu Gly
1               5                   10                  15
Asp Thr Ile Thr Ile Thr Cys His Ala Ser Gln Asn Ile Asn Val Trp
            20                  25                  30
Leu Ser Trp Tyr Gln Gln Lys Pro Gly Asn Ile Pro Lys Leu Leu Val
        35                  40                  45
Tyr Lys Ala Ser Asn Leu His Thr Gly Val Pro Ser Arg Phe Ser Gly
    50                  55                  60
Ser Gly Ser Gly Thr Gly Phe Thr Leu Thr Ile Ser Ser Leu Gln Pro
65                  70                  75                  80
Glu Asp Ile Ala Thr Tyr Tyr Cys Gln Gln Gly Gln Ser Tyr Pro Leu
                85                  90                  95
Thr Phe Gly Ala Gly Thr Lys Leu Glu Leu Lys
            100                 105

<210> SEQ ID NO 49
<211> LENGTH: 366
<212> TYPE: DNA
<213> ORGANISM: artificial sequence
<220> FEATURE:
<223> OTHER INFORMATION: heavy chain variable region of chimera
      anti-CD86 antibody

<400> SEQUENCE: 49

```
gaggttcagt tgcagcagtc tggacccgag ctggtcaagc ctggcacctc cgtgaagatg    60
tcctgcaagg cctccggcta caccttcacc agctacgtga tccactgggt caaagagaag   120
ccaggccagg gccttgagtg gatcggctac atcaacccct accacgacgt gaccaagtac   180
aacgagaagt tcaagggcag agctaccctg acctccgaca gtcctcttc accgcctac   240
atggaactgt ccagcctgac ctctgaggac tccgccgtgt actactgctc tagacagggc   300
gaccccttact ccggcaacta ccagtttacc tactggggcc agggcaccct ggtcacagtt   360
``` tctgcc                                                                  366

<210> SEQ ID NO 50
<211> LENGTH: 122
<212> TYPE: PRT
<213> ORGANISM: artificial sequence
<220> FEATURE:
<223> OTHER INFORMATION: heavy chain variable region of chimera
      anti-CD86 antibody

<400> SEQUENCE: 50

Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Ser Tyr
            20                  25                  30

Val Ile His Trp Val Lys Glu Lys Pro Gly Gln Gly Leu Glu Trp Ile
        35                  40                  45

Gly Tyr Ile Asn Pro Tyr His Asp Val Thr Lys Tyr Asn Glu Lys Phe
    50                  55                  60

Lys Gly Arg Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Arg Gln Gly Asp Pro Tyr Ser Gly Asn Tyr Gln Phe Thr Tyr Trp
            100                 105                 110

Gly Gln Gly Thr Leu Val Thr Val Ser Ala
        115                 120

<210> SEQ ID NO 51
<211> LENGTH: 321
<212> TYPE: DNA
<213> ORGANISM: artificial sequence
<220> FEATURE:
<223> OTHER INFORMATION: light chain variable region of chimera
      anti-CD86 antibody

<400> SEQUENCE: 51
gacatcgtga tgtcccagag ccacaagttc atgtccacct ccgtgggcga cagagtgtct       60
atcgcctgca aggcctctca ggacgtgtcc acagaggtcg tgtggttcca gcagaagcct      120
ggccagtctc ctaagctgct gatctactcc gcctcctaca gatacaccgg cgtgcccgat      180
agattcaccg gctctggctc tggcaccgac tttaccttca ccatcagctc cgtgcaggcc      240
gaggatctgg ccgtgtacta ctgtcagcag cactacagca cccccttaca ctttggcgga      300
ggcaccaagc tggaaatcaa g                                                321

<210> SEQ ID NO 52
<211> LENGTH: 107
<212> TYPE: PRT
<213> ORGANISM: artificial sequence
<220> FEATURE:
<223> OTHER INFORMATION: light chain variable region of chimera
      anti-CD86 antibody

<400> SEQUENCE: 52

Asp Ile Val Met Ser Gln Ser His Lys Phe Met Ser Thr Ser Val Gly
1               5                   10                  15

Asp Arg Val Ser Ile Ala Cys Lys Ala Ser Gln Asp Val Ser Thr Glu
            20                  25                  30

Val Val Trp Phe Gln Gln Lys Pro Gly Gln Ser Pro Lys Leu Leu Ile

```
                35                  40                  45
Tyr Ser Ala Ser Tyr Arg Tyr Thr Gly Val Pro Asp Arg Phe Thr Gly
         50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Tyr
                 85                  90                  95

Thr Phe Gly Gly Gly Thr Lys Leu Glu Ile Lys
            100                 105
```

<210> SEQ ID NO 53
<211> LENGTH: 5
<212> TYPE: PRT
<213> ORGANISM: artificial sequence
<220> FEATURE:
<223> OTHER INFORMATION: CDRH1 of chimera anti-CD80 antibody

<400> SEQUENCE: 53

```
Ser Asp Asp Met Ser
 1               5
```

<210> SEQ ID NO 54
<211> LENGTH: 17
<212> TYPE: PRT
<213> ORGANISM: artificial sequence
<220> FEATURE:
<223> OTHER INFORMATION: CDRH2 of chimera anti-CD80 antibody

<400> SEQUENCE: 54

```
Tyr Ile Ser Ser Gly Gly Asp Tyr Thr Tyr Tyr Pro Asp Thr Val Lys
 1               5                   10                  15

Gly
```

<210> SEQ ID NO 55
<211> LENGTH: 13
<212> TYPE: PRT
<213> ORGANISM: artificial sequence
<220> FEATURE:
<223> OTHER INFORMATION: CDRH3 of chimera anti-CD80 antibody

<400> SEQUENCE: 55

```
His Leu Tyr Gly Ser Ser Ser Tyr Tyr Val Met Asp Tyr
 1               5                   10
```

<210> SEQ ID NO 56
<211> LENGTH: 11
<212> TYPE: PRT
<213> ORGANISM: artificial sequence
<220> FEATURE:
<223> OTHER INFORMATION: CDRL1 of chimera anti-CD80 antibody

<400> SEQUENCE: 56

```
His Ala Ser Gln Asn Ile Asn Val Trp Leu Ser
 1               5                   10
```

<210> SEQ ID NO 57
<211> LENGTH: 7
<212> TYPE: PRT
<213> ORGANISM: artificial sequence
<220> FEATURE:
<223> OTHER INFORMATION: CDRL2 of chimera anti-CD80 antibody

<400> SEQUENCE: 57

```
Lys Ala Ser Asn Leu His Thr
```

```
<210> SEQ ID NO 58
<211> LENGTH: 9
<212> TYPE: PRT
<213> ORGANISM: artificial sequence
<220> FEATURE:
<223> OTHER INFORMATION: CDRL3 of chimera anti-CD80 antibody

<400> SEQUENCE: 58

Gln Gln Gly Gln Ser Tyr Pro Leu Thr
1               5

<210> SEQ ID NO 59
<211> LENGTH: 5
<212> TYPE: PRT
<213> ORGANISM: artificial sequence
<220> FEATURE:
<223> OTHER INFORMATION: CDRH1 of chimera anti-CD86 antibody

<400> SEQUENCE: 59

Ser Tyr Val Ile His
1               5

<210> SEQ ID NO 60
<211> LENGTH: 17
<212> TYPE: PRT
<213> ORGANISM: artificial sequence
<220> FEATURE:
<223> OTHER INFORMATION: CDRH2 of chimera anti-CD86 antibody

<400> SEQUENCE: 60

Tyr Ile Asn Pro Tyr His Asp Val Thr Lys Tyr Asn Glu Lys Phe Lys
1               5                   10                  15

Gly

<210> SEQ ID NO 61
<211> LENGTH: 13
<212> TYPE: PRT
<213> ORGANISM: artificial sequence
<220> FEATURE:
<223> OTHER INFORMATION: CDRH3 of chimera anti-CD86 antibody

<400> SEQUENCE: 61

Gln Gly Asp Pro Tyr Ser Gly Asn Tyr Gln Phe Thr Tyr
1               5                   10

<210> SEQ ID NO 62
<211> LENGTH: 11
<212> TYPE: PRT
<213> ORGANISM: artificial sequence
<220> FEATURE:
<223> OTHER INFORMATION: CDRL1 of chimera anti-CD86 antibody

<400> SEQUENCE: 62

Lys Ala Ser Gln Asp Val Ser Thr Glu Val Val
1               5                   10

<210> SEQ ID NO 63
<211> LENGTH: 7
<212> TYPE: PRT
<213> ORGANISM: artificial sequence
<220> FEATURE:
<223> OTHER INFORMATION: CDRL2 of chimera anti-CD86 antibody

<400> SEQUENCE: 63
```

```
Ser Ala Ser Tyr Arg Tyr Thr
1               5

<210> SEQ ID NO 64
<211> LENGTH: 9
<212> TYPE: PRT
<213> ORGANISM: artificial sequence
<220> FEATURE:
<223> OTHER INFORMATION: CDRL3 of chimera anti-CD86 antibody

<400> SEQUENCE: 64

Gln Gln His Tyr Ser Thr Pro Tyr Thr
1               5
```